(12) United States Patent
Sabelle et al.

(10) Patent No.: US 8,771,376 B2
(45) Date of Patent: Jul. 8, 2014

(54) COMPOSITION COMPRISING AT LEAST ONE 2-PYRROLIDONE FUNCTIONALIZED WITH AN ESTER OR AMIDE RADICAL, AND AT LEAST ONE PIGMENT OR DIRECT DYE, FOR DYEING KERATIN MATERIALS

(75) Inventors: Stéphane Sabelle, Paris (FR); Madeleine Leduc, Paris (FR); Christian Blaise, Saint Mande (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/703,040

(22) PCT Filed: Jun. 8, 2011

(86) PCT No.: PCT/EP2011/059519
§ 371 (c)(1),
(2), (4) Date: Feb. 28, 2013

(87) PCT Pub. No.: WO2011/154458
PCT Pub. Date: Dec. 15, 2011

(65) Prior Publication Data
US 2013/0152314 A1    Jun. 20, 2013

Related U.S. Application Data

(60) Provisional application No. 61/357,645, filed on Jun. 23, 2010.

(30) Foreign Application Priority Data

Jun. 9, 2010  (FR) ...................................... 10 54560

(51) Int. Cl.
*A61Q 5/10*      (2006.01)
*C07D 207/00*    (2006.01)

(52) U.S. Cl.
USPC ............. 8/405; 8/435; 8/574; 8/680; 548/400

(58) Field of Classification Search
USPC .................. 8/405, 435, 574, 680; 548/400
See application file for complete search history.

(56) References Cited

U.S. PATENT DOCUMENTS

| | | | |
|---|---|---|---|
| 2,811,496 A | 10/1957 | Knuth | |
| 2,826,588 A | 3/1958 | Feldkamp et al. | |
| 3,136,620 A | 6/1964 | Bucha et al. | |
| 4,070,370 A | 1/1978 | Elliott et al. | |
| 4,071,530 A | 1/1978 | Kuhlein et al. | |
| 4,228,259 A | 10/1980 | Kalopissis et al. | |
| 4,823,985 A | 4/1989 | Grollier et al. | |
| 5,708,151 A | 1/1998 | Mockli | |
| 5,990,479 A | 11/1999 | Weiss et al. | |
| 6,225,198 B1 | 5/2001 | Alivisatos et al. | |
| 8,067,651 B2 | 11/2011 | Leinweber et al. | |
| 2009/0042747 A1 | 2/2009 | Leinweber et al. | |
| 2009/0282624 A1 | 11/2009 | De Boni | |
| 2010/0183529 A1* | 7/2010 | Richard et al. .................. 424/60 |

FOREIGN PATENT DOCUMENTS

| | | |
|---|---|---|
| EP | 0069512 | 1/1983 |
| EP | 0714954 | 6/1996 |
| EP | 0928608 | 7/1999 |
| EP | 1184426 | 3/2002 |
| EP | 1342759 | 9/2003 |
| EP | 2022781 | 2/2009 |
| EP | 2028247 | 2/2009 |
| EP | 2095809 | 9/2009 |
| FR | 2243959 | 4/1976 |
| FR | 2290199 | 6/1976 |
| FR | 2361447 | 3/1978 |
| FR | 2586913 | 3/1987 |
| FR | 2679771 | 2/1993 |
| FR | 2696744 | 4/1994 |
| GB | 956253 | 4/1964 |
| WO | 95/01772 | 1/1995 |
| WO | 95/15144 | 6/1995 |
| WO | 01/62726 | 8/2001 |
| WO | 2008/131396 | 10/2008 |
| WO | 2010/039509 | 4/2010 |

OTHER PUBLICATIONS

STIC Search Report dated Apr. 9, 2013.*
International Search Report for PCT/EP2011/059519, dated Jul. 20, 2011.
PCT/IB/308 form for PCT/EP2011/059519, dated Oct. 11, 2012.
English language abstract for FR 2 696 744, (1994).
English language abstract for FR 2 679 771, (1993).
Dabbousi, B.O., et al., "(CdSe)ZnS Core-Shell Quantum Dots: Synthesis and Characterization of a Size Series of Highly Luminescent Nanocrystallites," J. Phys. Chem. B, 101, 1997, pp. 9463-9475.
Felluga, Fulvia, et al., "A Chemoenzymatic Approach to the Synthesis of Enantiomerically Pure Aza Analogues of Paraconic Acid Methyl Ester and Both Enantiomers of Methyl β-proline," Tetrahedron: Asymmetry, 12, (2001), pp. 3241-3249.
Kenda, Benoit M., et al., "Discovery of 4-Substituted Pyrrolidone Butanamides as New Agents with Significant Antiepileptic Activity," J. Med. Chem., 47, 2004, pp. 530-549.

(Continued)

*Primary Examiner* — Elisa Elhilo
(74) *Attorney, Agent, or Firm* — The Marbury Law Group, PLLC

(57) ABSTRACT

The invention relates to a composition for dyeing keratin materials, and in particular human keratin fibres such as the hair, comprising at least one 2-pyrrolidone functionalized in the 4 position with an ester or amide radical, and at least one hydrophobic direct dye or a pigment; a dyeing process using this composition. Similarly, the invention relates to the use of the said pyrrolidone combined with a direct dye or a pigment for dyeing keratin materials, and especially to the use of the said pyrrolidone for improving the colour uptake onto the fibres of direct dyes that are sparingly soluble or insoluble in aqueous-alcoholic supports. The invention also relates to novel pyrrolidone derivatives. The present invention makes it possible in particular to obtain direct dyeing on keratin materials that is fast, resistant to washing, chromatic and powerful.

21 Claims, No Drawings

(56) References Cited

OTHER PUBLICATIONS

Peng, Xiaogang, et al., "Epitaxial Growth of Highly Luminescent CdSe/CDS Core/Shell Nanocrystals with Photostability and Electric Accessibility," J. Am. Chem. Soc., 119, 1997, pp. 7019-7029.

Sasaki, Hitoshi, et al., "Enhancing Effect of Pyrrolidone Derivatives on Transdermal Drug Delivery. I.," International Journal of Pharmaceutics, 44, (1988), pp. 15-24.

Sauer, John C., et al., "The Selective Hydrogenation of Substituted Amides," J. Am. Chem. Soc., 47, 1955, pp. 402-406.

Scarborough, Homer C., et al., "Pyrrolidines. V. 3-Pyrrolidinylmethylamines and Quinoline Derivatives," J. Org. Chem., 26, 1961, pp. 4955-4959.

Wu, Yao-Hua, et al., "Pyrrolidines. I. 1-Substituted 3-Pyrrolidinylmethyl Alcohol and Chlorides," J. Org. Chem., 26, 1961, pp. 1519-1524.

* cited by examiner

COMPOSITION COMPRISING AT LEAST ONE 2-PYRROLIDONE FUNCTIONALIZED WITH AN ESTER OR AMIDE RADICAL, AND AT LEAST ONE PIGMENT OR DIRECT DYE, FOR DYEING KERATIN MATERIALS

This is a national stage application of Pct/EP2011/059519, filed internationally on Jun. 8, 2011, which claims the benefit of U.S. Provisional Application No. 61/357,645, filed on Jun. 23, 2010, and claims priority to French Application No. 1054560, filed Jun. 9, 2010.

The invention relates to a composition for dyeing keratin fibres, and in particular human keratin fibres such as the hair, comprising at least one 2-pyrrolidone functionalized in position 4 with an ester or amide radical, and at least one pigment and/or hydrophobic direct dye, and to a dyeing process using this composition. The invention also relates to novel pyrrolidone derivatives.

It is known practice to dye keratin fibres, especially human keratin fibres, by direct dyeing. The process conventionally used in direct dyeing consists in directly applying to keratin fibres "direct" dyes, which are coloured and colouring molecules that have affinity for the said fibres. Generally, these dyes are predissolved in aqueous-alcoholic formulation supports. The compositions comprising these dyes are then left to stand on the fibres so that they diffused therein, and the fibres are then rinsed.

The colorations resulting therefrom are temporary or semi-permanent colorations since they have a tendency to fade rapidly after successive washing with shampoo. Specifically, most of the dyes used in direct dyeing are water-soluble and are desorbed from the fibre during shampooing.

It has moreover already been proposed to use pigments, as in patent application FR 2 741 530, which recommends the use, for the dyeing of keratin fibres, of a composition comprising particular film-forming polymers and dispersed pigments. The colorations obtained via this dyeing method have the drawback of having poor shampoo resistance and unsatisfactory colorations, especially in terms of chromaticity.

2-Pyrrolidone derivatives functionalized with esters in position 4 are known in the field of inks (see, for example, EP 1 342 759, WO 2008/131 396); for improving the transdermal passage of medicaments (*Int. J. Pharmaceutics*, 44(1-3), 15-24 (1988)) and as natural gas inhibitors (EP 2 028 247 and EP 2 022 781). Other 2-pyrrolidones functionalized with amides have been used in inkjet printing formulations (EP 2 142 610); as antiepileptics (*J. Med. Chem.* 47(3), 530-549 (2004)); as anticonvulsives (WO 2001/062 726) or as lubricant oil additives (FR 2 243 959) or gel additives (WO 2010/039 509).

In the field of dyeing keratin fibres, it is very difficult to use direct dyes or pigments that are sparingly soluble or insoluble in water or in aqueous-alcoholic solvents and to obtain satisfactory coloration of the keratin fibres especially in terms of colour uptake, selectivity, power or chromaticity, which can give varied shades, while at the same time being sufficiently resistant to successive shampooing, or to sweat.

This technical problem has been solved by treating keratin materials with a composition comprising, in a suitable cosmetic medium:
  i) at least one compound of general formula (I); and
  ii) at least one pigment and/or at least one direct dye that are sparingly soluble or insoluble in standard aqueous-alcoholic supports such as water, and especially the pigment(s) and/or direct dye(s) have a solubility of less than 20 grams per liter of water, compound of formula (I):

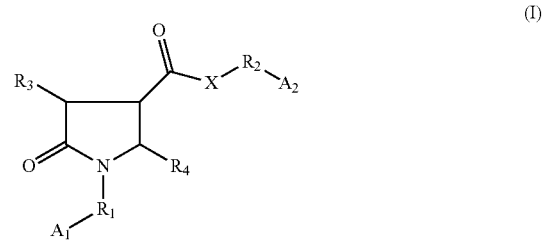

and also the organic or mineral acid or base salts thereof, optical isomers thereof: stereoisomers or enantiomers and diastereoisomers, geometrical isomers and tautomers, and the solvates thereof such as hydrates; in which formula (I):

X represents an oxygen atom or a divalent amino group —N($R_5$)—; with $R_5$ representing a hydrogen atom or a linear or branched ($C_1$-$C_{30}$)alkyl group, particularly ($C_1$-$C_6$)alkyl, optionally substituted with one or more groups —OH, —SH, —$NH_2$, tri($C_1$-$C_6$)alkylammonium, or cationic heteroaryl such as pyridinium, imidazolium and/or guanidinium;

$R_1$ and $R_2$, which are identical or different, represent:
  an optionally substituted hydrocarbon-based chain, the said chain is a saturated linear $C_1$-$C_{30}$ or branched $C_3$-$C_{30}$ or cyclic $C_3$-$C_7$ chain; the said hydrocarbon-based chain is optionally interrupted with:
    i) one or more heteroatoms such as —O—, —N($R_6$)— or —S—,
    ii) one or more groups —S(O)—, —S(O)$_2$—, —C(O)—, —$N^+$($R_6$)($R_7$)—, or combinations of i) and ii), particularly —N($R_6$)—C(O)—, C(O)—N($R_6$)—, —N($R_6$)—C(O)—N($R_7$)— or —S—S— and/or optionally
    iii) a saturated or unsaturated 3- to 6-membered carbon-based ring optionally substituted with one or more identical or different radicals chosen especially from hydroxyl (OH) and amino (—NRR');
  a divalent chain -Cycl-Alk-Cycl'- with:
    Cycl and Cycl', which may be identical or different, preferentially identical, representing a cyclic hydrocarbon-based chain, particularly a $C_5$-$C_6$ cycloalkylene, such as cyclohexylene or cyclopentylene, and
    Alk representing an optionally substituted ($C_1$-$C_1$) alkylene chain; which is preferentially unsubstituted;
  an optionally substituted hydrocarbon-based chain, the said chain is a saturated linear $C_2$-$C_{30}$ or branched $C_3$-$C_{30}$ or cyclic $C_3$-$C_7$ chain; the said hydrocarbon-based chain is optionally interrupted with:
    i) one or more heteroatoms such as —O—, —N($R_6$)— or —S—,
    ii) one or more groups —S(O)—, —S(O)$_2$—, —C(O)—, —$N^+$($R_6$)($R_7$)—, or combinations of i) and ii), particularly —N($R_6$)—C(O)—, —C(O)—N($R_6$)—, —N($R_6$)—C(O)—N($R_7$)— or —S—S— and/or optionally
    iii) a 3- to 6-membered saturated or unsaturated carbon-based ring optionally substituted with one or more identical or different radicals chosen especially from hydroxyl (OH) and amino (—NRR');

$R_1$ and/or $R_2$ may also be substituted with one or more radicals chosen from (E) and (F):

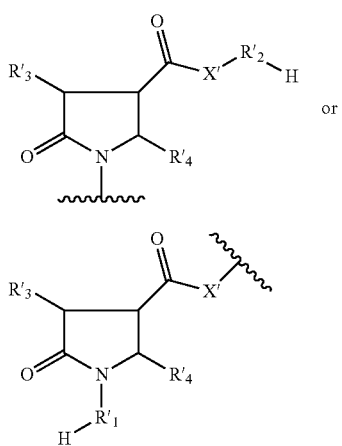

(E)

or (F)

in which formulae (E) and (F):
X' represents an oxygen atom —O— or —N($R_5$)— with $R_5$ as defined previously;
$R'_1$, and $R'_2$, which may be identical or different, being as defined for $R_1$ and $R_2$, but cannot be substituted with the radicals (E) or (F):

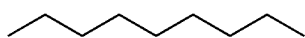

representing the point of attachment of the radicals (E) and (F) to the rest of the molecule;

$A_1$ and $A_2$, which may be identical or different, representing: a hydrogen atom, or a group chosen from a) —OH, b) —SH, c) —NRR'; d) —O—P(O)(OH)$_2$; e) —O—S(O)$_2$OH; f) —S(O)$_2$OH; g) —C(O)OH; h) saturated or unsaturated 3- to 6-membered (hetero)cycle optionally substituted with one or more identical or different radicals chosen from (hydroxy)($C_1$-$C_6$)alkyl, hydroxyl and —NRR', the said (hetero)cycle possibly being cationic; i) —N+($R_7$)($R_8$)($R_9$): j) RR'N—C(=NR")—N(R)—, particularly

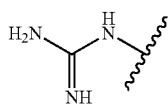

and
k) a radical of formula (G) or (H):

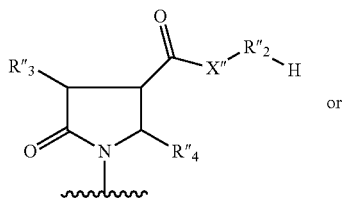

(G)

or

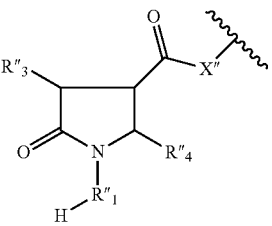

(H)

in which formulae (G) and (H):
X" represents an oxygen atom —O— or —N($R_5$)— with $R_5$ as defined previously;
$R"_1$, and $R"_2$, which may be identical or different, are as defined for $R'_1$, and $R'_2$ previously;
with $A_1$ and $A_2$ not simultaneously representing a radical (G) or (H);

$R_3$, $R_4$, $R'_3$, $R'_4$, $R"_3$ and $R"_4$, which may be identical or different, representing a hydrogen atom or a linear $C_1$-$C_{12}$ or branched $C_3$-$C_{12}$ alkyl chain;

$R_6$ represents a hydrogen atom or a linear ($C_1$-$C_{20}$)alkyl or branched ($C_3$-$C_{20}$) alkyl group, optionally substituted with a radical (G) or (H);

$R_7$, $R_8$ and $R_9$, which may be identical or different, representing a hydrogen atom or a group ($C_1$-$C_6$)alkyl optionally substituted with one or more hydroxyl groups;

R, R' and R", which may be identical or different, representing a hydrogen atom or a group ($C_1$-$C_{18}$)alkyl optionally substituted with one or more hydroxyl groups;

it being understood that when $A_1$ and/or $A_2$ and/or $R_1$ and/or $R_2$ and/or $R_5$ contain or denote a cationic group, the electrical neutrality of the compounds of formula (I) is ensured by an anionic counterion or a mixture of anionic counterions such as cosmetically acceptable organic or mineral anions, particularly acetate, lactate, tartrate, citrate, halide (Cl⁻, Br⁻), $SO_4^{2-}$, $MeSO_4^-$, $EtSO_4^-$, ethosulfate, hydrogen sulfate, para-toluenesulfonate or mesylate.

Another subject of the invention is the derivative of formula (Ia) chosen from compounds 1 to 65:

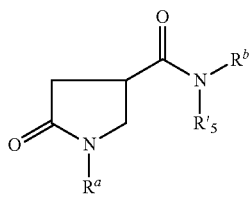

(Ia)

And also the organic or mineral acid salts thereof, optical isomers thereof: stereoisomers, enantiomers and diastereoisomers, and the solvates thereof such as hydrates;
in which formula (Ia):
$R'_5$ representing a hydrogen atom or a linear or branched ($C_1$-$C_{20}$)alkyl and particularly ($C_1$-$C_6$)alkyl group;
$R^a$ represents a linear or branched ($C_2$-$C_{30}$)alkyl and preferentially linear ($C_2$-$C_{20}$)alkyl group;
$R^b$ represents a linear or branched ($C_1$-$C_{20}$)alkyl and preferentially branched ($C_3$-$C_{10}$)alkyl group; preferentially, $R_a$ and $R_b$ are linear;

it being understood that $R_a$ cannot represent a branched chain chosen from isopropyl —CH(CH$_3$)$_2$, n-butyl —(CH$_2$)$_3$—CH$_3$, tert-butyl —C(CH$_3$)$_3$, isopentyl —CH$_2$—CH$_2$—CH(CH$_3$)$_2$, and —CH$_2$—CH(CH$_2$CH$_3$)-n-Bu, and that the compounds of formula (Ia) cannot represent the following compounds:
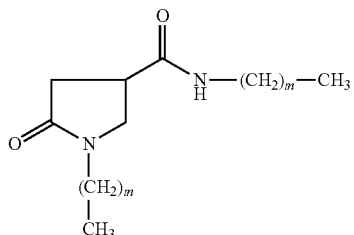
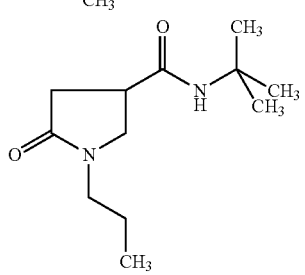
with m=1, 4, 7, 11 and 17;
and compounds 1 to 65:
1
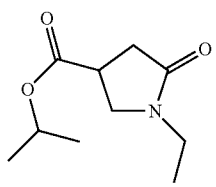
2
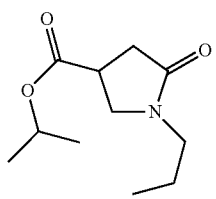
3
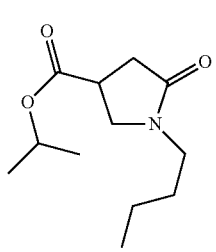
4
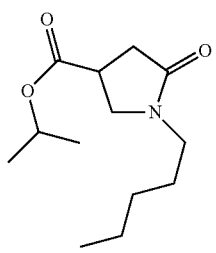
5
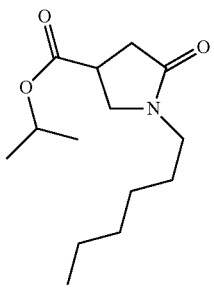
6
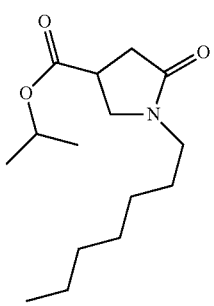
7
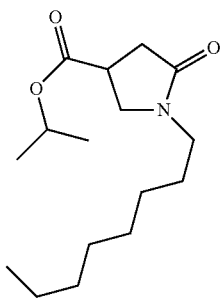
8
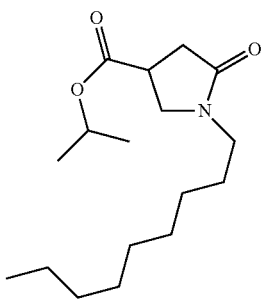
9
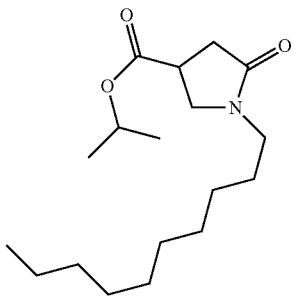

10
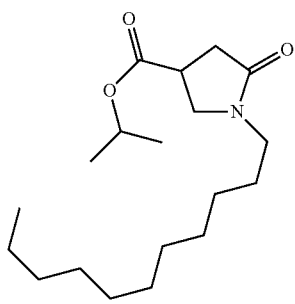
11
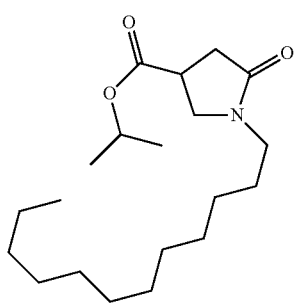
12
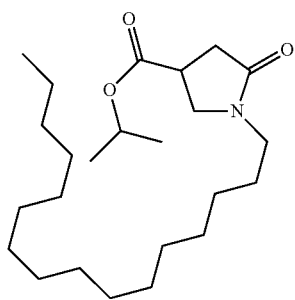
13
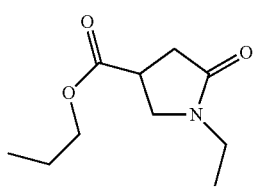
14
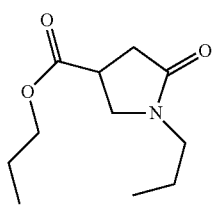
15
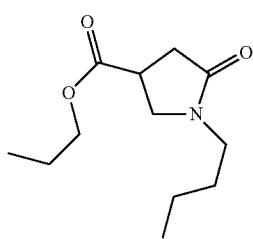
16
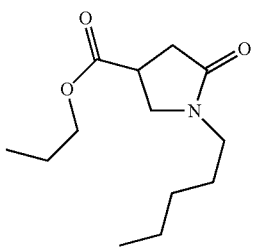
17
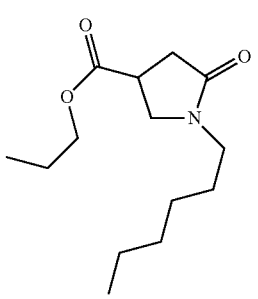
18
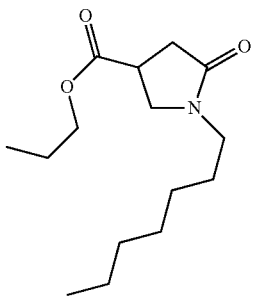
19
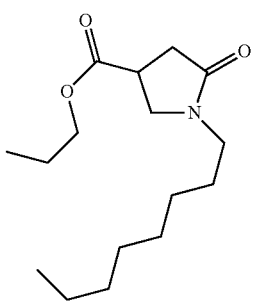
20
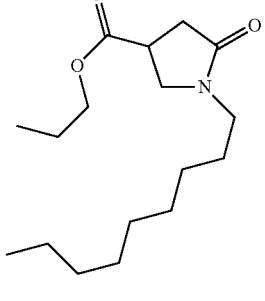

21
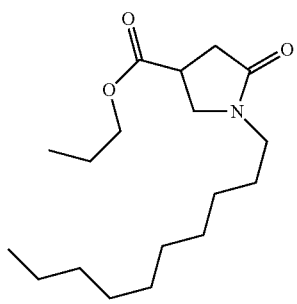
22
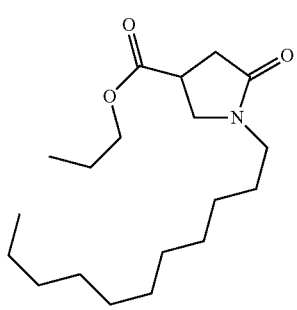
23
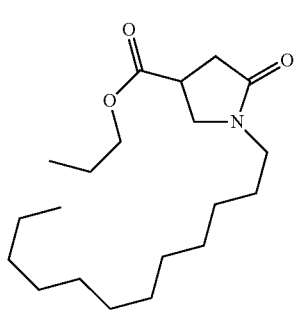
24
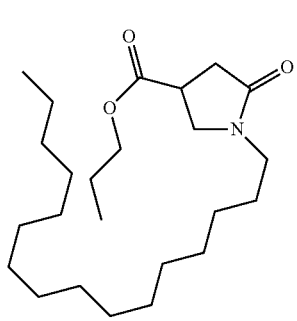
25
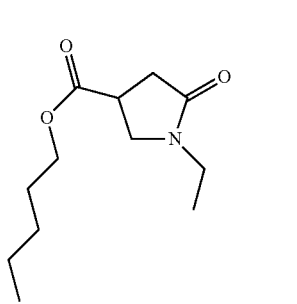
26
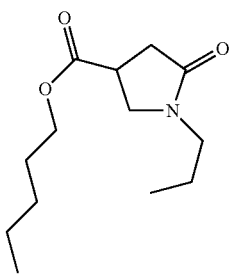
27
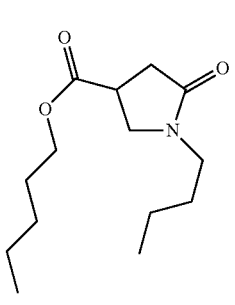
28
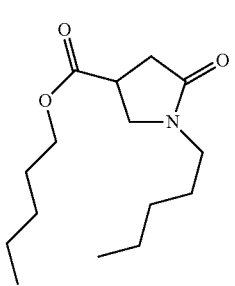
29
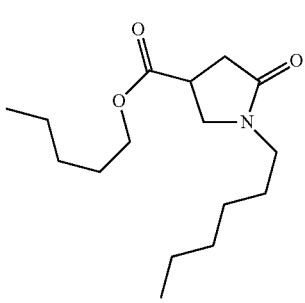
30
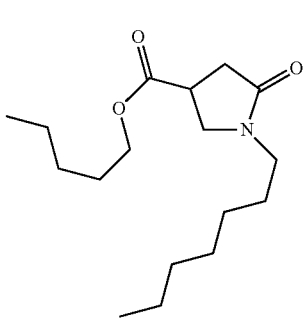

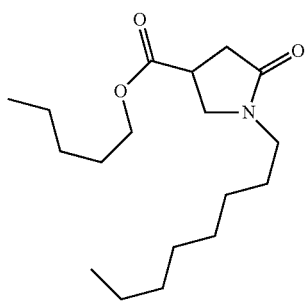
31
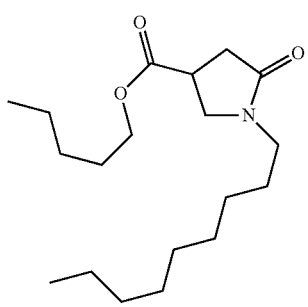
32
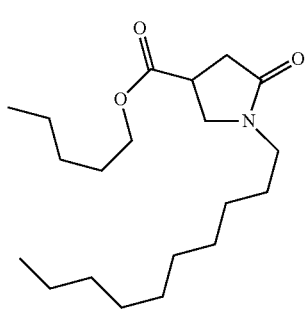
33
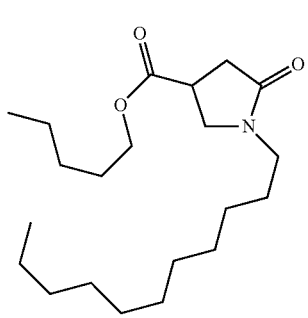
34
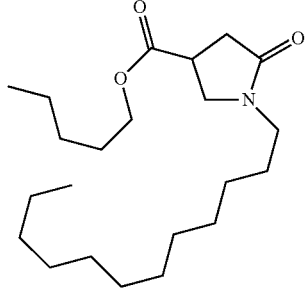
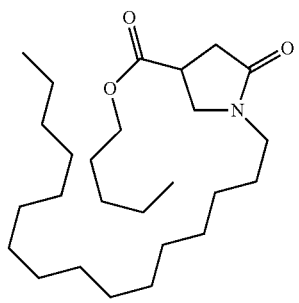
36
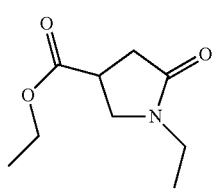
37
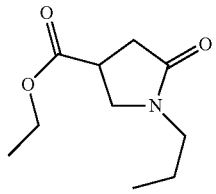
38
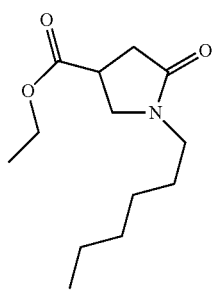
39
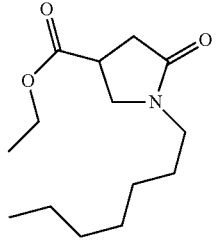
40
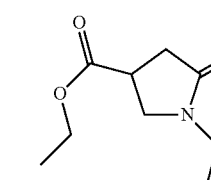
41
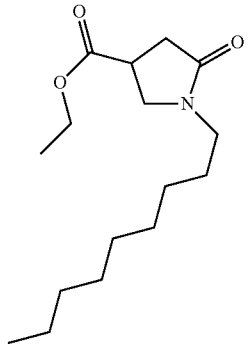

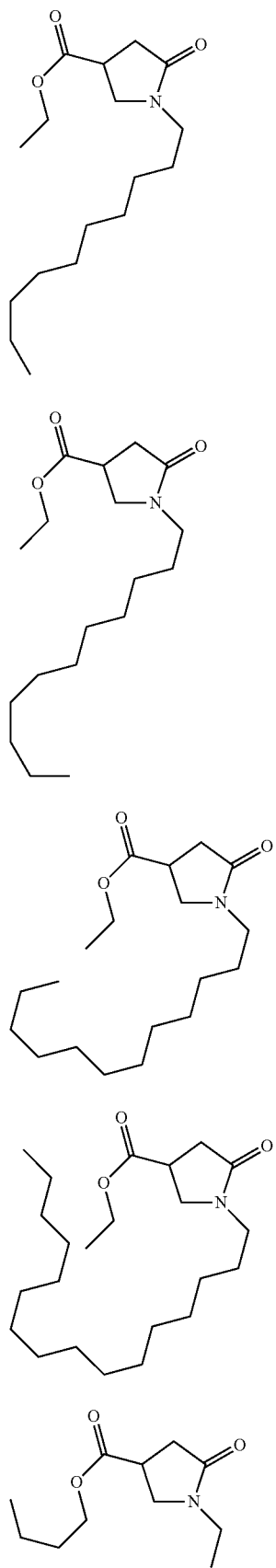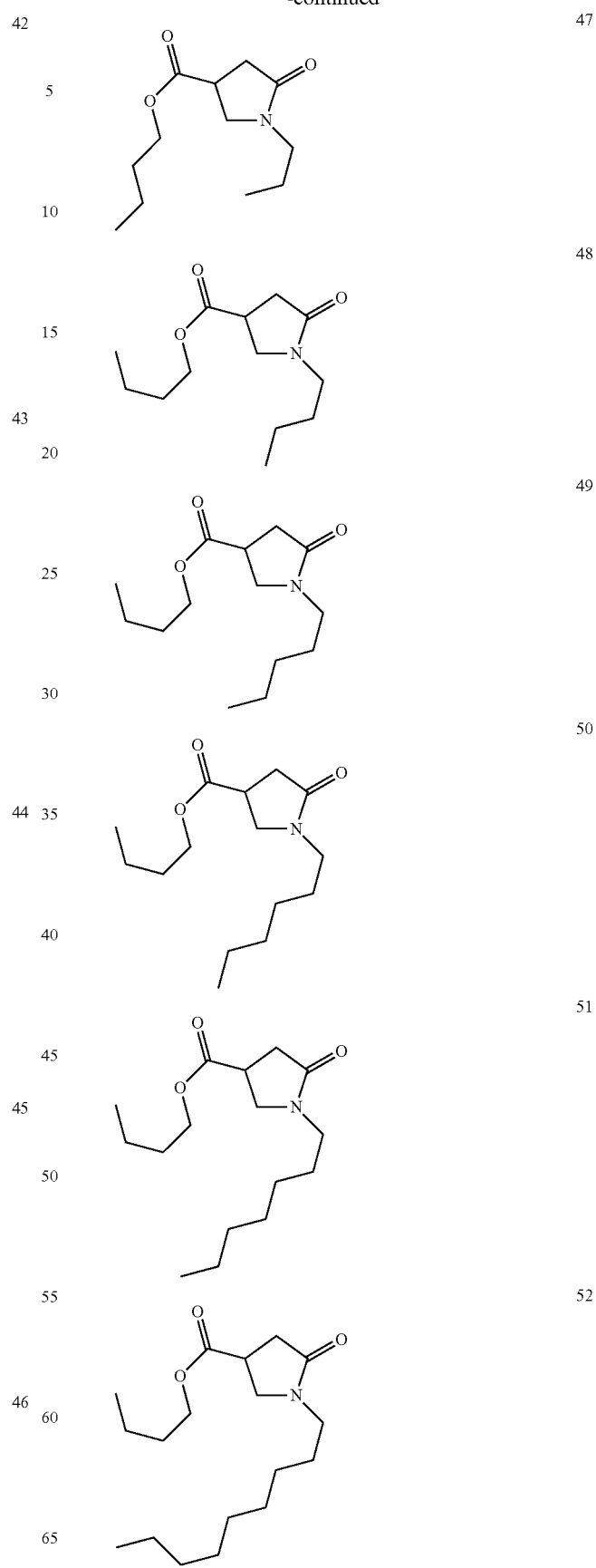

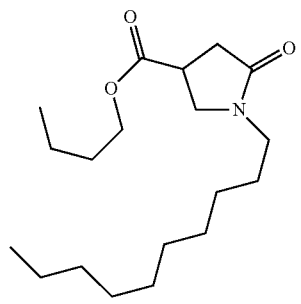
53
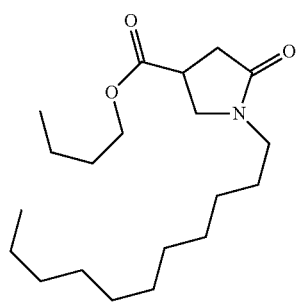
54
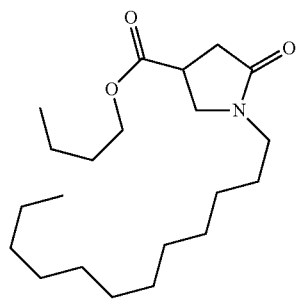
55
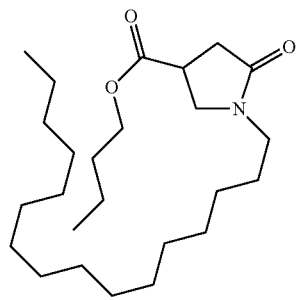
56
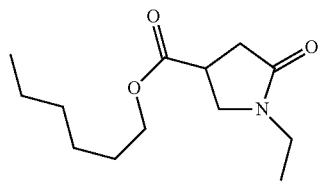
57
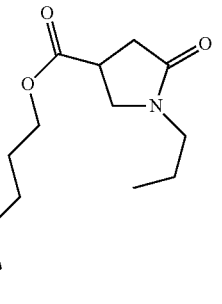
58
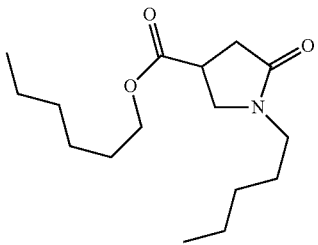
59
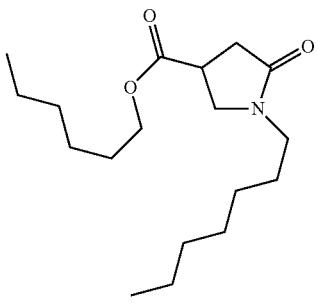
60
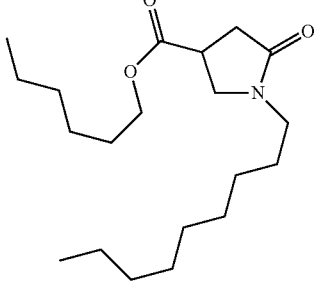
61
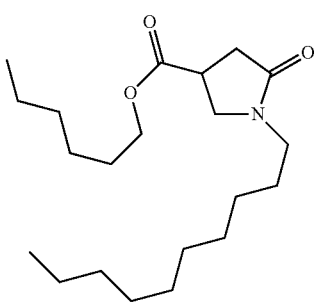
62

-continued

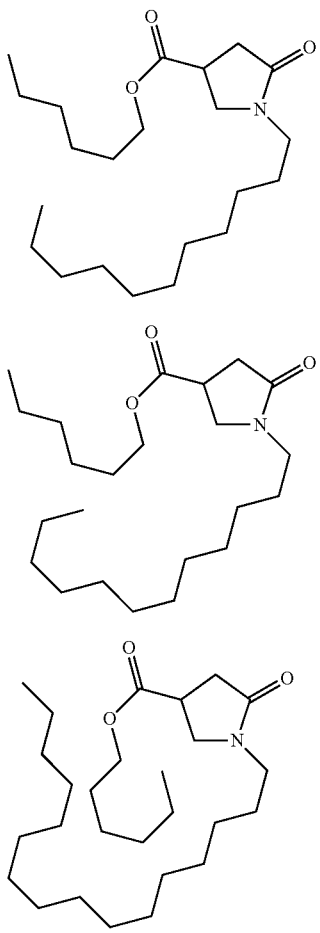

Compounds 1 to 65, and also the organic or mineral acid salts thereof, optical isomers thereof: stereoisomers or enantiomers and diastereoisomers, and the solvates thereof such as hydrates.

Another subject of the invention is a process for dyeing keratin materials using the cosmetic composition as defined previously.

A subject of the invention is similarly the use of the said pyrrolidone combined with a pigment and/or a direct dye that are sparingly soluble or insoluble in aqueous-alcoholic supports, for dyeing keratin materials, and especially the use of the said pyrrolidone for improving the colour uptake onto keratin fibres of the said pigments and direct dyes that are sparingly soluble or insoluble in aqueous-alcoholic supports.

The use of the composition according to the invention, as defined previously, makes it possible to overcome drawbacks especially in terms of solubility, colour uptake, selectivity, power or chromaticity, while at the same time being particularly resistant to successive shampooing, or to sweat.

For the purposes of the present invention, and unless otherwise indicated:

The "saturated carbon-based rings" are cycloalkyls such as cyclopropyl, cyclobutyl, cyclopentyl and cyclohexyl; preferentially cyclohexyl;

The "unsaturated carbon-based rings" are $C_3$ to $C_6$ rings comprising from 1 to 3 conjugated or unconjugated double bonds, particularly of the cycloalkylene type such as hexylenyl, or aryl such as phenyl;

The "heterocycles" are hydrocarbon-based rings in which one or more of the carbon atoms have been replaced with one or more heteroatoms such as oxygen, sulfur or nitrogen atoms, the said heterocycle possibly being saturated; they are heterocycloalkyls that are preferentially 3- to 6-membered, such as morpholinyl, thiomorpholinyl, piperidyl, piperazinyl, pyrrolidinyl, tetrahydrofuryl or azepanyl, preferentially pyrrolidinyl and morpholinyl;

or alternatively the said heterocycle is unsaturated and comprises from 1 to 3 conjugated or unconjugated double bonds, particularly of heterocycloalkenyl or heteroaryl type as defined below;

an "aryl" radical represents a fused or non-fused monocyclic or polycyclic group containing from 6 to 22 carbon atoms, and in which at least one ring is aromatic; preferentially, the aryl radical is a phenyl, biphenyl, naphthyl, indenyl, anthracenyl or tetrahydronaphthyl;

a "heteroaryl radical" represents a fused or nonfused, optionally cationic, 5- to 22-membered monocyclic or polycyclic group, comprising from 1 to 6 heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthylyl and the ammonium salt thereof;

The "(hetero)cycles" are either saturated or unsaturated heterocycles or carbon-based rings as defined previously;

The "cyclic hydrocarbon-based chain" is a divalent 3- to 7-membered chain, which may be saturated or unsaturated with 1 to 3 unsaturations, especially such as cycloalkylene or arylene, such as those chosen from:

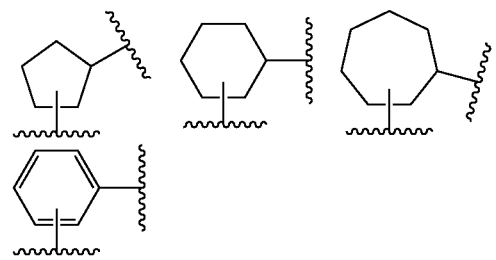

The aromatic part of a (hetero)cyclic radical may be substituted with a substituent borne by a carbon atom, chosen from:

a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
a halogen atom such as chlorine, fluorine or bromine;
a hydroxyl group;
a $C_1$-$C_2$ alkoxy radical;
a $C_2$-$C_4$ (poly)hydroxyalkoxy radical;
an amino radical;
nitro;
a 5- or 6-membered heterocycloalkyl radical;
an optionally cationic 5- or 6-membered heteroaryl radical, preferentially imidazolium, optionally substituted with a ($C_1$-$C_4$)alkyl radical, preferentially methyl;
an amino radical substituted with one or two identical or different $C_1$-$C_6$ alkyl radicals, optionally bearing at least:
  i) a hydroxyl group,
  ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other heteroatom identical to or different from nitrogen,
  iii) a quaternary ammonium group for which R', R" and R'", which may be identical or different, represent a hydrogen atom or a $C_1$-$C_4$ alkyl group; and $M^-$ represents the organic or mineral counterion, such as halide,
  iv) or an optionally cationic 5- or 6-membered heteroaryl radical, preferentially imidazolium, optionally substituted with a ($C_1$-$C_4$)alkyl radical, preferentially methyl;
an acylamino radical (—NR—C(O)R') in which the radical R is a hydrogen atom or a $C_1$-$C_4$ alkyl radical optionally bearing at least one hydroxyl group and the radical R' is a $C_1$-$C_2$ alkyl radical;
a carbamoyl radical ($(R)_2$N—C(O)—) in which the radicals R, which may be identical or different, represent a hydrogen atom or a $C_1$-$C_4$ alkyl radical optionally bearing at least one hydroxyl group;
a carboxylic acid or ester radical, (—O—C(O)R') or (—C(O)OR'), in which the radical R is a hydrogen atom or a $C_1$-$C_4$ alkyl radical optionally bearing at least one hydroxyl group and the radical R' is a $C_1$-$C_2$ alkyl radical;
the carboxylic radical possibly being in acid or salified form (preferably with an alkali metal or a substituted or unsubstituted ammonium);
an alkylsulfonylamino radical (R'S(O)$_2$—NR—) in which the radical R is a hydrogen atom or a $C_1$-$C_4$ alkyl radical optionally bearing at least one hydroxyl group and the radical R' is a $C_1$-$C_4$ alkyl radical or a phenyl radical;
an aminosulfonyl radical ($(R)_2$N—S(O)$_2$—) in which the radicals R, which may be identical or different, represent a hydrogen atom or a $C_1$-$C_4$ alkyl radical optionally bearing at least one hydroxyl group;
a cyano group (CN);
a polyhaloalkyl group, preferentially trifluoromethyl (CF$_3$);
the non-aromatic part of a cyclic or heterocyclic radical may be substituted with at least one substituent borne by a carbon atom, chosen from the groups:
hydroxyl,
$C_1$-$C_4$ alkoxy or $C_2$-$C_4$ (poly)hydroxyalkoxy,
alkylcarbonylamino ((RCO—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other heteroatom identical to or different from nitrogen;
alkylcarbonyloxy ((RC(O)—O—) in which the radical R is a $C_1$-$C_4$ alkyl radical, an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other heteroatom identical to or different from nitrogen;
alkoxycarbonyl ((RO—C(O)—) in which the radical R is a $C_1$-$C_4$ alkyl radical, an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other heteroatom identical to or different from nitrogen;
a compound containing one or more cationic groups, which means that the said compound comprises at least one cationic group other than an acid salt, particularly the said compound comprises at least one group chosen from tri($C_1$-$C_6$)alkylammonium, guanidinium —N$^+$($R_6$)($R_7$)—; cationic (hetero)cycle or heteroaryl; —N$^+$($R_7$)($R_8$)($R_9$) as defined previously;
a cyclic or heterocyclic radical, or a non-aromatic portion of an aryl or heteroaryl radical, may also be substituted with one or more oxo groups;
a hydrocarbon-based chain is unsaturated when it comprises one or more double bonds and/or one or more triple bonds that may be conjugated or unconjugated; preferentially, it comprises from 1 to 3 double bonds;
a "salt of an organic or mineral acid" is chosen, for example, from a solvent derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid P(O)(OH)$_3$; xiii) acetic acid CH$_3$C(O)OH; xiv) triflic acid CF$_3$SO$_2$OH; and xv) tetrafluoroboric acid HBF$_4$;
an "organic or mineral base salt" is chosen, for example, from a salt derived from mineral bases such as i) sodium hydroxide NaOH, ii) potassium hydroxide KOH, or from organic bases such as iii) aqueous ammonia; iv) amines and hydroxyamines such as (tri)($C_1$-$C_6$)alkylamine or (tri)hydroxy($C_1$-$C_6$)alkylamine, and also salts thereof derived from alkali metals and alkaline-earth metals;

an "anionic counterion" is an anion or an anionic group associated with the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulphates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$; xiii) phosphate; xiv) acetate; xv) triflate; and xvi) borates such as a tetrafluoroborate;

an "alkyl" radical is a saturated, linear or branched hydrocarbon-based radical, containing from 1 to 6 carbon atoms and particularly from 1 to 3 carbon atoms, such as the methyl or ethyl radical;

an "alkoxy" radical is an "alkyl-oxy" alkyl-O— radical in which the alkyl part is as defined previously;

the alkyl, alkoxy or (hetero)cycloalkyl radicals followed by "optionally substituted with . . . " means that the said radicals may have one or more hydrogen atoms replaced with one or more substituents in question, particularly one or two substituents in question;

the term "optionally substituted" attributed to the alkyl radical, the hydrocarbon-based chain or the alkylene chain means that the said alkyl radicals or hydrocarbon-based chain may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming with the nitrogen atom that bears them a 5- to 7-membered heterocycle optionally comprising another heteroatom identical to or different from nitrogen; v) or a quaternary ammonium group —N$^+$R'R''R''', M$^-$ for which R', R'' and R''', which may be identical or different, represent a hydrogen atom or a $C_1$-$C_4$ alkyl group, or alternatively —N$^+$R'R''R''' forms a heterocycle of heteroaryl type such as imidazolium optionally substituted with a $C_1$-$C_4$ alkyl group, and M$^-$ represents the counterion of the organic or mineral acid or of the corresponding halide.

Compounds of Formula (I) or (Ia):

According to one particular embodiment of the invention, the compounds of formula (I) are such that X, X' and X" represent an oxygen atom or an amino group —N(R$_5$)—, particularly R$_5$=H or a group ($C_1$-$C_6$)alkyl.

According to another particular embodiment of the invention, in the compounds of formula (I) the radicals R$_3$, R'$_4$, R''$_3$, R''$_4$ represent a hydrogen atom.

One particularly advantageous variant of the invention concerns the compounds of formula (I) in which R$_1$ denotes a linear $C_1$-$C_{20}$ or branched $C_3$-$C_{20}$ saturated hydrocarbon-based chain optionally interrupted with one or more heteroatoms such as O, S or groups —N(R$_6$)—, —N$^+$(R$_6$)(R$_7$)—, —N(R$_6$)—C(O)—, —C(O)—N(R$_6$)—, —N(R$_6$)—C(O)—N(R$_7$)— or —S—S— and/or optionally substituted with one or more identical or different radicals chosen from hydroxyl (OH) and —NR$_6$R.

Particularly, the compound of formula (I) is such that the radical R$_6$ represents a group ($C_1$-$C_6$)alkyl optionally substituted with a radical (G) as defined previously and R$_7$ represents a hydrogen atom or a group ($C_1$-$C_6$)alkyl.

Preferentially, R''$_2$ represents a group ($C_1$-$C_4$)alkylene.

According to another advantageous variant of the invention, the compound of formula (I) is such that R$_2$ denotes a linear $C_1$-$C_{12}$ or branched $C_3$-$C_{12}$ saturated hydrocarbon-based chain optionally interrupted with one or more heteroatoms such as O, S or groups —N(R$_6$)—, —N$^+$(R$_6$)(R$_7$)—, —N(R$_6$)—C(O)—, —C(O)—N(R$_6$)—, —N(R$_6$)—C(O)—N(R$_7$)— or —S—S— and/or optionally substituted with one or more identical or different radicals chosen from hydroxyl (OH) and —NRR', preferentially, R and R' represent a hydrogen atom or a group $C_1$-$C_5$ alkyl.

Preferentially, the compound of formula (I) is such that:
A1 represents:
a hydrogen atom,
a radical —OH,
a radical —S(O)$_2$OH
a radical NRR',
a radical —O—P(O)OH$_2$
a radical —O—S(O)$_2$OH
a radical —C(O)OH,
a saturated or unsaturated 4- to 6-membered (hetero)cycle, this (hetero)cycle possibly being cationic,
a radical of formula: —N$^+$(R$_7$)(R$_8$)(R$_9$) or (G)

According to one preferred mode of the invention, the compound of formula (I) contains only one 2-pyrrolidinone units functionalized in position 4 with an ester or amide, i.e. it does not contain any units (E), (F), (G) or (H).

According to another preferred mode of the invention, the compound of formula contains two or three 2-pyrrolidinone units functionalized in position 4 with an ester or amide, preferentially of unit (E) and/or (G). More particularly, R$_1$ represents a divalent chain -alk-T-alk'- with
T representing:
either a covalent bond σ$_1$,
or a heteroatom such as O,
or a group —N(R'$_6$)— with R'$_6$ representing a hydrogen atom or a group ($C_1$-$C_6$)alkyl or -alk'-(E);
or a divalent group —X$_a$-alk''-X$_b$— with X$_a$ and X$_b$, which may be identical or different, representing a heteroatom such as 0 or a group NH;
alk, alk' and alk'', which may be identical or different, representing a group ($C_1$-$C_6$) alkylene, preferentially alk, alk' and alk'' are identical and represent an ethylene or propylene chain;
A$_1$ represents a radical (G) as defined previously.

According to one preferred embodiment of the invention, the compounds of formula (I) contain one or more cationic groups.

According to one preferred variant of the invention, the compound of formula (I) containing R$_7$, R$_7$, R$_9$ represent, independently of each other, a group ($C_1$-$C_4$)alkyl.

Preferentially, the compound of formula (I) is such that:
A2 represents:
a hydrogen atom,
a hydroxyl radical,
a saturated or unsaturated 4- to 6-membered (hetero)cycle, this (hetero)cycle possibly being cationic,
a radical of formula: —N$^+$(R$_7$)(R$_8$)(R$_9$).

More particularly, R$_2$ represents a saturated $C_1$-$C_{10}$ hydrocarbon-based chain optionally interrupted with one or more oxygen atoms.

According to one particular mode of the invention, R$_2$ represents a saturated hydrocarbon-based chain interrupted with several oxygens such that the said chain is: —[—CH$_2$—CH$_2$]$_n$—O—, with n representing an integer between 1 and 4.

According to one preferred embodiment of the invention, the compound(s) of formula (I) are of formula (I' a):

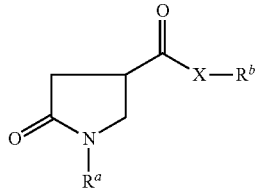

(I'a)

and also the organic or mineral acid salts thereof, optical isomers thereof: stereoisomers, enantiomers and diastereoisomers, and the solvates thereof such as hydrates;

in which formula (Ia):

- X represents an oxygen atom or a divalent amino group $-N(R'_5)-$; with $R'_5$ representing a hydrogen atom or a linear or branched $(C_1-C_{20})$alkyl and particularly $(C_1-C_6)$alkyl group;
- $R^a$ represents a linear or branched $(C_2-C_{30})$alkyl and preferentially linear $(C_2-C_{20})$alkyl group;
- $R^b$ represents a linear or branched $(C_1-C_{20})$alkyl and preferentially branched $(C_3-C_{10})$alkyl group.

According to one particularly advantageous embodiment of the invention, the compounds of formula (I) are such that X=O, $R_3$, $R_4$, $A_1$ and $A_2$ represent a hydrogen atom; and $R_1$ and $R_2$, which may be identical or different, represent a linear $C_1-C_8$ or branched $C_3-C_8$ alkylene group.

Preferentially, the compounds of formula (I) of the invention are chosen from those of the following list:

a

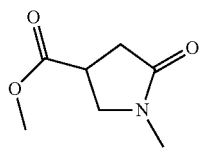

b

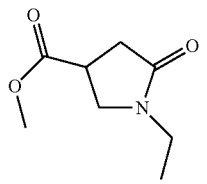

c

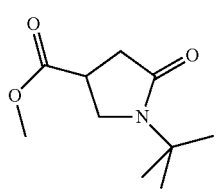

d

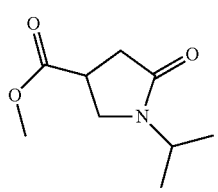

e

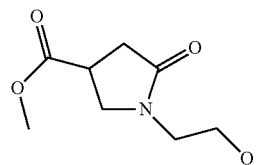

f

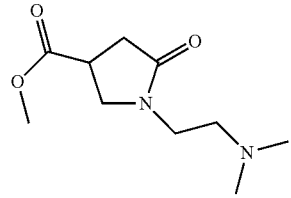

g

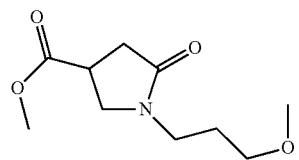

h

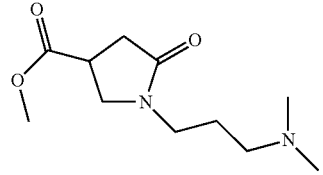

i

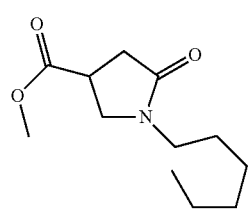

j

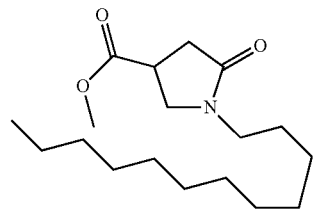

k

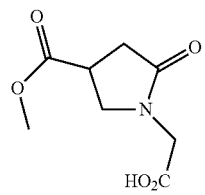

l

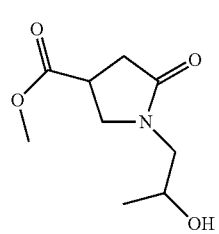

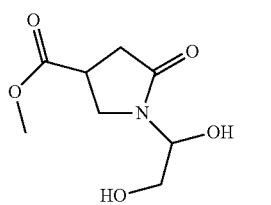
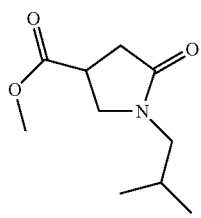
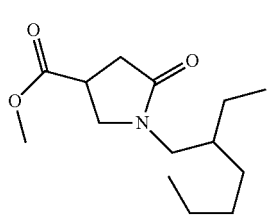
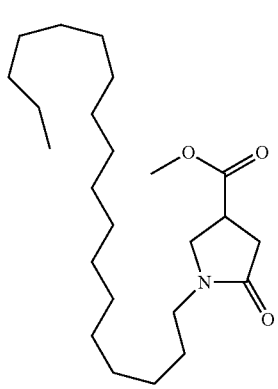
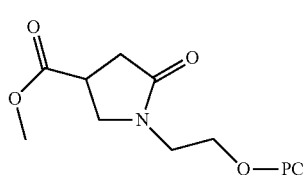
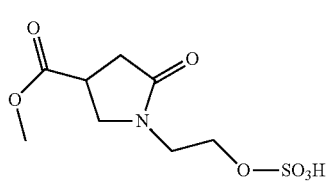
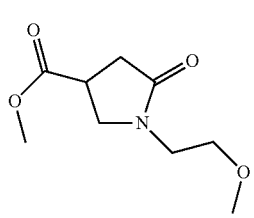
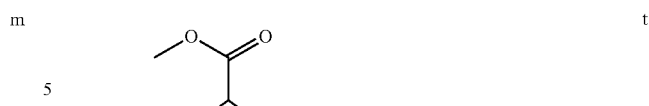
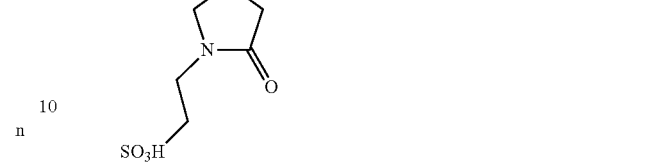
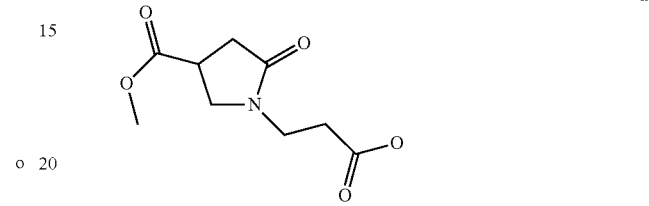
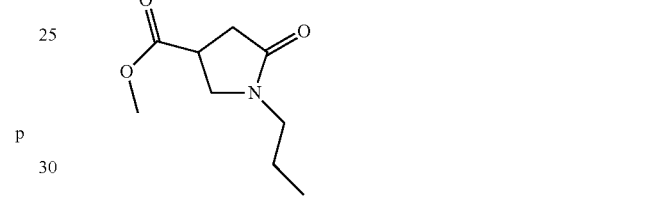
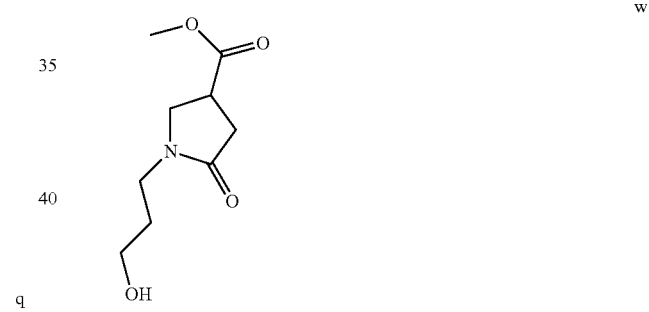
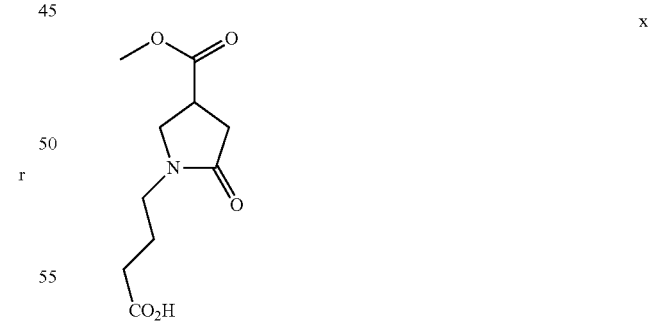
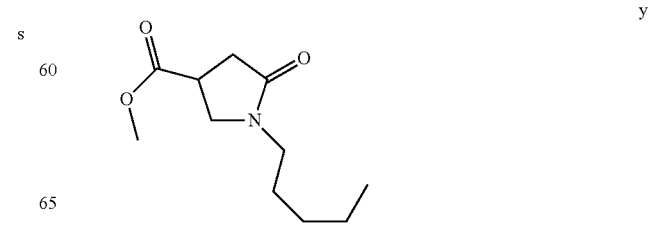

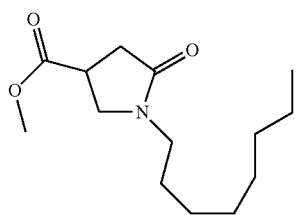
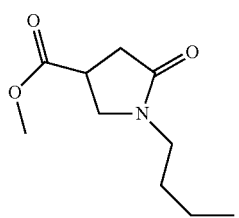
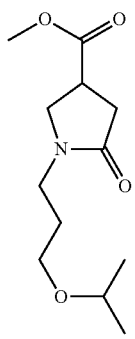
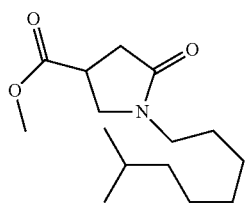
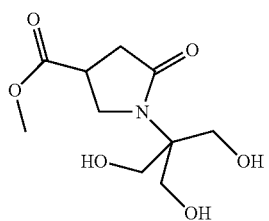
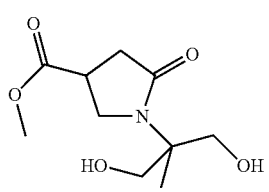
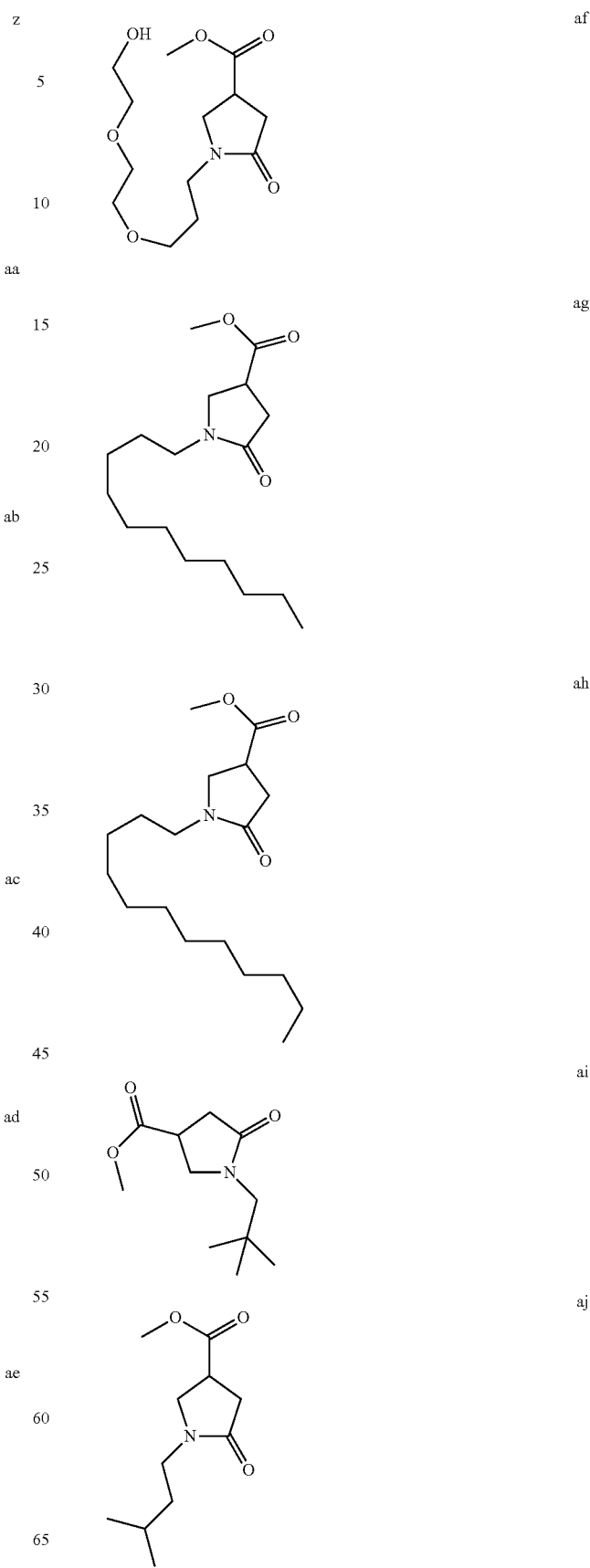

-continued
ak 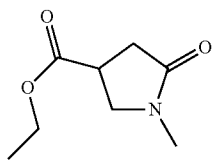
al 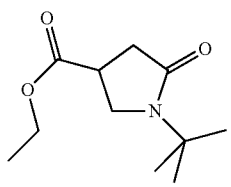
am 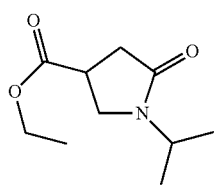
an 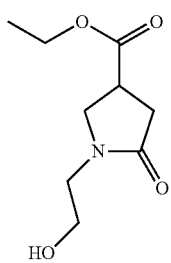
am 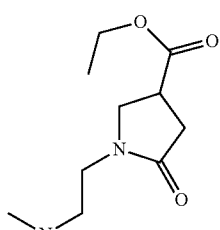
ao 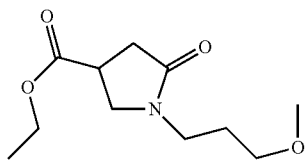
ap 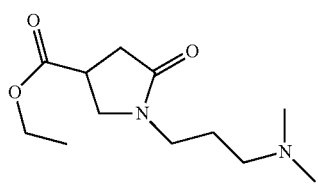
aq 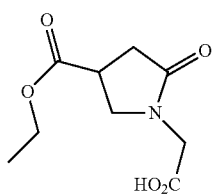
-continued
ar 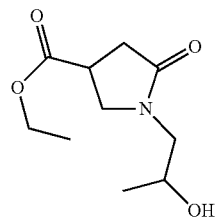
as 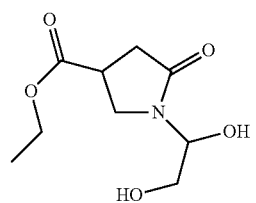
at 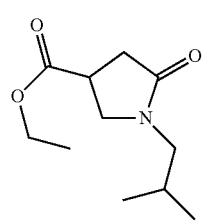
au 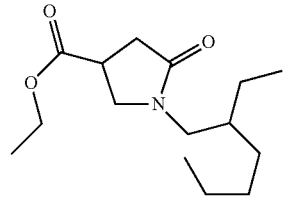
av 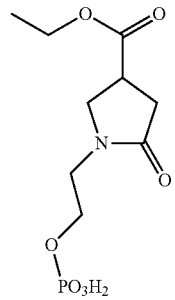
aw 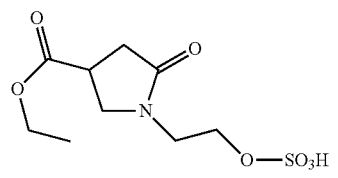
ax 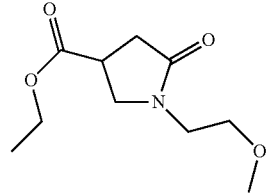

31
-continued
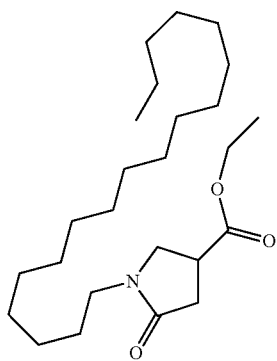
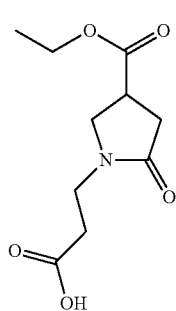
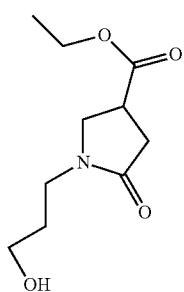
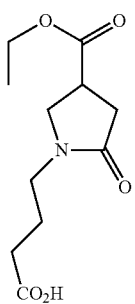
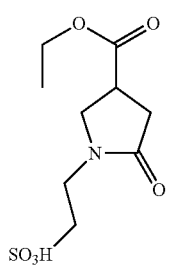
32
-continued
ay
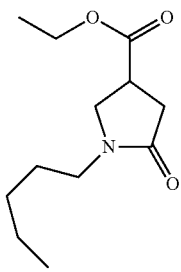
az
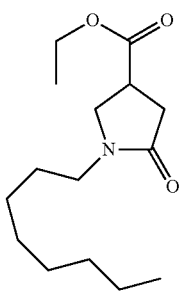
ba
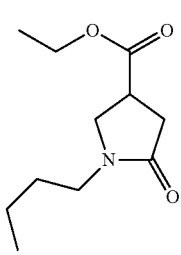
bb
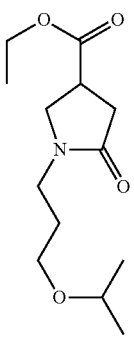
bc
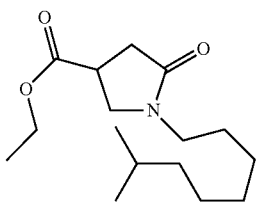
bd
be
bf
bg
bh

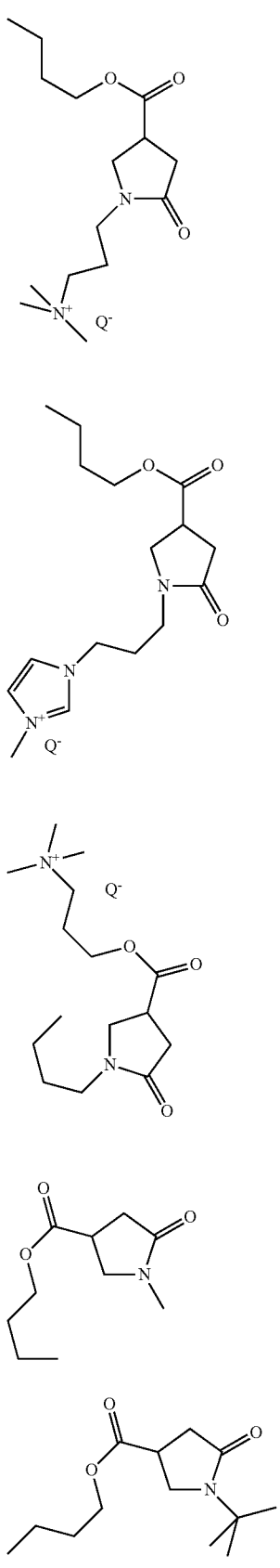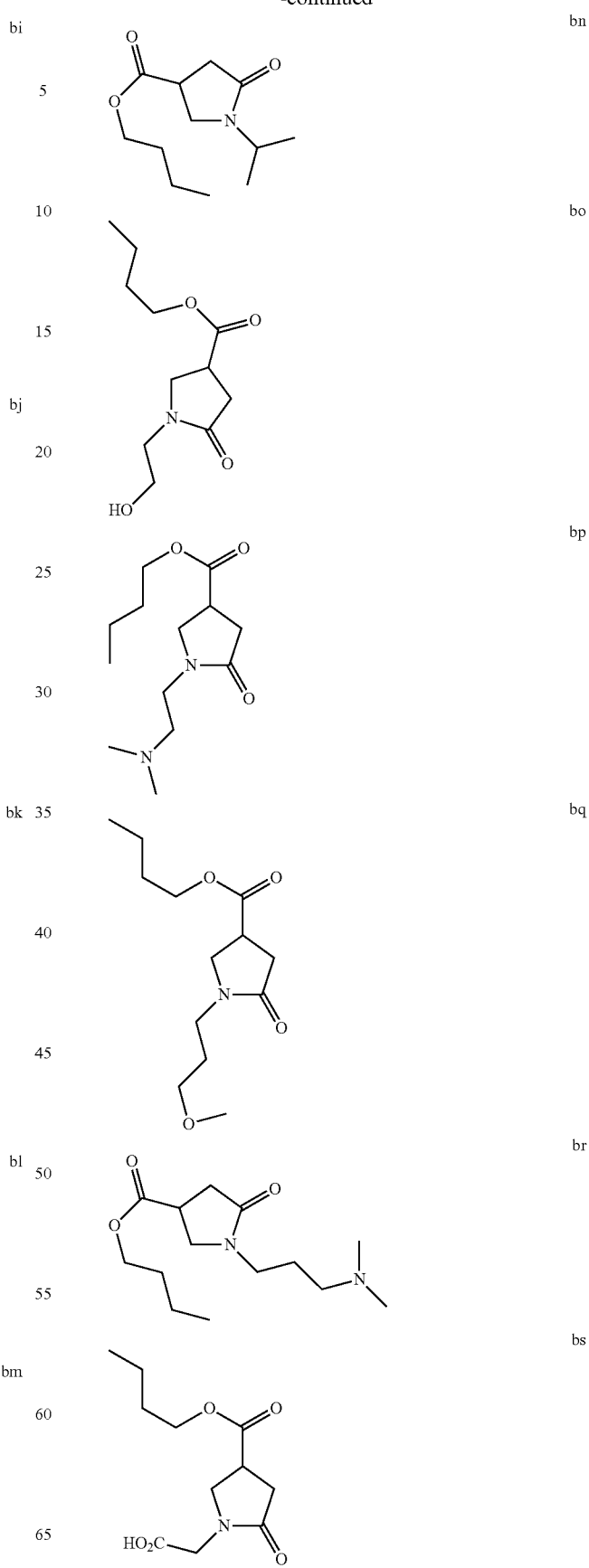

bt 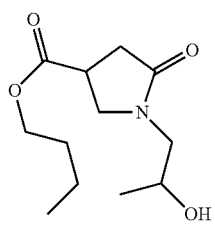
bu 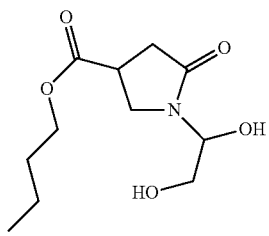
bv 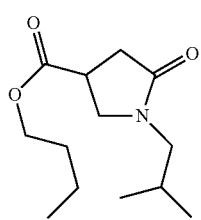
bw 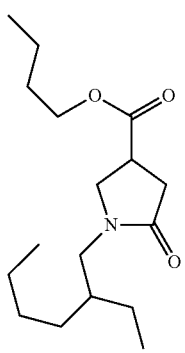
bx 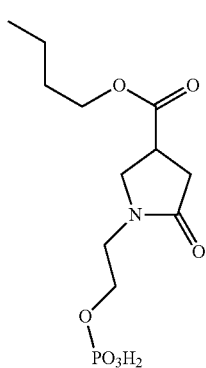
by 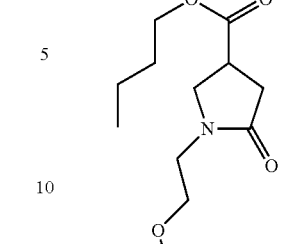
bz 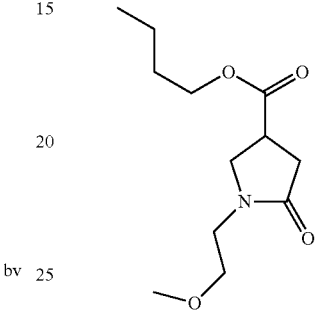
ca 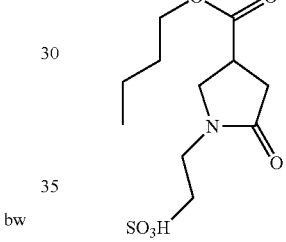
cb 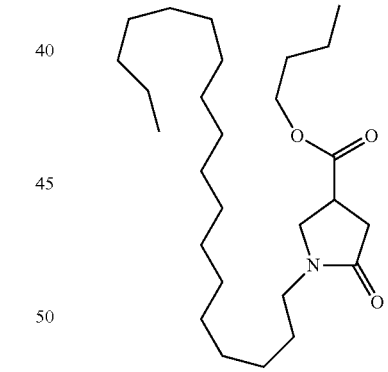
cc 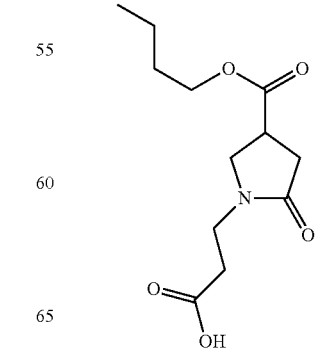

cd
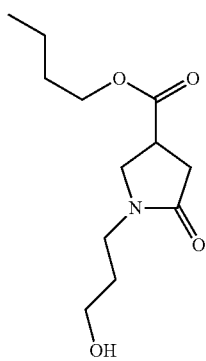
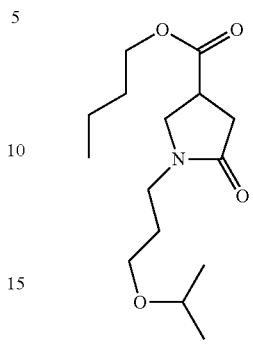
ci
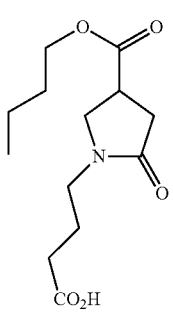
ce
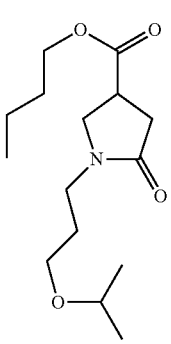
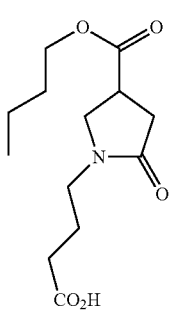
cf
cj
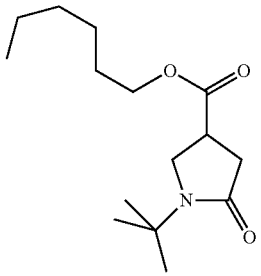
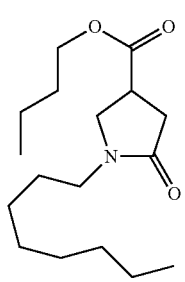
cg
ck
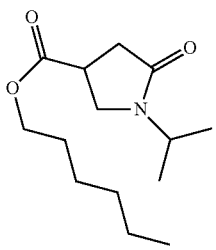
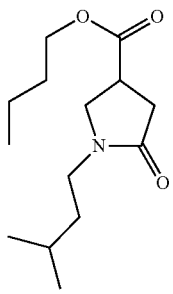
ch
cl
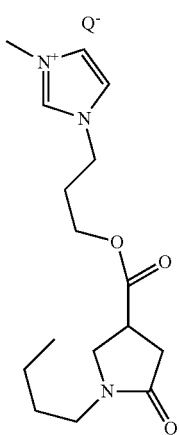

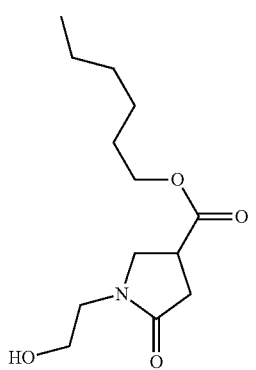 cm
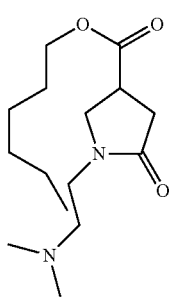 cn
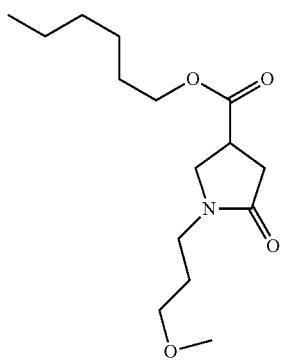 co
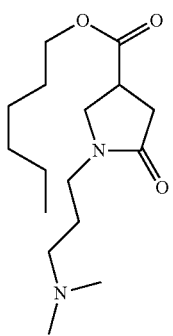 cp
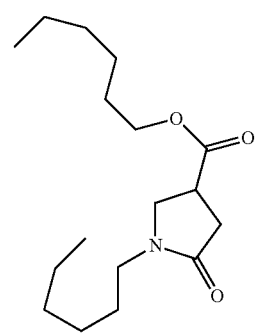 cq
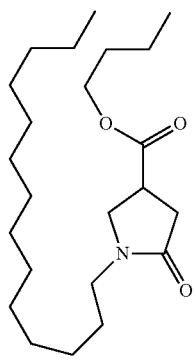 cr
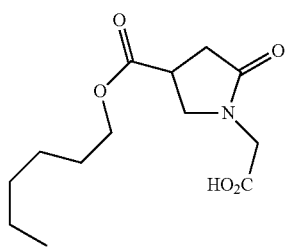 cs
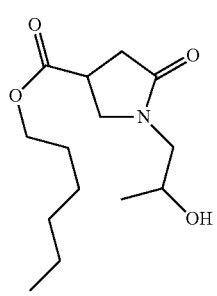 ct
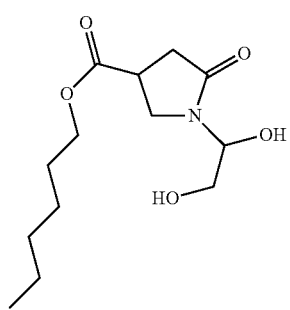 cu

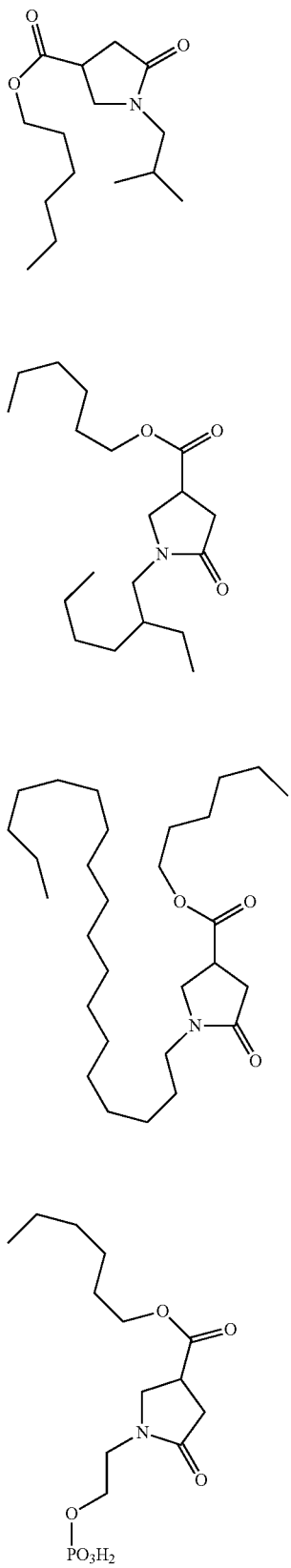
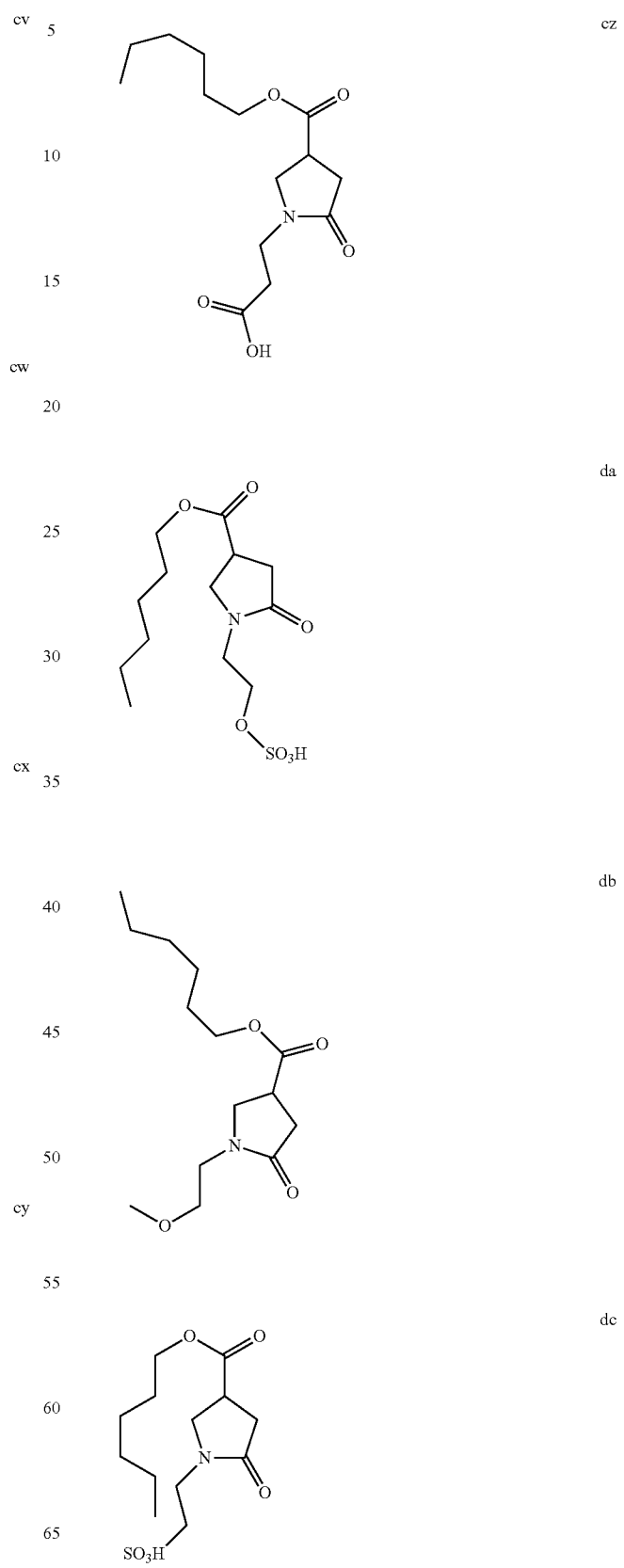

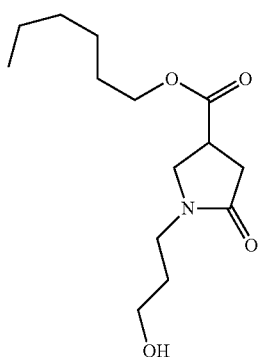
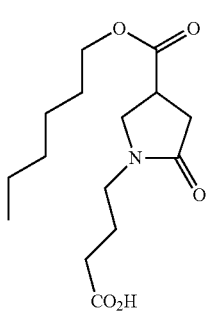
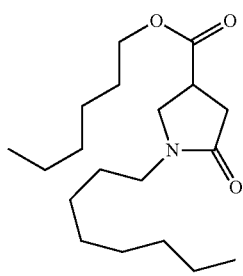
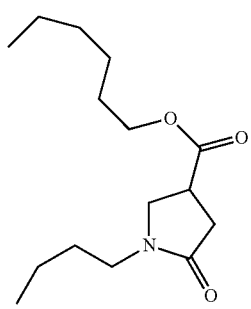
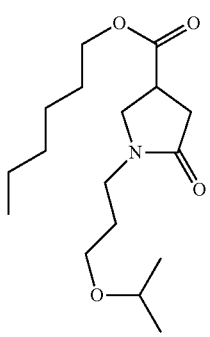
de
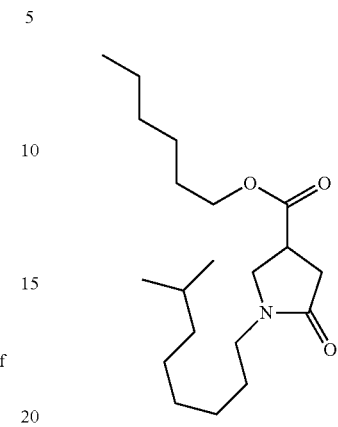
df
dg
dh
di
dj
dk
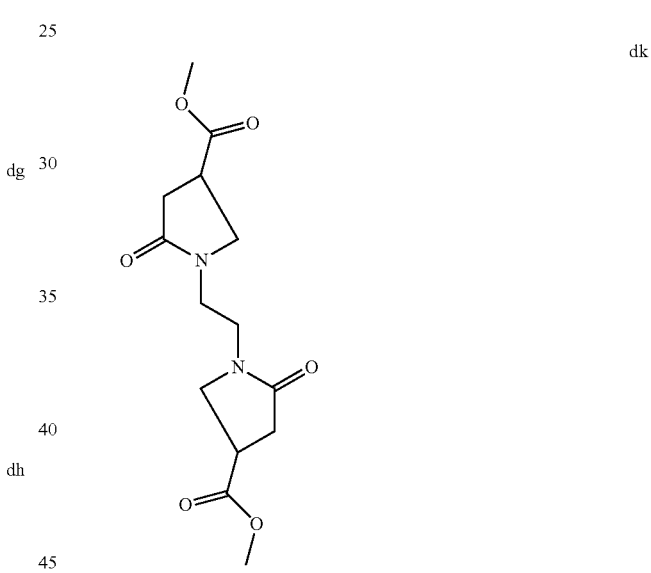
dl
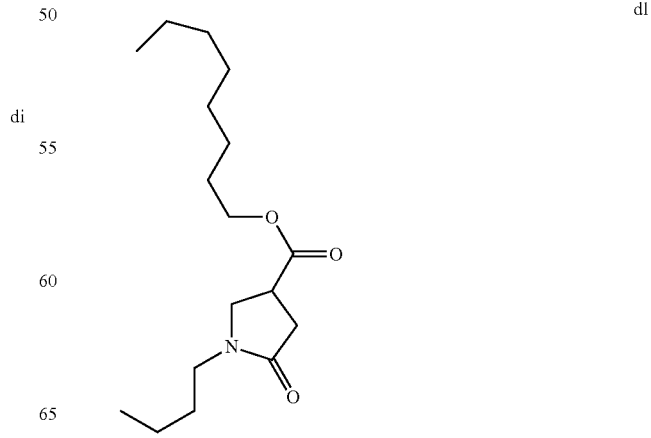

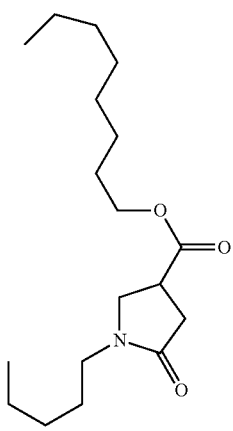
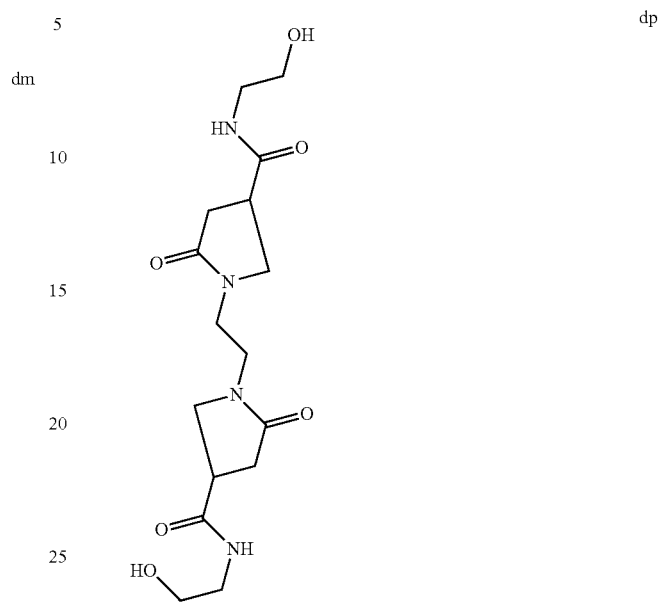
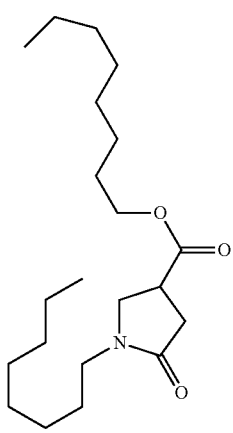
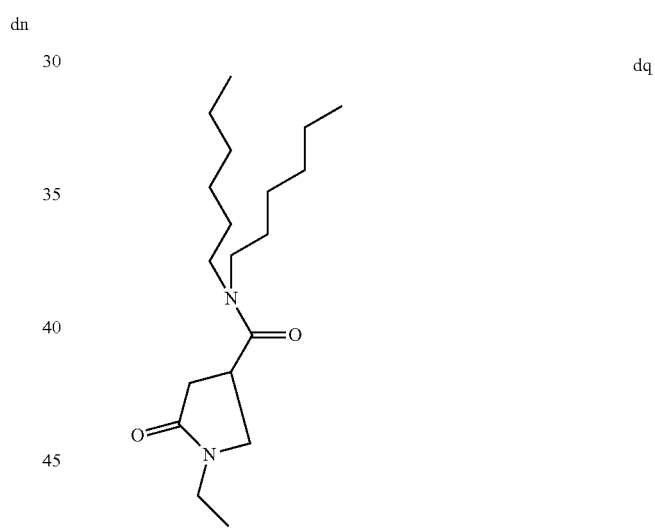
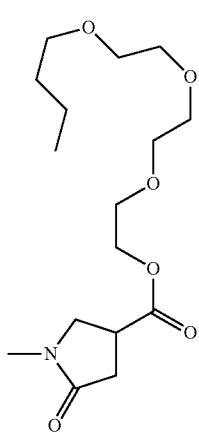
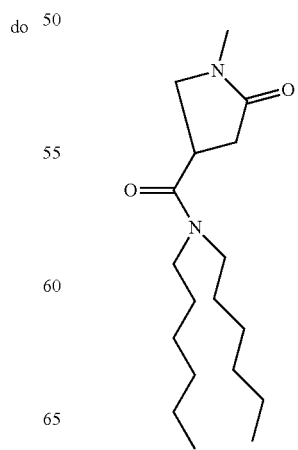

47
-continued
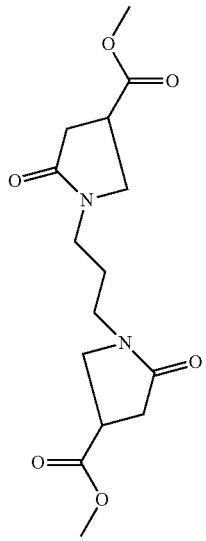
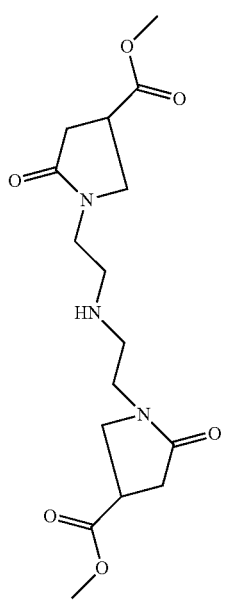
48
-continued
dr
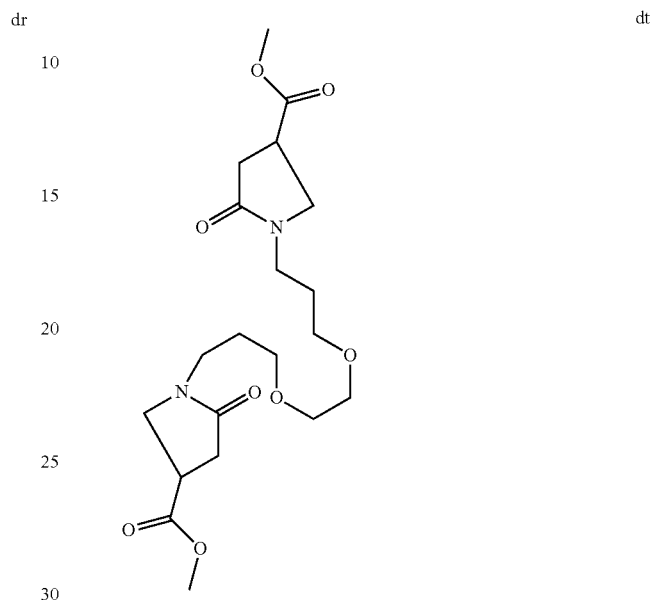
ds
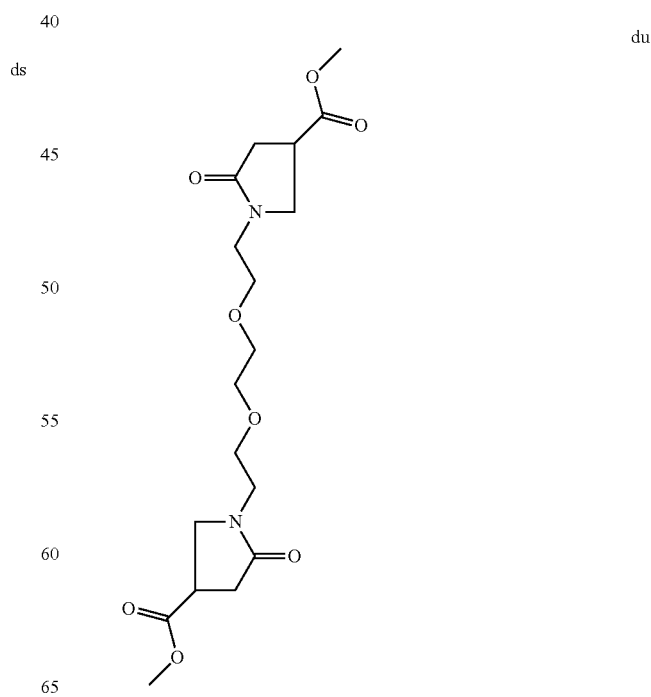
dt
du

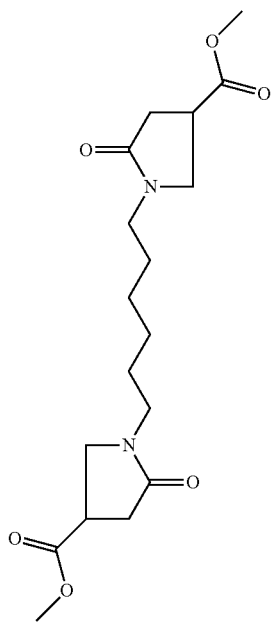
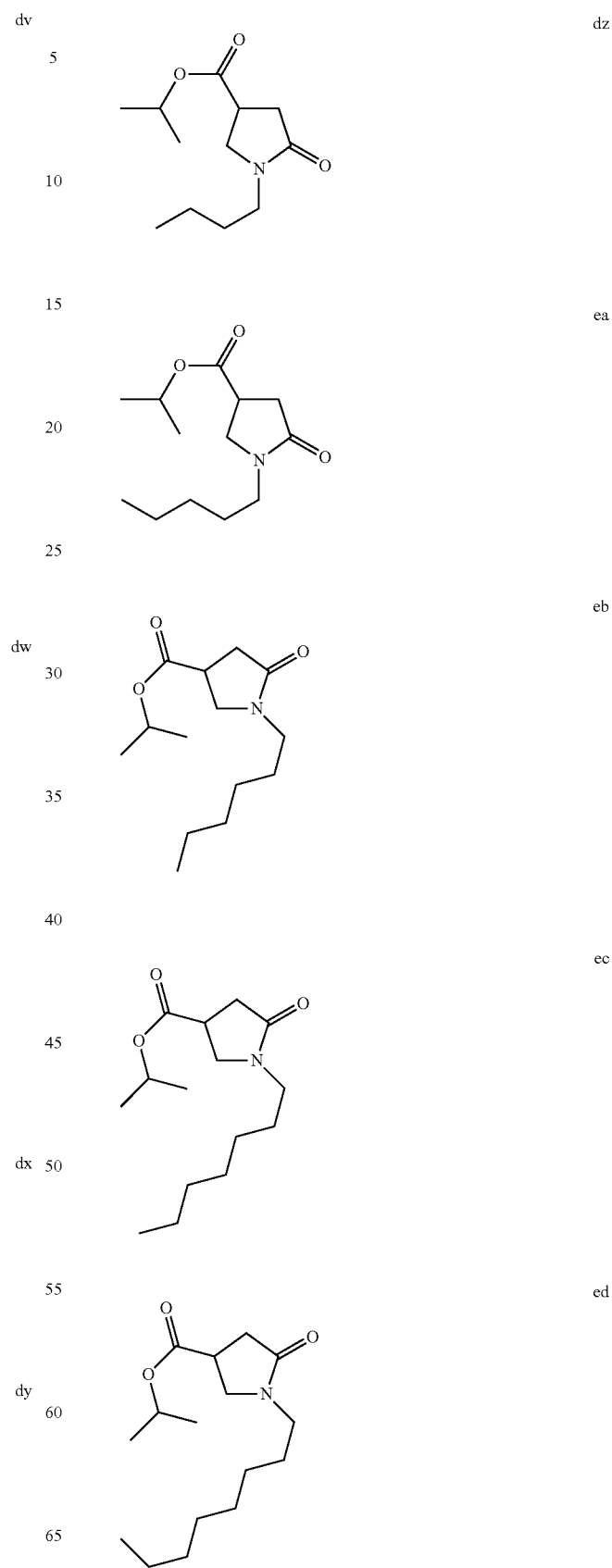

ee
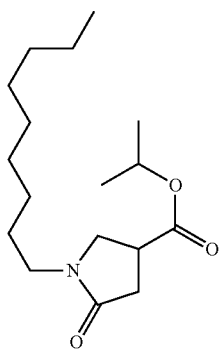
ef
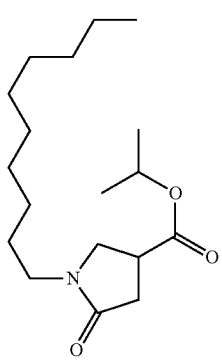
eg
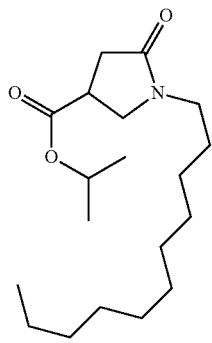
eh
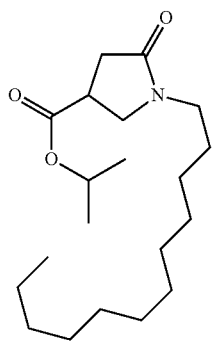
ei
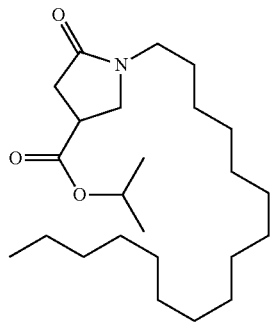
ej
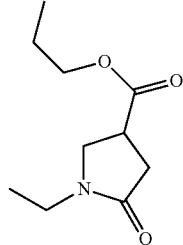
ek
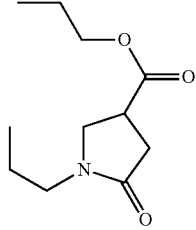
el
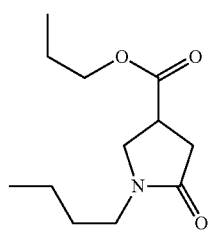
em
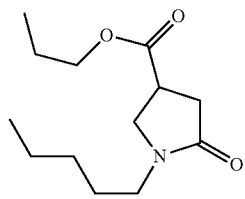
en
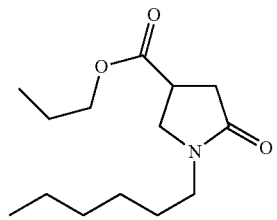

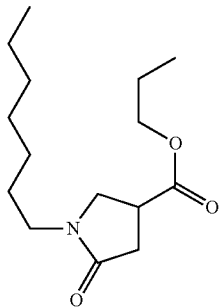
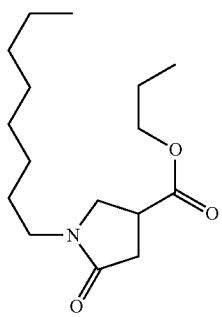
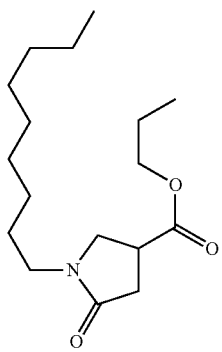
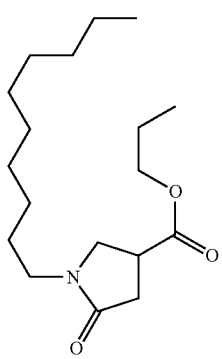
eo
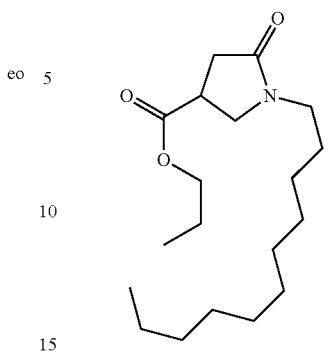
ep
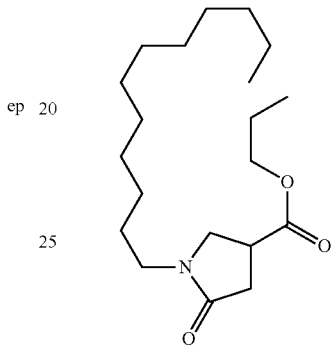
eq
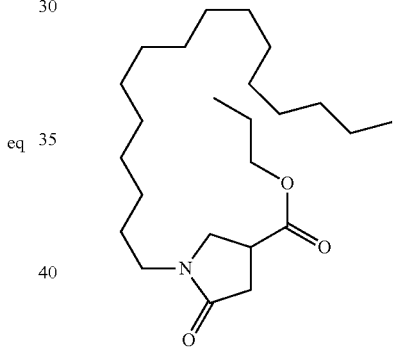
er
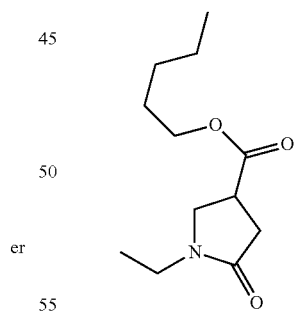
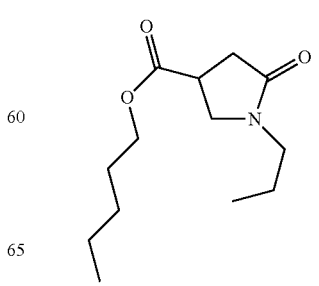
es
and
eu
ev
ew

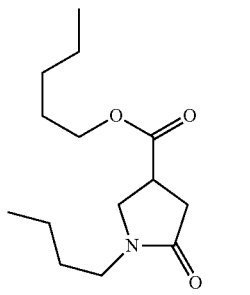
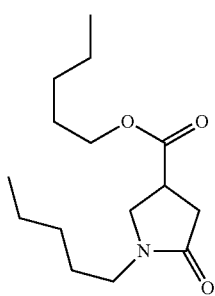
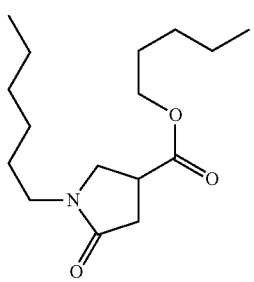
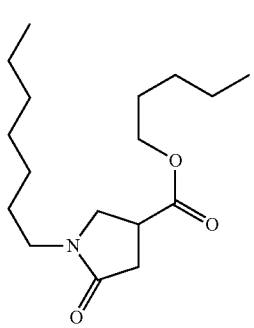
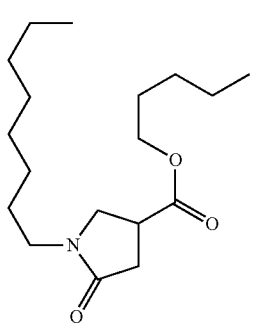
ex
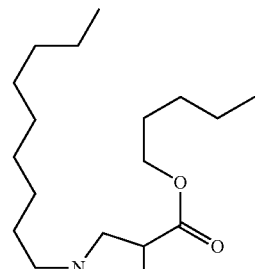
ey
ez
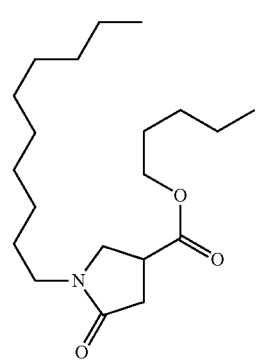
fa
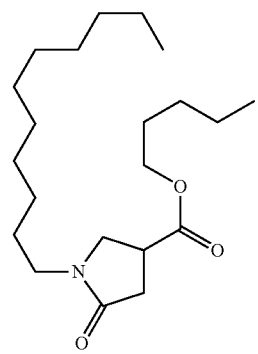
fb
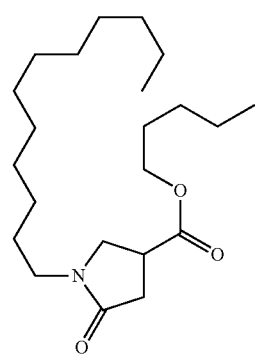
fc
fd
fe
ff fg 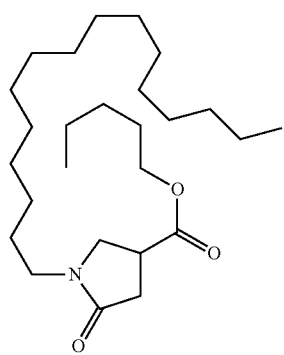
fh 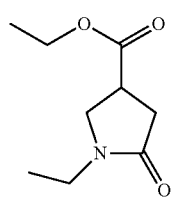
fi 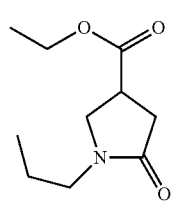
fj 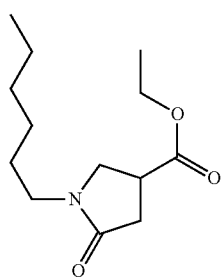
fk 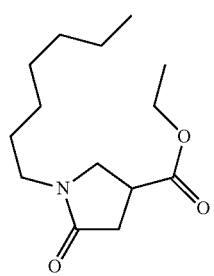
fl 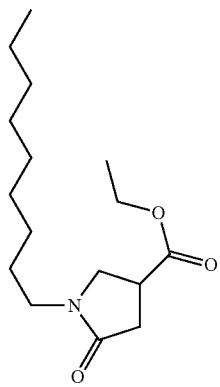
fm 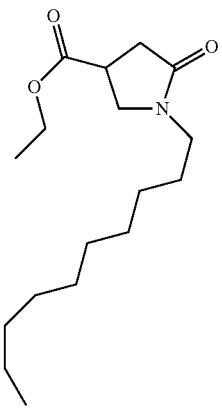
fn 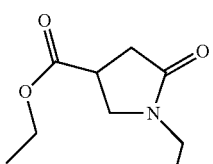
fo 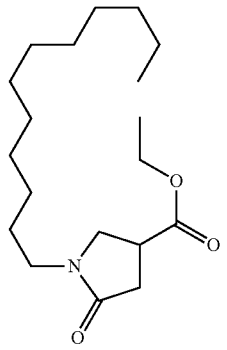

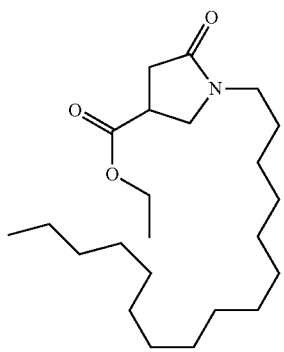
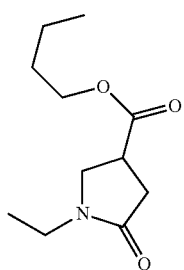
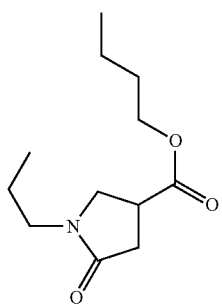
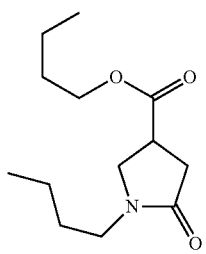
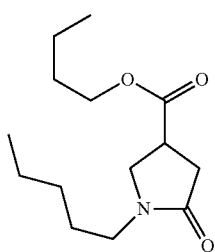
fp
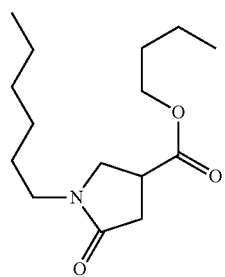
fq
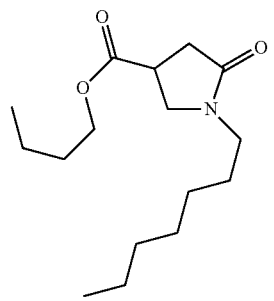
fr
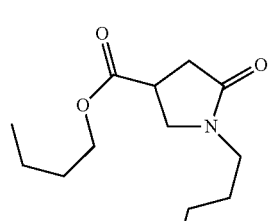
fs
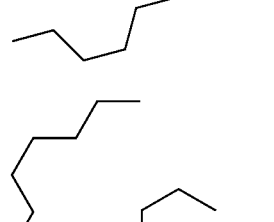
ft
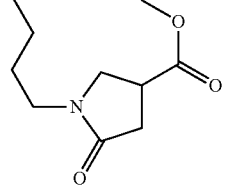
fu
fv
fw
fx
fy

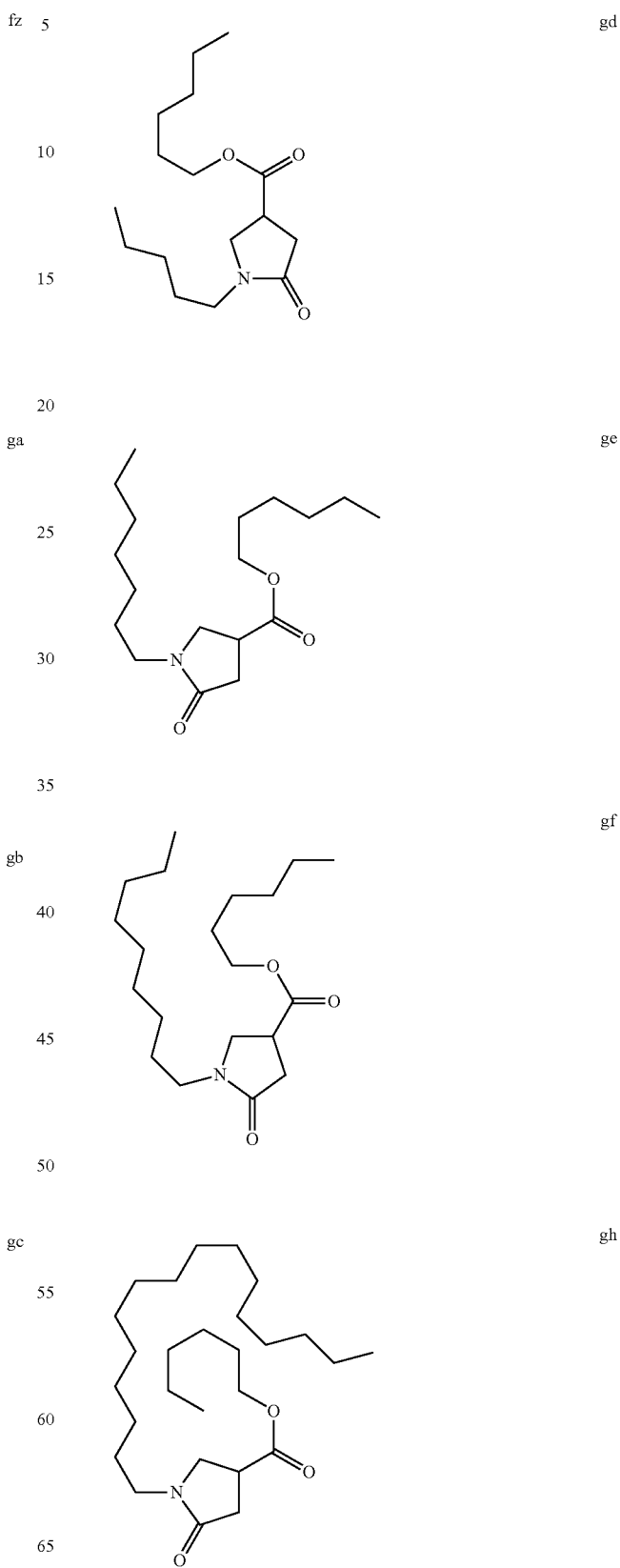

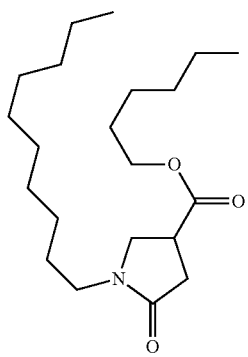 gi
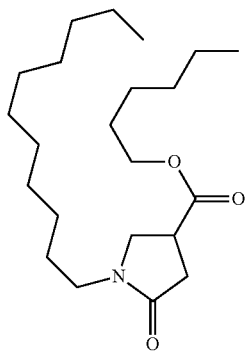 gj
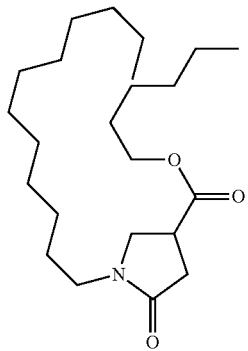 gk
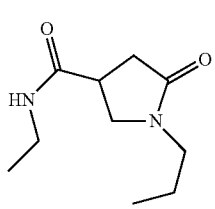 gl
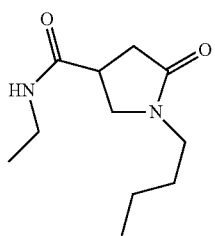 gm
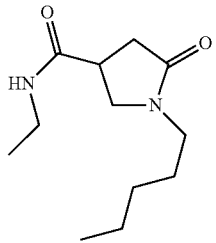 gn
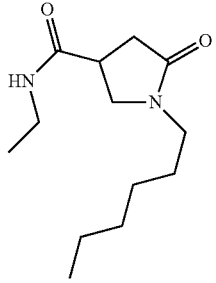 go
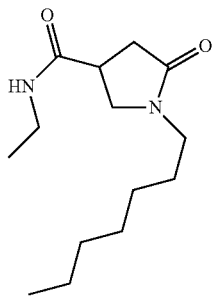 gp
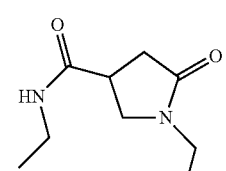 gq
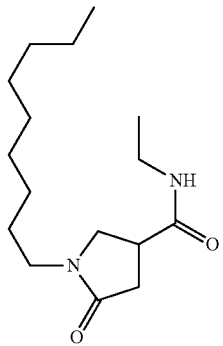 gr

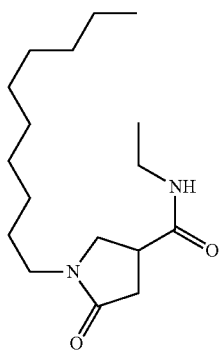
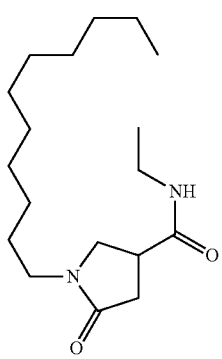
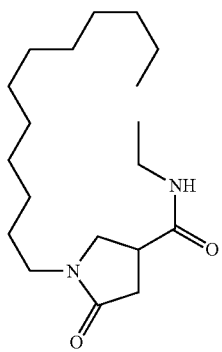
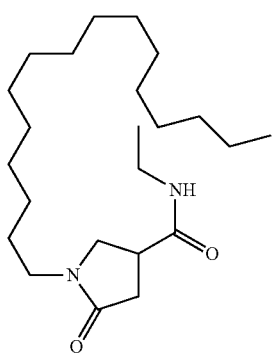
gs
gt
gu
gv
gw
gx
gy
gz
ha
hb
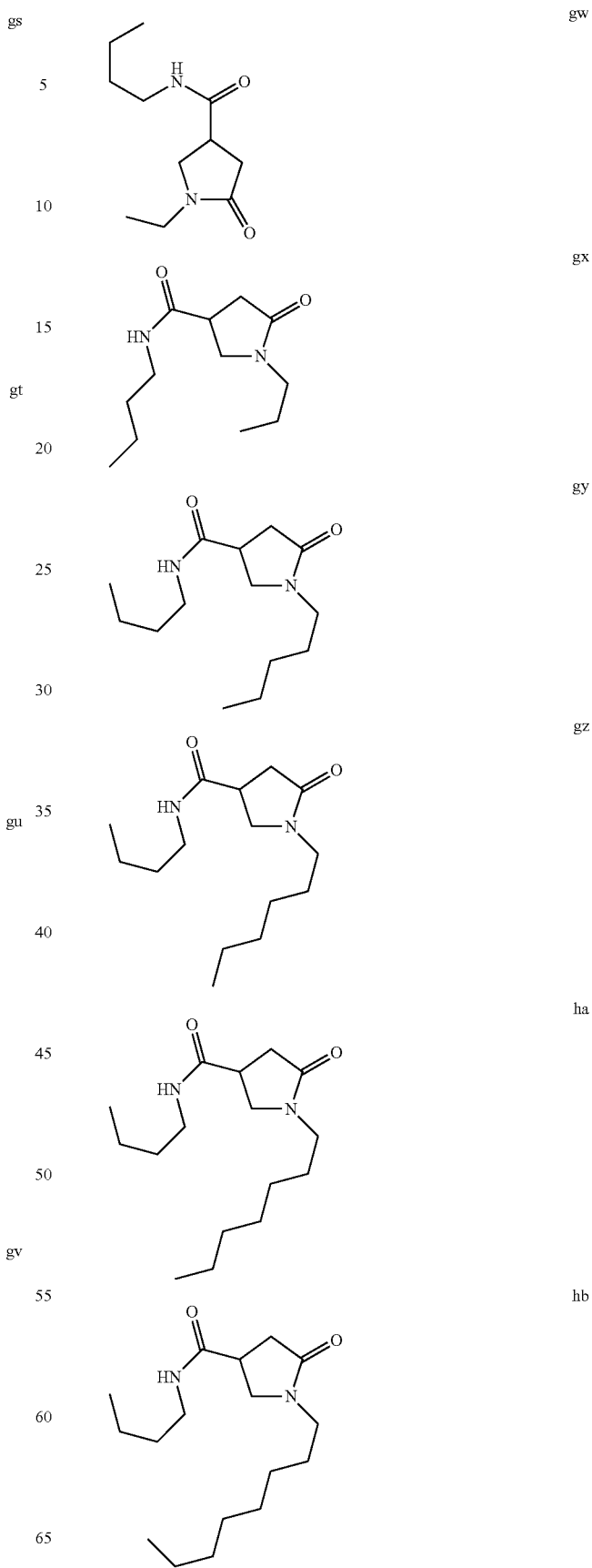

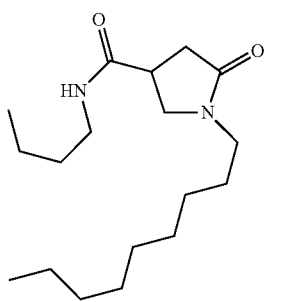
hc
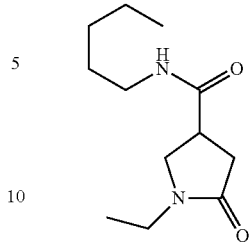
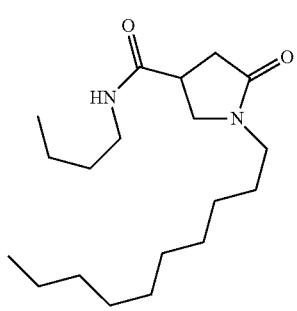
hd
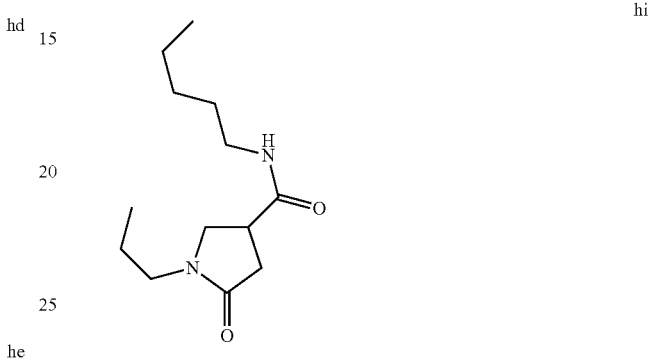
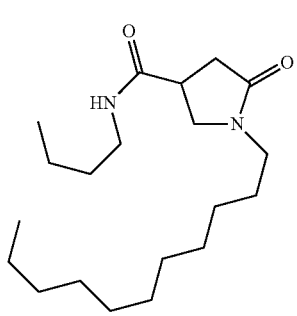
he
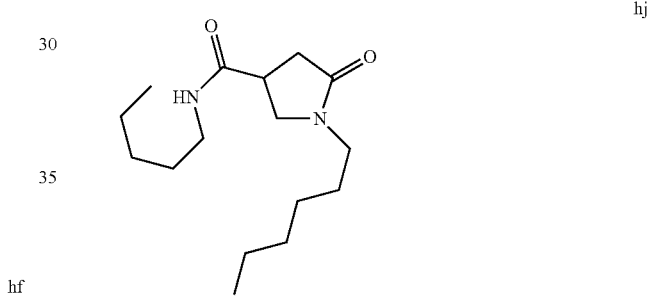
hf
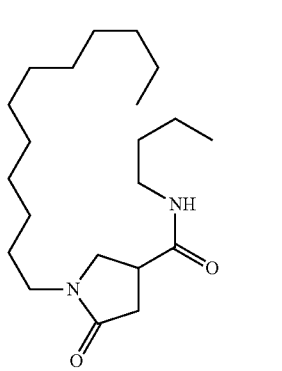
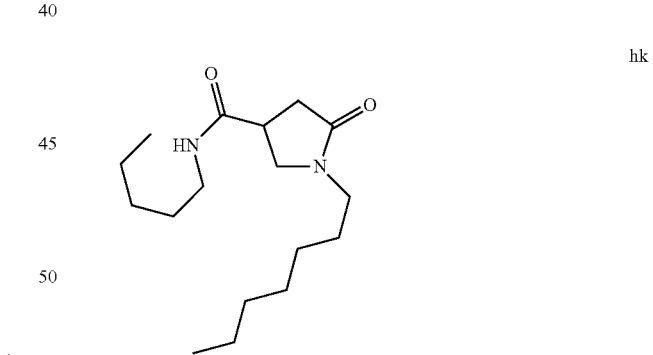
hg
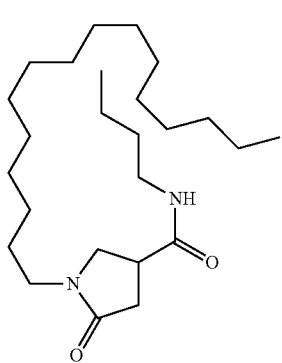
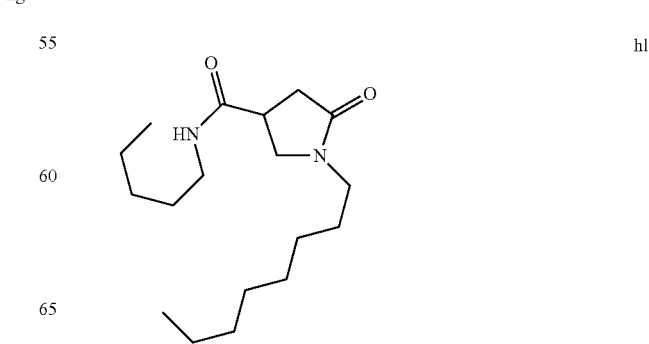

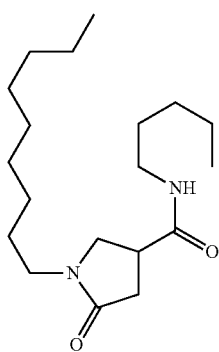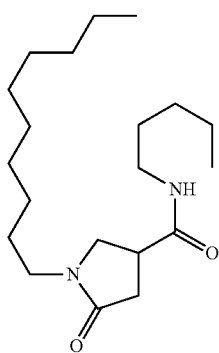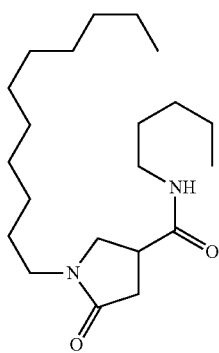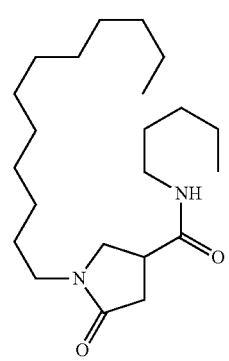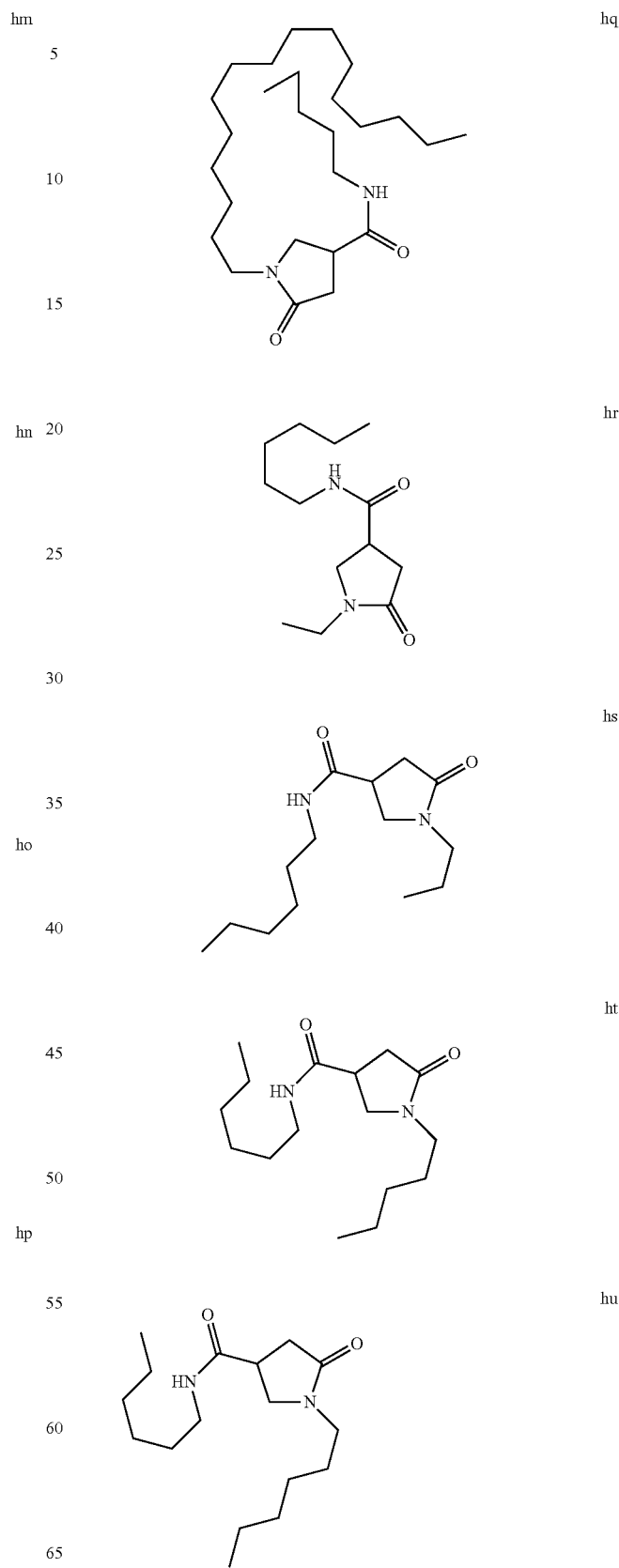

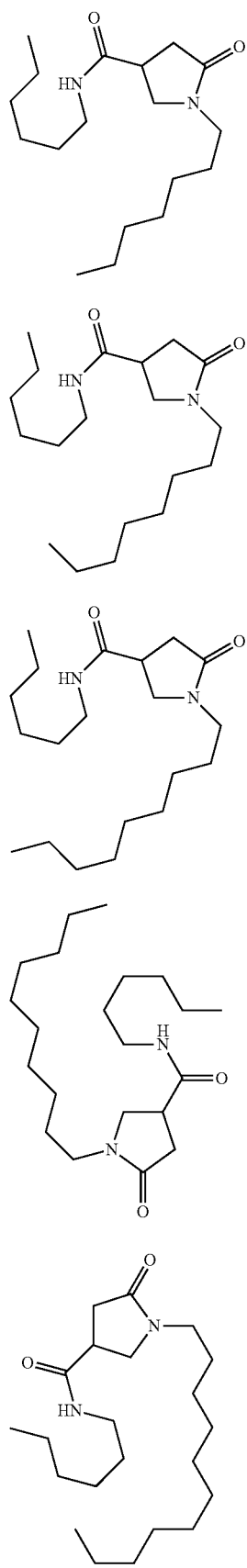
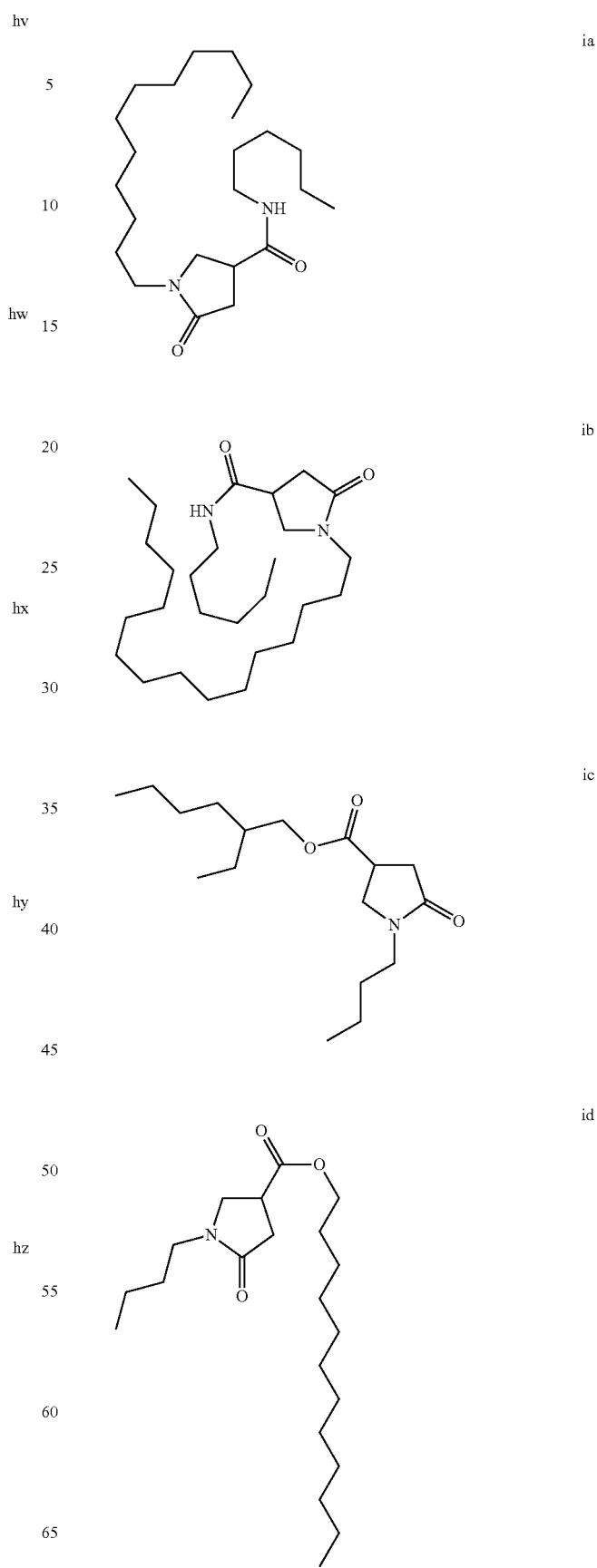

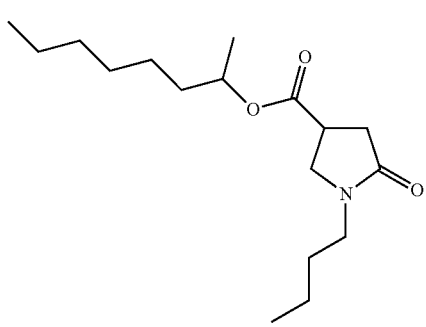

ie

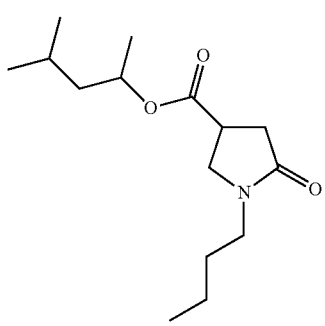

if

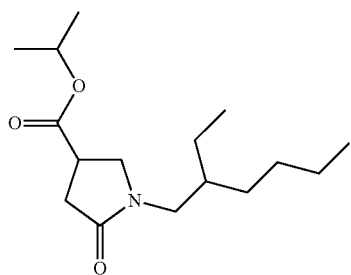

ig

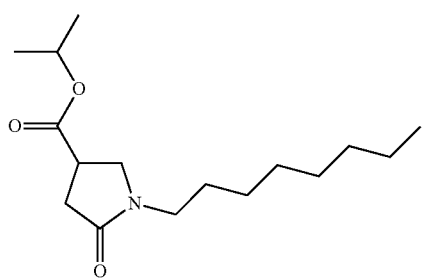

ih

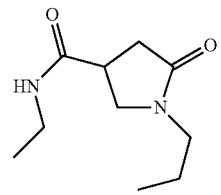

66

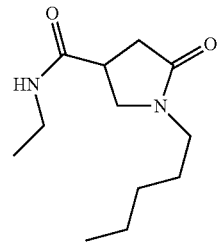

68

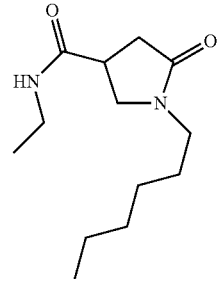

69

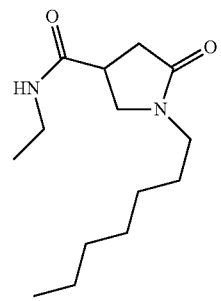

70

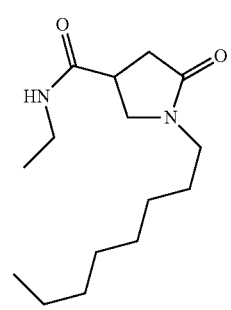

71

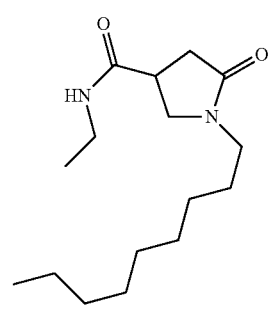

72 with $Q^-$ being an anionic counterion, particularly halide or $(C_1-C_6)$alkoxy sulfate such as mesylate, compounds a to ih, and also the organic or mineral acid or base salts thereof, optical isomers thereof: stereoisomers or enantiomers and diastereoisomers, tautomers thereof, and the solvates thereof such as hydrates.

Another subject of the invention concerns novel compounds of formula (Ia) as defined previously. Particularly, the compounds of formula (Ia) and are such that $R^b$ represents an ethyl, n-propyl, isopropyl, n-butyl, n-pentyl or hexyl.

Preferentially, the compounds of formula (Ia) of the invention are chosen from those of the following list:

73
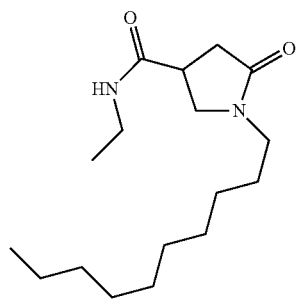
74
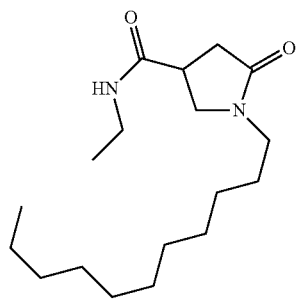
75
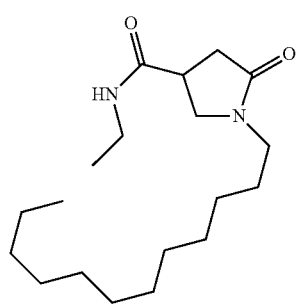
76
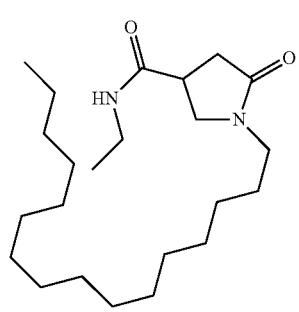
77
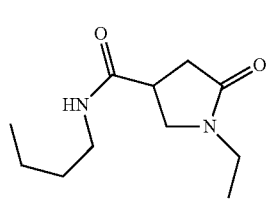
78
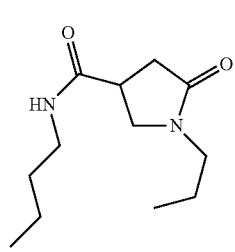
79
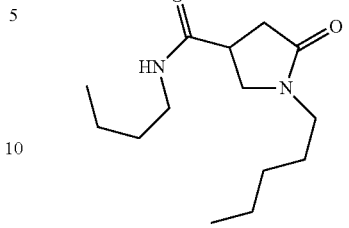
80
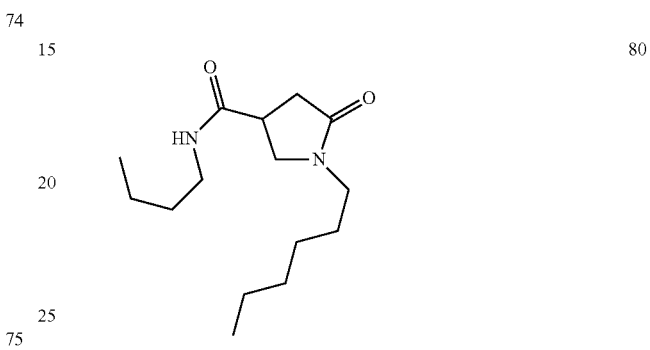
81
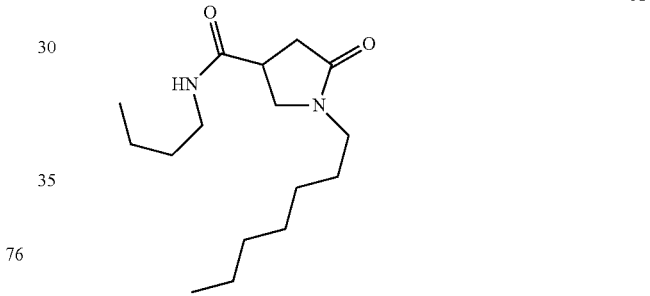
82
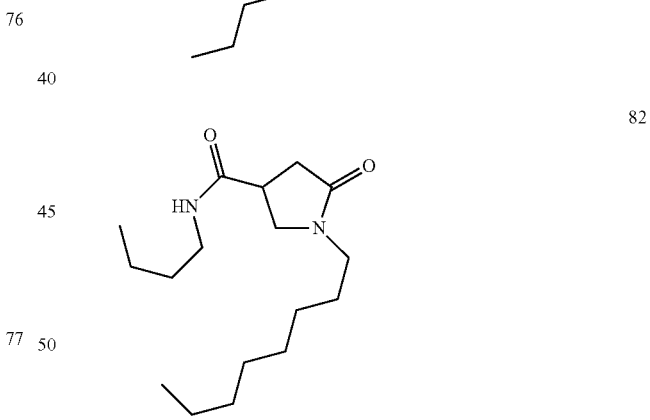
83
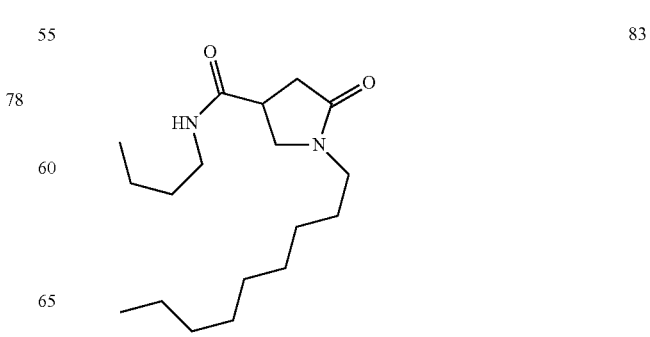

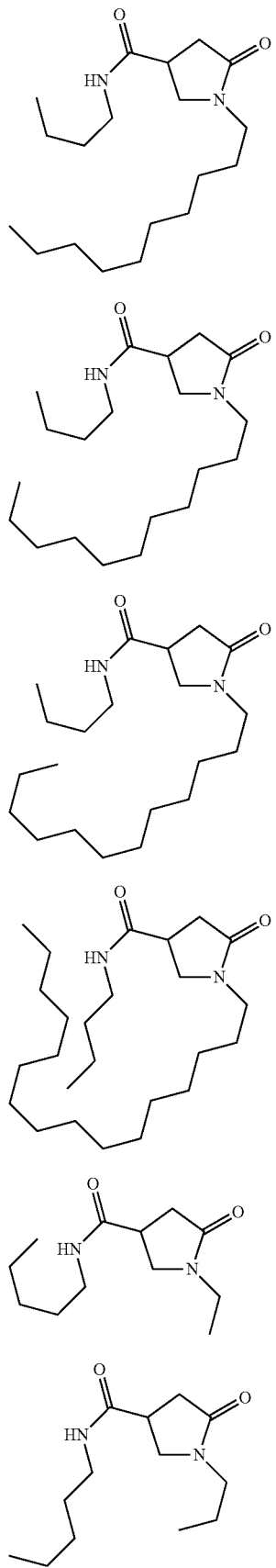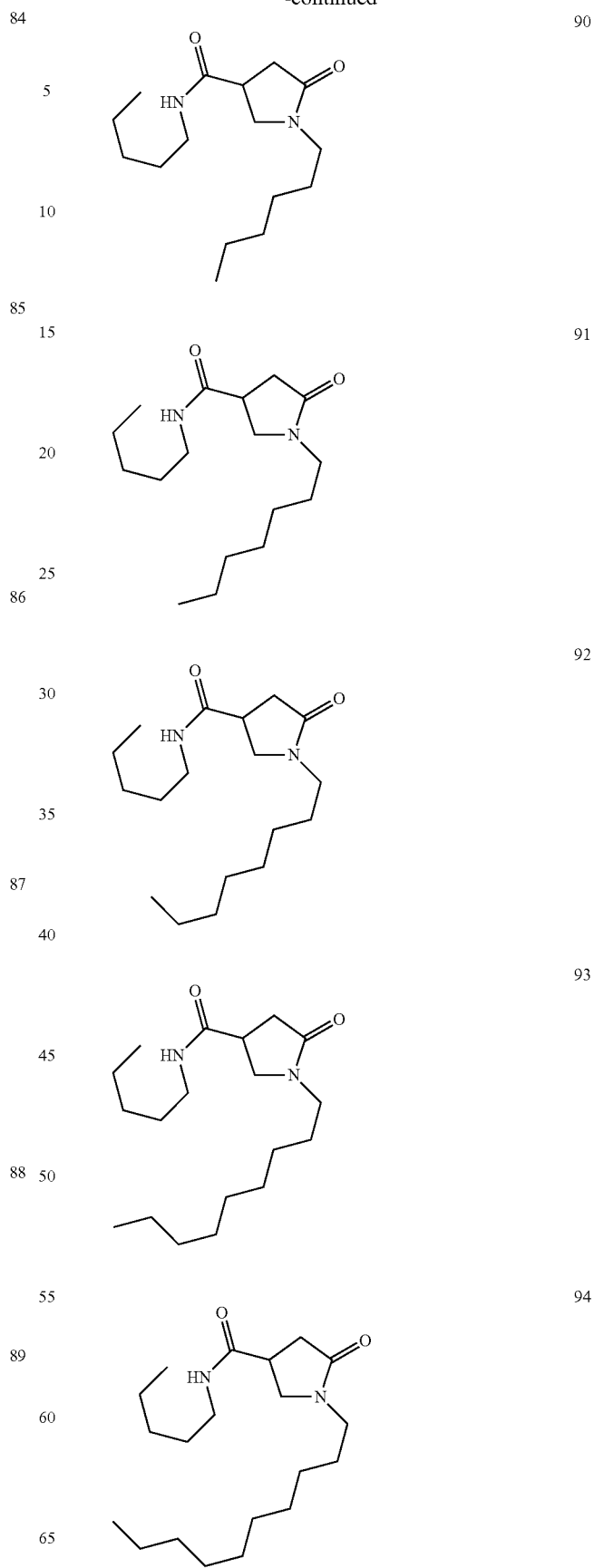

95 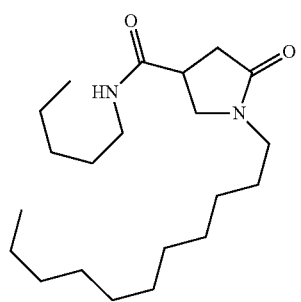
96 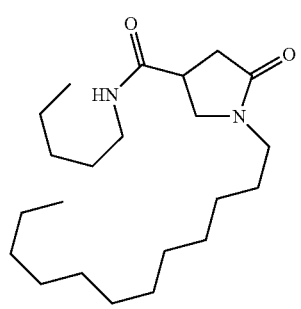
97 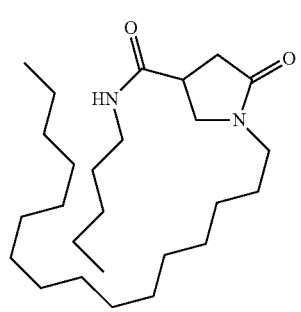
98 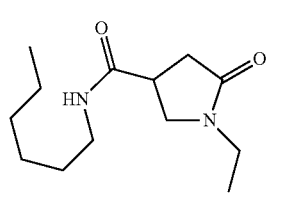
99 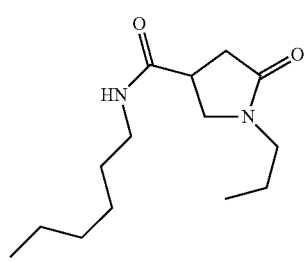
100 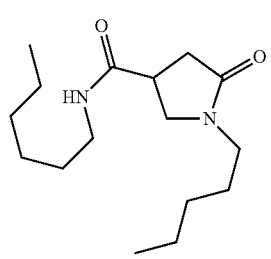
101 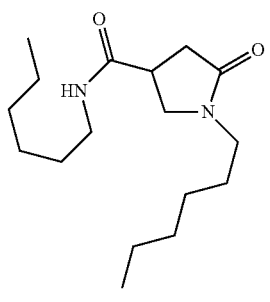
102 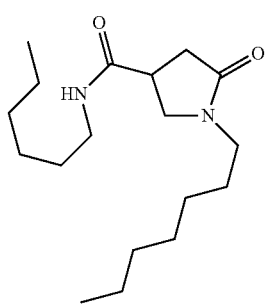
103 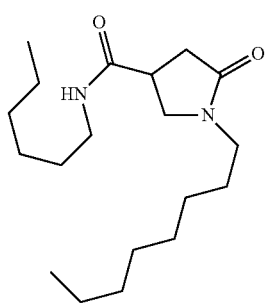
104 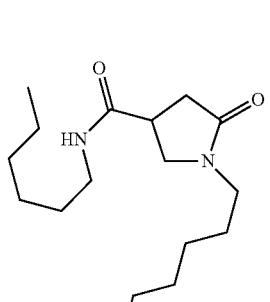
105 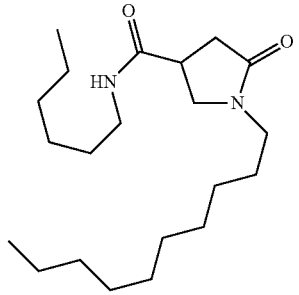

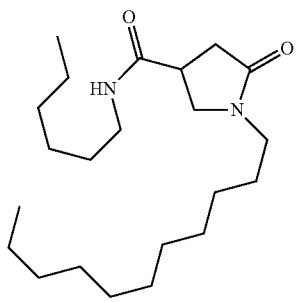

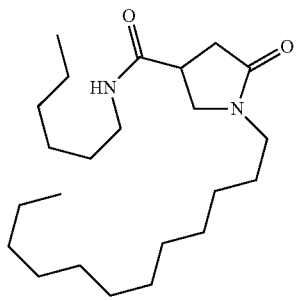

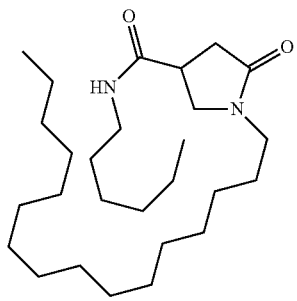

Compounds 66 to 108, and also the organic or mineral acid salts thereof, optical isomers thereof: stereoisomers or enantiomers and diastereoisomers, and the solvates thereof such as hydrates.

The synthesis of the derivatives of formula (I) in which X represents an oxygen atom and R3 and R4=H is described in the following articles: *J. Org. Chem.*, 26, pages 1519-24 (1961); *Tetrahedron Asymmetric*, 12 (23), pages 3241-9 (2001); *J. Industrial & Engineering Chem.*, 47, pages 1572-8 (1955); *J. Am. Chem. Soc.*, 60, pages 402-6 (1938); and in patents EP 0 069 512, U.S. Pat. No. 2,811,496 (1955), U.S. Pat. No. 2,826,588, U.S. Pat. No. 3,136,620, FR 2 290 199 and FR 2 696 744. These derivatives may be readily obtained:

either by condensation of a diester of itaconic acid of formula (II) with a primary amine of formula (III), with or without solvent, at a temperature of between 20° C. and 150° C. according to the following scheme, it being understood that the starting reagents (II) and (III) are readily available via the standard synthetic routes known to those skilled in the art or are commercially available:

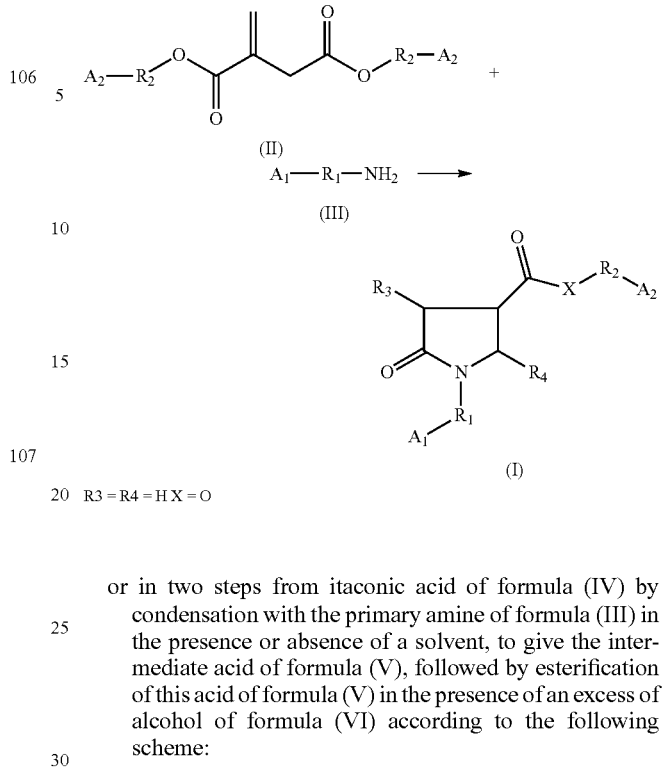

or in two steps from itaconic acid of formula (IV) by condensation with the primary amine of formula (III) in the presence or absence of a solvent, to give the intermediate acid of formula (V), followed by esterification of this acid of formula (V) in the presence of an excess of alcohol of formula (VI) according to the following scheme:

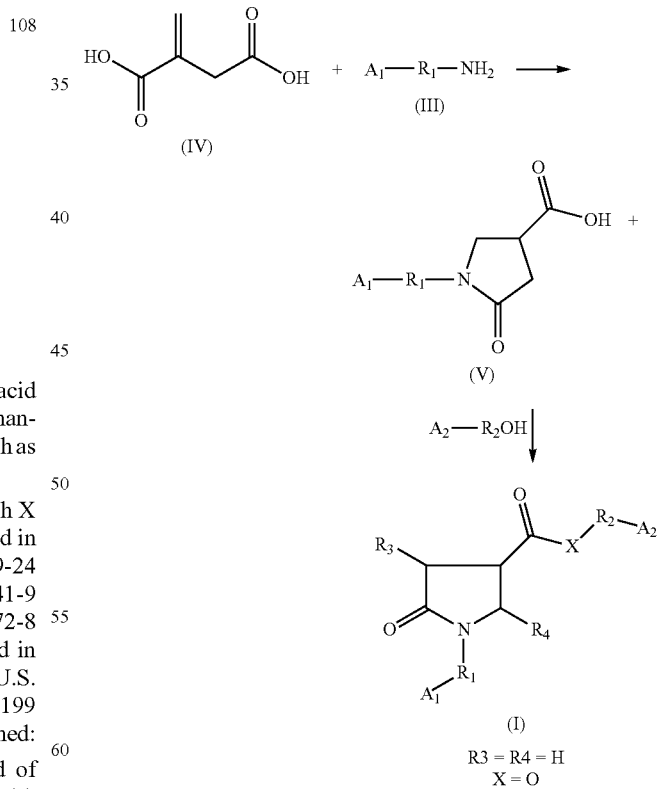

or the derivatives of formula (I) bearing an ester chain R'1 (linear C1-C30 or branched C3-C30 alkyl radical) may also be obtained by transesterification of derivatives bearing an ester chain (methyl or ethyl radical) in the presence of a linear C1-C30 or branched C3-C30 alcohol and a tin or titanium catalyst, according to the following scheme:

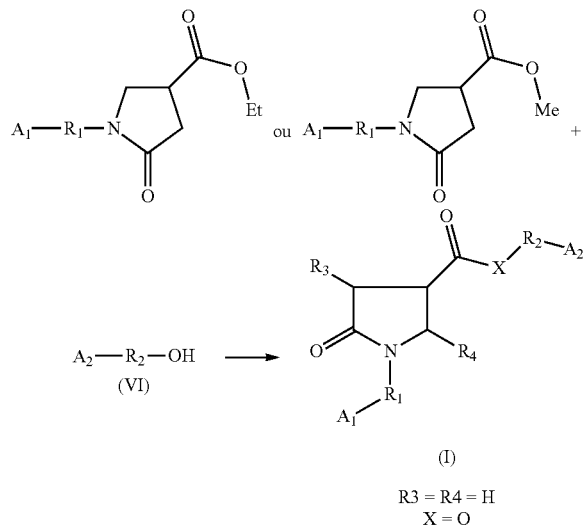

the derivatives of formula (I) in which X represents a divalent amino group —NH— may also be obtained by reaction of the derivatives bearing an ester chain (methyl or ethyl radical) in the presence of a linear C1-C30 or branched C3-C30 amine, as described in the following article: J. Org. Chem., 26, page 4955 (1961) or patent GB 956 253.

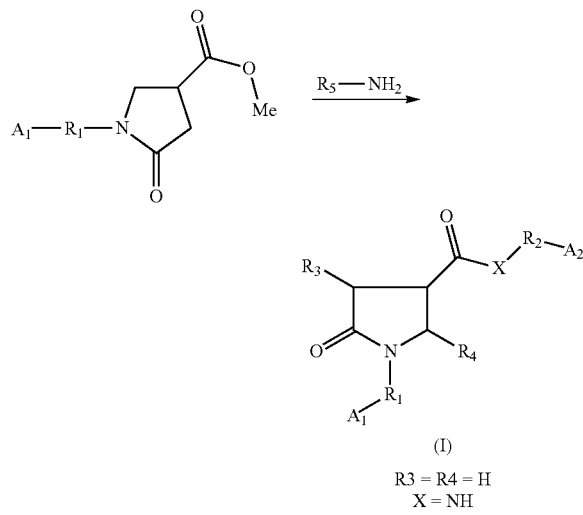

Pigments and Direct Dyes that are Sparingly Soluble or Insoluble in Aqueous-Alcoholic Supports The other ingredient combined with the compound of formula (I) or (Ia) in the invention is a direct dye and/or pigment that is sparingly soluble or insoluble in standard aqueous-alcoholic supports.

Typically, the aqueous-alcoholic support comprises water and an alcohol. Preferentially, at least 50% water and at least 5% alcohol such as ethanol, denatured alcohol, propylene glycol, hexylene glycol, dipropylene glycol, benzyl alcohol or isopropyl alcohol.

According to one particularly preferred mode of the invention, the aqueous-alcoholic support contains only water.

The term "direct dye" means natural and/or synthetic dyes, other than oxidation dyes. These are dyes that will spread superficially on the fibre.

These direct dyes are chosen, for example, from neutral, acidic or cationic nitrobenzene direct dyes, neutral, acidic or cationic azo direct dyes, tetraazapentamethine dyes, neutral, acidic or cationic quinone and in particular anthraquinone dyes, azine direct dyes, triarylmethane direct dyes, azomethine direct dyes and natural direct dyes.

Among the nitrobenzene direct dyes that may be mentioned, in a non-limiting manner, are the following compounds:

1,4-diamino-2-nitrobenzene, 1-amino-2 nitro-4-β-hydroxyethylaminobenzene, 1-amino-2 nitro-4-bis(-hydroxyethyl)-aminobenzene, 1,4-Bis(β-hydroxyethylamino)-2-nitrobenzene, 1-hydroxyethylamino-2-nitro-4-bis-(β-hydroxyethylamino)-benzene, 1-β-hydroxyethylamino-2-nitro-4-aminobenzene, 1-β-hydroxyethylamino-2-nitro-4-(ethyl)(β-hydroxyethylyaminobenzene, 1-amino-3-methyl-4-β-hydroxyethylamino-6-nitrobenzene, 1-amino-2-nitro-4-hydroxyethylamino-5-chlorobenzene, 1,2-Diamino-4-nitrobenzene, 1-amino-2-hydroxyethylamino-5-nitrobenzene, 1,2-Bis(β-hydroxyethylamino)-4-nitrobenzene, 1-amino-2-tris-(hydroxymethyl)-methylamino-5-nitrobenzene, 1-Hydroxy-2-amino-5-nitrobenzene, 1-Hydroxy-2-amino-4-nitrobenzene, 1-Hydroxy-3-nitro-4-aminobenzene, 1-Hydroxy-2-amino-4,6-dinitrobenzene, 1-β-hydroxyethyloxy-2-hydroxyethylamino-5-nitrobenzene, 1-Methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-Hydroxy-2-chloro-6-ethylamino-4-nitrobenzene, 1-Hydroxy-2-chloro-6-amino-4-nitrobenzene, 1-Hydroxy-6-bis-(β-hydroxyethyl)-amino-3-nitrobenzene, 1-β-hydroxyethylamino-2-nitrobenzene, 1-Hydroxy-4-β-hydroxyethylamino-3-nitrobenzene.

Among the azo direct dyes, mention may be made of the cationic azo dyes described in patent applications WO-95/15144, WO-95/01772 and EP-714 954, the content of which forms an integral part of the invention.

Among these compounds, mention may be made most particularly of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]pyridinium methyl sulfate.

Among the azo direct dyes, mention may also be made of the following dyes, described in the Colour Index International 3rd edition:

Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis((β-hydroxyethyl)aminobenzene and 4-hydroxy-3-(2-methoxyphenylazo)-1-naphthalene-sulfonic acid.

Among the quinone direct dyes that may be mentioned are the following dyes:

Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxy-anthraquinone, 1-aminopropylamino-4-methylaminoanthraquinone, 1-aminopropylaminoanthraquinone, 5-β-hydroxyethyl-1,4-diaminoanthraquinone, 2-aminoethylamino-anthraquinone, 1,4-bis(β,γ-dihydroxypropylamino)anthraquinone, 1,4-diamino-5-(2-diethylaminoethylamino)-anthraquinone.

Among the azine dyes that may be mentioned are the following compounds:

Basic Blue 17 and Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the azomethine dyes that may be mentioned are the following compounds:

2-amino-5-(4-aminophenylamino)-6-(4-aminophenylimino)-6H pyridin-3-one

2-[(4-aminophenyl)amino]-4-[(4-aminophenyl)imino]-5-hydroxycyclohexa-2,5-dien-1-one 5-hydroxy-2-[(4-hydroxyphenyl)amino]-4-[(4-hydroxyphenyl)imino]cyclohexa-2,5-dien-1-one 2-({4-[bis(2-hydroxyethyl)amino]phenyl}amino)-4-({4-[bis(2-hydroxyethyl)amino]-phenyl}imino)-5-hydroxycyclohexa-2,5-dien-1-one 5-amino-2-[(4-aminophenyl)amino]-4-[(4-aminophenyl)imino]cyclohexa-2,5-dien-1-one 5-amino-2-[(4-hydroxyphenyl)amino]-4-[(4-hydroxyphenyl)imino]cyclohexa-2,5-dien-1-one 5-amino-2-({4-[bis(2-hydroxyethyl)amino]phenyl}amino)-4-({4-[bis(2-hydroxyethyl)amino]phenyl}imino)cyclohexa-2,5-dien-1-one 2-[(4-aminophenyl)amino]-5-[(2-hydroxyethyl)amino]benzo-1,4-quinone 2-[(2-hydroxyethyl)amino]-5-[(4-hydroxyphenyl)amino]benzo-1,4-quinone 2-({4-[bis(2-hydroxyethyl)amino]phenyl}amino)-5-[(2-hydroxyethyl)amino]benzo-1,4-quinone 2-amino-5-[(4-hydroxyphenyl)amino]-6-[(4-hydroxyphenyl)imino]pyridin-3(6H)-one 2-amino-5-({4-[bis(2-hydroxyethyl)amino]phenyl}amino)-6-({4-[bis(2-hydroxyethyl)amino]phenyl}imino)pyridin-3(6H)-one 3-amino-4-[(4-aminophenyl)imino]-2-chloro-6-methylcyclohexa-2,5-dien-1-one 3-amino-4-[(4-amino-3-methylphenyl)imino]-2-chloro-6-methylcyclohexa-2,5-dien-1-one 3-amino-4-[(4-amino-2-methylphenyl)imino]-2-chloro-6-methylcyclohexa-2,5-dien-1-one 14+75151

3-amino-2-chloro-4-[(4-hydroxyphenyl)imino]-6-methylcyclohexa-2,5-dien-1-one 808+75151

3-amino-4-({4-[bis(2-hydroxyethyl)amino]phenyl}imino)-2-chloro-6-methylcyclohexa-2,5-dien-1-one.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and especially henna-based poultices or extracts, may also be used.

The term "pigment" is intended to denote a white or coloured solid particle, which is naturally insoluble in the liquid hydrophilic and lipophilic phases usually used in cosmetics, or which is made insoluble by formulation in the form of a lake, where appropriate.

Pigments that may be mentioned include organic and inorganic pigments such as those defined and described in Ullmann's Encyclopedia of Industrial Chemistry "Pigment organics", 2005 Wiley-VCH Verlag GmbH & Co. KGaA, Weinheim 10.1002/14356007.a20 371 and ibid, "Pigments, Inorganic, 1. General" 2009 Wiley-VCH Verlag GmbH & Co. KGaA, Weinheim10.1002/14356007.a20_243.pub3

Azo pigments that contain one or more azo groups A-N=N—B with A representing an optionally substituted (hetero)aryl, B representing optionally substituted (hetero)aryl or —CH[C(O)—R]—C(O)—$X_1$-A', A' representing an optionally substituted (hetero)aryl and R representing a hydrogen atom or a group ($C_1$-$C_6$)alkyl, with the groups A, A' and B being (hetero)aryls that do not contain any solubilizing groups such as —$SO_3H$ or —COOH.

They may particularly be monoazo pigments including β-naphthols, monoazopyrrolones, benzimidazolone pigments; diazo pigments such as diazodiarylide pigments and bis(N-acetoacetarylide), and triazo or tetraazo pigments.

Mention may also be made of azo metal complex pigments.

Other pigments are also advantageous, namely isoindolinone and isoindoline pigments, phthalocyanin pigments; quinacridone pigments; perinone pigments; perylene pigments; anthraquinone pigments such as hydroxyanthraquinone pigments; aminoanthraquinone pigments including acylaminoanthraquinones and azo anthraquinone pigments; heterocyclic anthraquinones; polycarboxylic anthraquinone pigments, pyranthrone pigments; anthranthrone pigments; diketopyrrolopyrrole (DPP) pigments; thioindigo pigments; dioxazine pigments; triphenylmethane pigments; quinophthalone pigments; and fluorescent pigments.

When the dyes comprise one or more solubilising groups such as —$SO_3H$ or —COOH, these dyes are made insoluble and consequently pigments by formation of a lake, i.e. by salification (e.g. Na, Ca, St, Ba, etc.) and divided mainly into β-naphthol and 2-hydroxy-3-naphthoic acid pigments "(BON) pigment lakes".

In the context of the present invention, the pigment may be at least partly organic.

According to one embodiment of the invention, the pigment is an organic pigment.

According to another embodiment of the invention, the pigment is a mineral pigment.

The microcapsules according to the invention comprise not more than 80% by weight of pigment relative to the weight of the polymer matrix. In particular, they may comprise from 0.5% to 75% by weight, for example from 1% to 70% by weight, especially from 20% to 65% by weight or even from 30% to 60% by weight of pigment relative to the weight of the polymer matrix.

Needless to say, the degree of encapsulation depends on the desired modification of the shade and may thus vary significantly according to the effect that it is desired to obtain.

As illustrations of pigments that may be used in the present invention, mention may be made of carbon black, titanium oxide, chromium oxide, pigments of D&C or FD&C type and lakes thereof, and especially those known under the names D&C Blue No. 4, D&C Brown No. 1, FD&C Green No. 3, D&C Green No. 5, D&C Green No. 6, FD&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No.

34, D&C Red No. 36, FD&C Red No. 40, FD&C Red 40 lake, D&C Violet No. 2, Ext. D&C Violet No. 2, FD & C Blue No. 1, D&C Yellow No. 6, FD&C Yellow No. 6, D&C Yellow No. 7, Ext. D&C Yellow No. 7, D&C Yellow No. 8, D&C Yellow No. 10 or D&C Yellow No. 11, it being understood that when the said pigment is not naturally insoluble in the hydrophilic and lipophilic phases usually used in cosmetics, it is used in the form of a corresponding lake, as explained previously.

Examples of lakes that may especially be mentioned include lakes based on barium, strontium, calcium or aluminium, or alternatively diketopyrrolopyrroles.

As further examples of pigments that may be used in the present invention, mention may be made especially of mineral pigments, optionally surface-treated and/or coated, and especially titanium dioxide, zirconium oxide or cerium oxide, and also zinc oxide, iron oxide (black, yellow or red) or chromium oxide, manganese violet, ultramarine blue, chromium hydrate and ferric blue, or alternatively metal powders, for instance aluminium powder, copper powder, gold powder and silver powder.

Mention may also be made of pigments with an optical effect such as particles comprising a natural or synthetic organic or mineral substrate, for example glass, acrylic resins, polyester, polyurethane, polyethylene terephthalate, ceramics or aluminas, the said substrate being optionally covered with metal substances, for instance aluminium, gold, silver, platinum, copper or bronze, or with metal oxides, for instance titanium dioxide, iron oxide or chromium oxide.

They may also be nacres.

The term "nacres" should be understood as meaning iridescent particles, which are especially produced by certain molluscs in their shell, or alternatively which are synthesized.

The nacreous pigments may be chosen from mica coated with titanium or with bismuth oxychloride, titanium mica coated with iron oxides, titanium mica coated especially with ferric blue or with chromium oxide, titanium mica coated with an organic pigment of the abovementioned type, and also nacreous pigments based on bismuth oxychloride. Interference pigments, especially liquid-crystal or multilayer pigments, may also be used.

They may also be pigments having a structure that may be, for example, of sericite/brown iron oxide/titanium dioxide/silica type.

They may also be pigments having a structure that may be, for example, of silica microsphere type containing iron oxide.

As examples of pigments and lakes that are most particularly suitable for use in the present invention, mention may be made especially of D&C Red No. 7, titanium oxide, chromium oxide, lakes of the pigments of D&C and FD&C type mentioned above, and especially D&C Red No. 22 lake, Yellow No. 6 lake and FD&C Blue No. 1 lake.

These pigments may be in the form of powder or of pigmentary paste. They may be coated or uncoated.

The pigments in accordance with the invention may be chosen, for example, from white or coloured pigments, lakes, pigments with special effects such as nacres or flakes, and mixtures thereof.

Examples of white or coloured mineral pigments that may be mentioned include zirconium oxide or cerium oxide, chromium oxides, manganese violet, ultramarine blue, chromium hydrate and ferric blue.

Examples of white or coloured organic pigments that may be mentioned include nitroso, nitro, azo, xanthene, quinoline, anthraquinone and phthalocyanin compounds, compounds of metallic complex type, and isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Colour Index under the references CI 42090, 69800, 69825, 73000, 74100, 74160, the yellow pigments codified in the Colour Index under the references CI 11680, 11710, 15985, 19140, 20040, 21100, 21108, 47000, 47005, the green pigments codified in the Colour Index under the references CI 61565, 61570, 74260, the orange pigments codified in the Colour Index under the references CI 11725, 15510, 45370, 71105, the red pigments codified in the Colour Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

Pigmentary pastes of organic pigment may be used, such as the products sold by the company Hoechst under the name:
Jaune Cosmenyl IOG: Pigment Yellow 3 (CI 11710);
Jaune Cosmenyl G: Pigment Yellow 1 (CI 11680);
Orange Cosmenyl GR: Pigment Orange 43 (CI 71105);
Rouge Cosmenyl R: Pigment Red 4 (CI 12085);
Carmin Cosmenyl FB: Pigment Red 5 (CI 12490);
Violet Cosmenyl RL: Pigment Violet 23 (CI 51319);
Bleu Cosmenyl A2R: Pigment Blue 15.1 (CI 74160);
Vert Cosmenyl GG: Pigment Green 7 (CI 74260);
Noir Cosmenyl R: Pigment Black 7 (CI 77266).

The pigments in accordance with the invention may also be in the form of composite pigments as described in patent EP 1 184 426. These composite pigments may be compounds, especially particles, comprising:
an inorganic core,
at least one binder for fixing the organic pigments to the nucleus, and
at least one organic pigment at least partially covering the nucleus.

The term "lake" means dyes adsorbed onto insoluble particles, the assembly thus obtained remaining insoluble during use. The mineral substrates onto which the dyes are adsorbed are, for example, alumina, silica, calcium sodium borosilicate or calcium aluminium borosilicate, and aluminium. Among the organic dyes that may be mentioned is cochineal carmine.

Examples of lakes that may be mentioned include the products known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053), D & C Blue 1 (CI 42 090).

The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They are consequently in contrast with white or coloured pigments, which afford a standard opaque, semi-transparent or transparent uniform shade.

Examples of pigments with special effects that may be mentioned include white nacreous pigments such as mica coated with titanium or with bismuth oxychloride, coloured nacreous pigments such as mica coated with titanium and with iron oxides, mica coated with titanium and especially with ferric blue or with chromium oxide, mica coated with titanium and with an organic pigment as defined above, and also nacreous pigments based on bismuth oxychloride.

Mention may also be made of pigments with an interference effect not bound to a substrate, for instance liquid crystals (Helicones HC from Wacker), holographic interference flakes (Geometric Pigments or Spectra f/x from Spectratek).

The pigments with special effects also comprise fluorescent pigments, whether they are substances that are fluorescent in daylight or that produce ultraviolet fluorescence, phosphorescent pigments, photochromic pigments, thermochromic pigments and quantum dots, for example sold by the company Quantum Dots Corporation.

Quantum dots are luminescent semiconductive nanoparticles capable of emitting, under light excitation, radiation with a wavelength of between 400 nm and 700 nm. These nanoparticles are known in the literature. In particular, they may be manufactured according to the processes described, for example, in U.S. Pat. No. 6,225,198 or U.S. Pat. No. 5,990,479, in the publications cited therein and also in the following publications: Dabboussi B. O. et al "(CdSe)ZnS core-shell quantum dots: synthesis and characterization of a size series of highly luminescent nanocristallites" Journal of Physical Chemistry B, vol. 101, 1997, pp. 9463-9475 and Peng, Xiaogang et al., "Epitaxial Growth of highly Luminescent CdSe/CdS core/shell nanocrystals with photostability and electronic accessibility" Journal of the American Chemical Society, vol. 119, No. 30, pp. 7019-7029.

The pigments in accordance with the invention are preferably coloured pigments.

The variety of pigments used makes it possible to obtain a wide range of colours, and also particular optical effects such as metallic or interference effects.

The size of a pigment other than the nacres in solution is generally between 10 nm and 10 μm, preferably between 50 nm and 5 μm and even more preferentially between 100 nm and 3 μm. The size of a nacre in solution is generally between 1 and 200 μm, preferably between 1 and 80 μm and even more preferentially between 1 and 50 μm.

Among the mineral pigments, examples that may be mentioned include titanium dioxide (rutile or anatase) optionally surface-treated and codified in the Colour Index under the reference CI 77891; black, yellow, red and brown iron oxides, codified under the references CI 77499, 77492 and 77491; manganese violet (CI 77742); ultramarine blue (CI 77007); hydrated chromium oxide (CI 77289); ferric blue (CI 77510).

Among the organic pigments that may be mentioned, for example, are the pigment Yellow 3 sold in particular under the trade name "Jaune Covanor W 1603" by the company Wackherr (CI 17710), "D & C Red No. 19" (CI 45170), "D & C Red No. 9" (CI 15585), "D & C Red No. 21" (CI 45380), "D & C Orange No. 4" (CI 15510), "D & C Orange No. 5" (CI 45370), "D & C Red No. 27" (CI 45410), "D & C Red No. 13" (CI-15630), "D & C Red No. 7" (CI 15850-1), "D & C Red No. 6" (CI 15850-2), "D & C Yellow No. 5" (CI 19140), "D & C Red No. 36" (CI 12085), "D & C Orange No. 10" (CI-45425), "D & C Yellow No. 6" (CI 15985), "D & C Red No. 30" (CI 73360), "D & C Red No. 3" (CI 45430), carbon black (CI 77266) and lakes based on cochineal carmine (CI-75470).

It is also possible to use nacreous pigments, which may be chosen in particular from white nacreous pigments such as mica coated with titanium oxide or bismuth oxide; coloured nacreous pigments such as titanium mica with iron oxides, titanium mica with ferric blue or with chromium oxide, titanium mica with an organic pigment of the abovementioned type, and also those based on bismuth oxychloride.

Pigmentary pastes of organic pigment are used more particularly, such as the products sold by the company Hoechst under the name:

Jaune Cosmenyl 1OG: Pigment Yellow 3 (CI 11710);
Jaune Cosmenyl G: Pigment Yellow 1 (CI 11680);
Orange Cosmenyl GR: Pigment Orange 43 (CI 71105)
Rouge Cosmenyl R: Red 4 Pigment (CI 12085)
Carmin Cosmenyl FB: Red 5 Pigment (CI 12490)
Violet Cosmenyl RL: Violet Pigment 23 (CI 51319)
Bleu Cosmenyl A2R: Blue 15.1 Pigment (CI 74260)
Vert Cosmenyl GG: Green 7 Pigment (CI 74260)
Noir Cosmenyl R: Black 7 Pigment (CI 77266)

The pigments are present in concentrations preferably ranging from 0.05% to 10% by weight and even more particularly from 0.1% to 3% by weight relative to the total weight of the composition.

The direct dyes and/or pigments that may be used in the composition of the invention are sparingly soluble or insoluble in water or aqueous-alcoholic medium, known to those skilled in the art. Examples that may be mentioned include:

| Dye | Chemical structure |
|---|---|
| Solvent Black 3 | 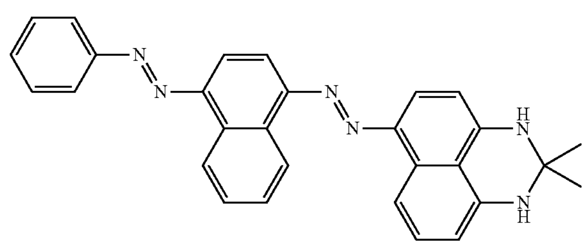 [SMILES: CC1(C)Nc2cccc3c(/N=N/c4ccc(/N=N/c5ccccc5)c5ccccc45)ccc(c23)N1] |
| Solvent Blue 104 | 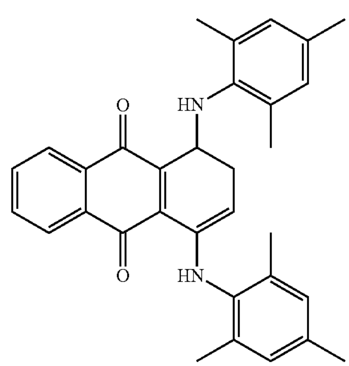 [SMILES: Cc1cc(C)c(NC2=CCC(Nc3c(C)cc(C)cc3C)C3=C2C(=O)c2ccccc2C3=O)c(C)c1] |

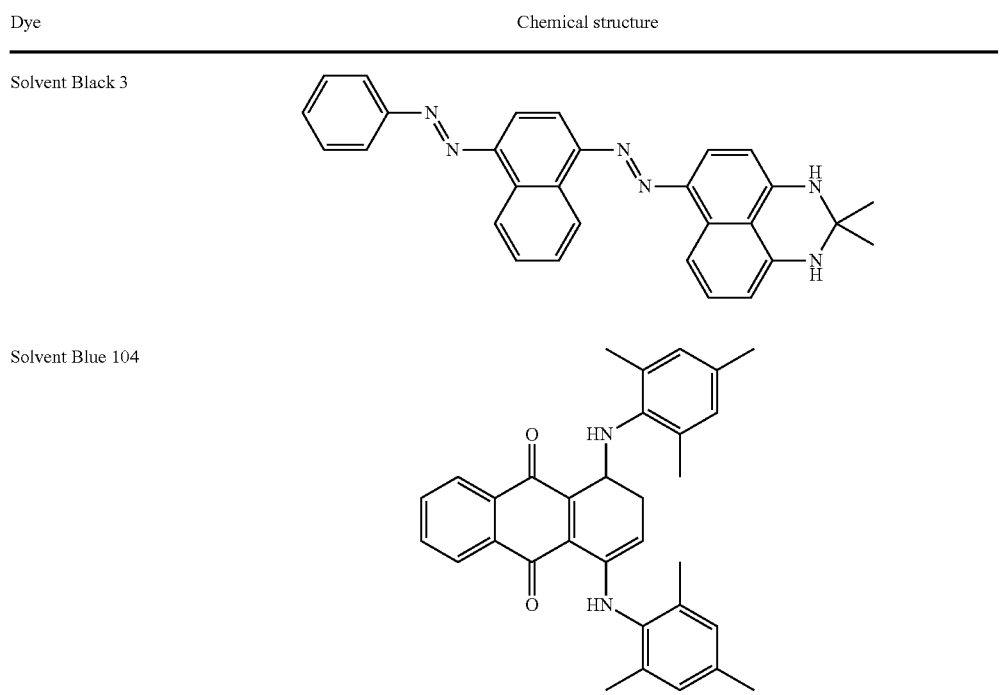

-continued

| Dye | Chemical structure |
|---|---|
| Disperse Blue 134 | 1,4-bis(isopropylamino)anthraquinone |
| Solvent Blue 14 | 1,4-bis(pentylamino)anthraquinone |
| Disperse Blue 14 | 1,4-bis(methylamino)anthraquinone |
| Solvent Red 2 | 1-(o-tolylazo)-4-hydroxynaphthalene |
| Solvent Brown 5 | 1-(naphthalen-1-ylazo)-4-hydroxynaphthalene |
| Solvent Green 5 | diisobutyl perylene-3,9-dicarboxylate |

-continued
| Dye | Chemical structure |
|---|---|
| Solvent Orange 2 | 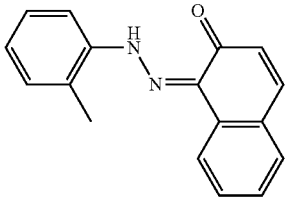 [SMILES: Cc1ccccc1N/N=C1\C(=O)C=Cc2ccccc21] |
| Solvent Orange 1 | 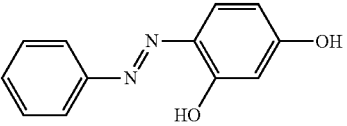 [SMILES: Oc1ccc(/N=N/c2ccccc2)c(O)c1] |
| Disperse Orange 24 | 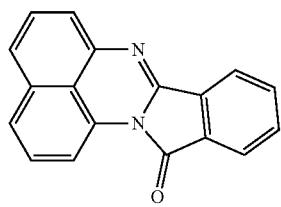 [SMILES: O=C1c2ccccc2C2=Nc3cccc4cccc(c34)N12] |
| Solvent Orange 63 | 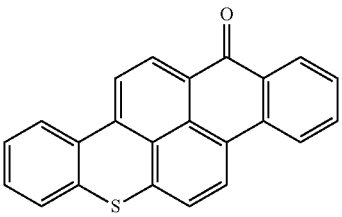 [SMILES: O=c1c2ccccc2c2ccc3sc4ccccc4c4ccc1c2c34] |
| Solvent Red 49 | 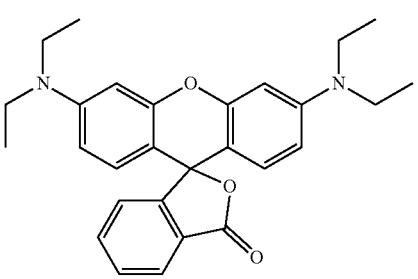 [SMILES: CCN(CC)c1ccc2c(c1)Oc1cc(N(CC)CC)ccc1C21OC(=O)c2ccccc21] |
| Solvent Red 1 | 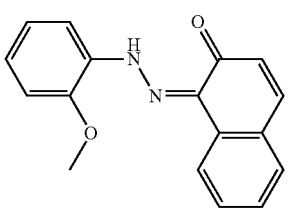 [SMILES: COc1ccccc1N/N=C1\C(=O)C=Cc2ccccc21] |
| Solvent Red 26 | 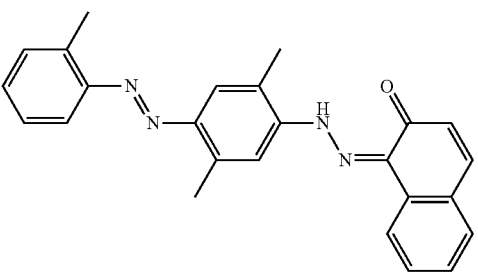 [SMILES: Cc1ccccc1/N=N/c1cc(C)c(N/N=C2\C(=O)C=Cc3ccccc32)cc1C] |

-continued
| Dye | Chemical structure |
|---|---|
| Solvent Red 27 | 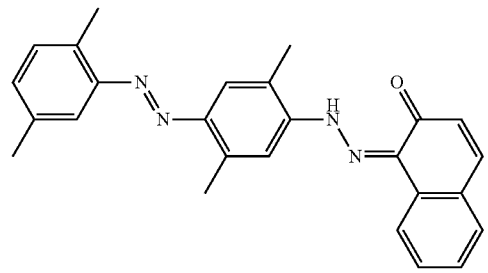 [SMILES: Cc1ccc(C)c(/N=N/c2cc(C)c(N/N=C3\C(=O)C=Cc4ccccc43)cc2C)c1] |
| Solvent Red 18 | 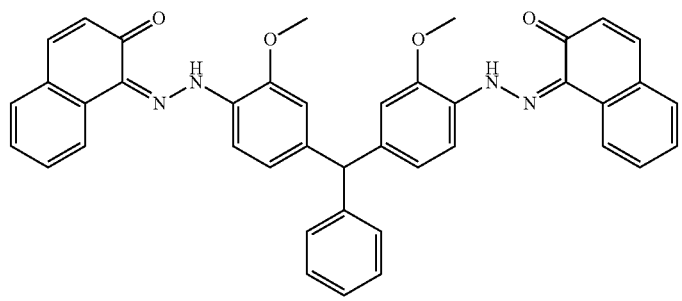 [SMILES: COc1cc(C(c2ccccc2)c2ccc(N/N=C3\C(=O)C=Cc4ccccc43)c(OC)c2)ccc1N/N=C1\C(=O)C=Cc2ccccc21] |
| Solvent Red 23 | 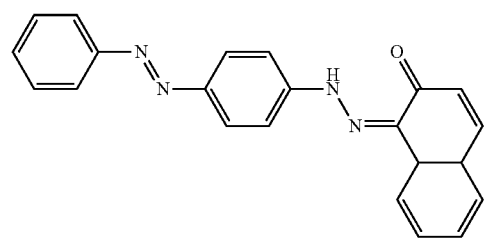 [SMILES: O=C1C=CC2C=CC=CC2/C1=N/Nc1ccc(/N=N/c2ccccc2)cc1] |
| Solvent Red 4 | 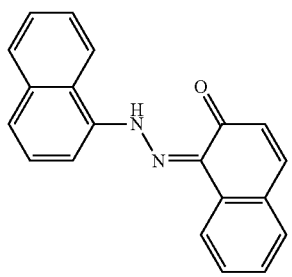 [SMILES: O=C1C=Cc2ccccc2/C1=N/Nc1cccc2ccccc12] |
| Solvent Orange 7 | 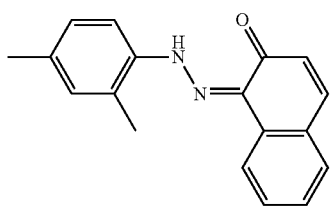 [SMILES: Cc1ccc(N/N=C2\C(=O)C=Cc3ccccc32)c(C)c1] |
| Disperse Blue 72 | 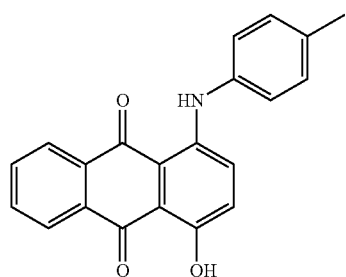 [SMILES: Cc1ccc(Nc2ccc(O)c3c2C(=O)c2ccccc2C3=O)cc1] |

-continued
| Dye | Chemical structure |
|---|---|
| Disperse Violet 26 | 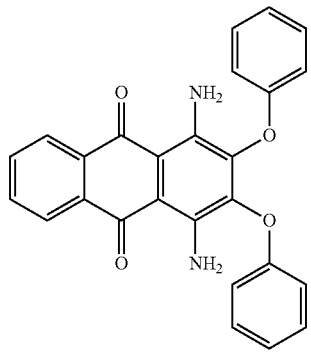 [SMILES: Nc1c(Oc2ccccc2)c(Oc2ccccc2)c(N)c2c1C(=O)c1ccccc1C2=O] |
| Disperse Yellow 16 | 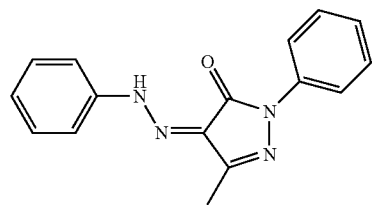 [SMILES: CC1=NN(c2ccccc2)C(=O)/C1=N\Nc1ccccc1] |
| Disperse Yellow 82 | 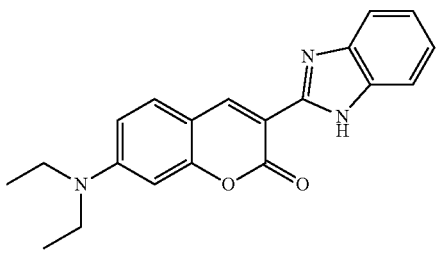 [SMILES: CCN(CC)c1ccc2cc(-c3nc4ccccc4[nH]3)c(=O)oc2c1] |
| Disperse Yellow 54 | 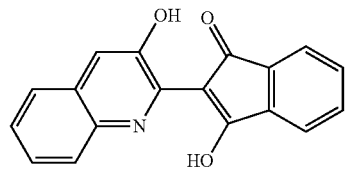 [SMILES: O=C1C(c2nc3ccccc3cc2O)=C(O)c2ccccc21] |
| Solvent Yellow 29 | 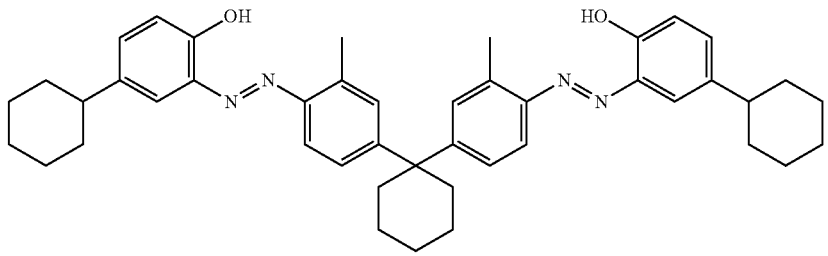 [SMILES: Cc1cc(C2(c3ccc(/N=N/c4cc(C5CCCCC5)ccc4O)c(C)c3)CCCCC2)ccc1/N=N/c1cc(C2CCCCC2)ccc1O] |
| Solvent Yellow 163 | 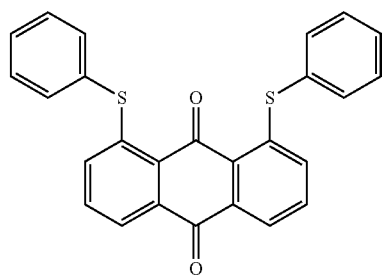 [SMILES: O=C1c2cccc(Sc3ccccc3)c2C(=O)c2c(Sc3ccccc3)cccc21] |

| Dye | Chemical structure |
|---|---|
| Solvent Yellow 3 | 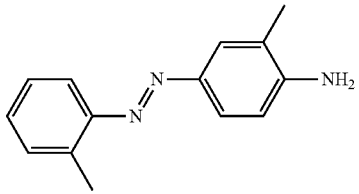 [SMILES: Cc1cc(/N=N/c2ccccc2C)ccc1N] |
| Solvent Yellow 56 | 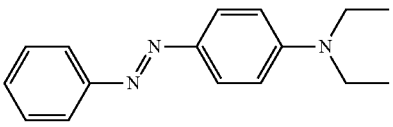 |
| Solvent Yellow 18 | 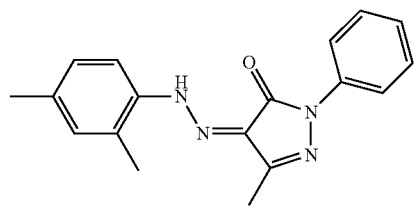 [SMILES: CC1=NN(c2ccccc2)C(=O)/C1=N\Nc1ccc(C)cc1C] |
| Solvent Yellow 98 | 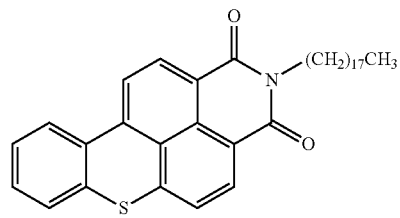 |
| Solvent Yellow 12 | 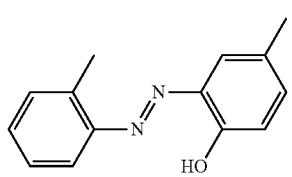 [SMILES: Cc1ccc(O)c(/N=N/c2ccccc2C)c1] |
| Solvent Yellow 14 | 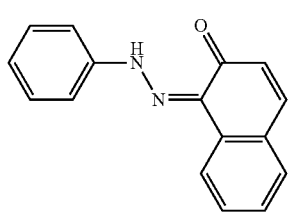 [SMILES: O=C1C=Cc2ccccc2/C1=N/Nc1ccccc1] |
| Disperse Red 13 | 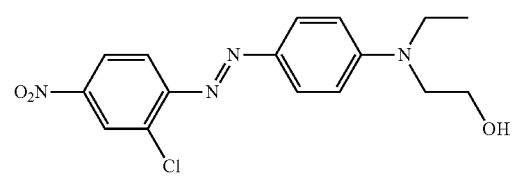 [SMILES: CCN(CCO)c1ccc(/N=N/c2ccc([N+](=O)[O-])cc2Cl)cc1] |
| Disperse Green 9 | 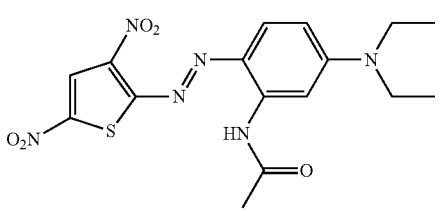 [SMILES: CCN(CC)c1ccc(/N=N/c2sc([N+](=O)[O-])cc2[N+](=O)[O-])c(NC(C)=O)c1] |

| Dye | Chemical structure |
|---|---|
| Disperse Blue 148 | 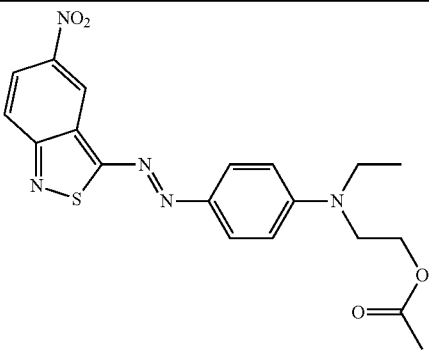 |
| Disperse Violet 63 | 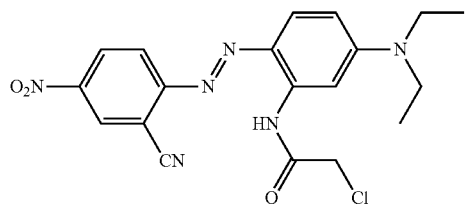 [SMILES: CCN(CC)c1ccc(/N=N/c2ccc([N+](=O)[O-])cc2C#N)c(NC(=O)CCl)c1] |
| Disperse Blue 60 | 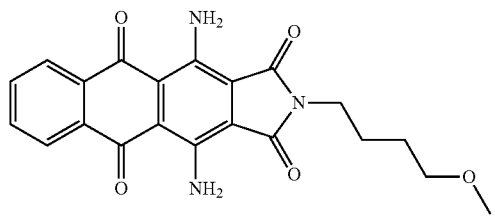 [SMILES: COCCCCn1c(=O)c2c(N)c3c(=O)c4ccccc4c(=O)c3c(N)c2c1=O] |
| Solvent Orange 15 | 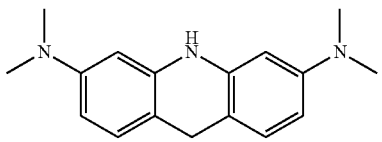 |

Preferably, the pigments and/or dyes that are sparingly soluble or insoluble in standard aqueous-alcoholic supports such as water, and especially the pigment(s) and/or direct dye(s) with a solubility of less than 20 grams per liter of water, are chosen from carbon black;

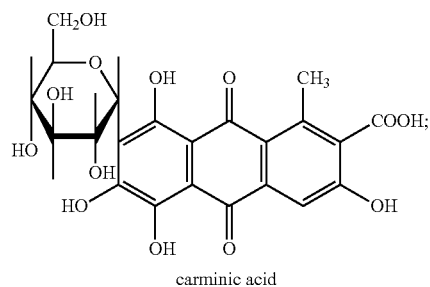

carminic acid

-continued

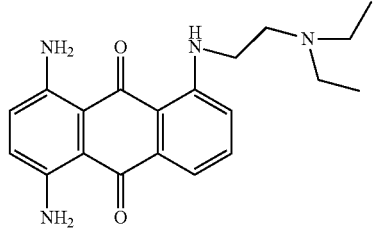

(A)

(A')

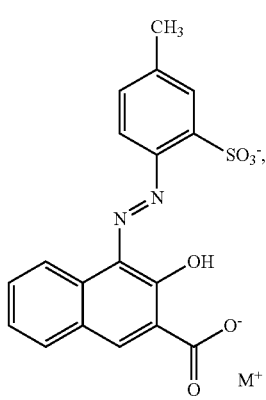

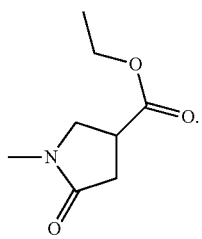

with M⁺ representing a cationic counterion, particularly an alkali metal or alkaline-earth metal, preferentially an alkaline-earth metal such as Ca⁺⁺

(B)

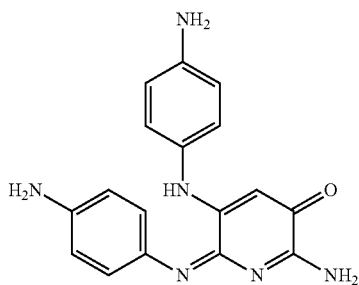

Carminic acid, the compounds (A), (A') and (B) and also the organic or mineral acid or base salts thereof, optical isomers thereof: stereoisomers or enantiomers and diastereoisomers, geometrical isomers and tautomers thereof, and solvates thereof such as hydrates;

The hydrophobic direct dye(s) may be present in the composition in an amount of between 0.001% and 5% by weight approximately relative to the total weight of the composition.

Cosmetic Composition:

The dye(s) or pigment(s) according to the invention are other than phthalocyanins, and more particularly phthalocyanins comprising copper when the compound of formula (I) represents:

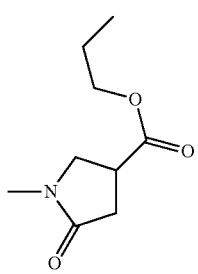

According to another particular embodiment of the invention, the composition is such that the dyeing(s) or pigment(s) according to the invention are other than phthalocyanins, and in particular phthalocyanins comprising copper when the compound of formula (I) represents:

The cosmetic composition according to the invention is cosmetically acceptable for dyeing keratin fibres, i.e. it comprises a dye support that generally contains water or a mixture of water and of one or more organic solvents or a mixture of organic solvents. Preferentially, the cosmetic composition of the invention contains water.

As mentioned previously, the dye support is aqueous-alcoholic. This support preferentially contains only water. According to one particularly advantageous embodiment of the invention, the cosmetic composition is formed i) from at least one compound of formula (I) as defined previously, ii) from at least one pigment or direct dye as defined previously, and iii) from water.

The term "organic solvent" means an organic substance that is capable of dissolving or dispersing in another substance without chemically modifying it.

The Organic Solvents:

Examples of organic solvents that may be mentioned include $C_1$-$C_4$ lower alcohols, such as ethanol and isopropanol; polyols and polyol ethers such as 2-butoxyethanol, propylene glycol, dipropylene glycol, propylene glycol monomethyl ether, diethylene glycol monoethyl ether and monomethyl ether, hexylene glycol, and also aromatic alcohols, for instance benzyl alcohol or phenoxyethanol.

The organic solvents are present in proportions preferably of between 1% and 40% by weight approximately and even more preferentially between 5% and 30% by weight approximately relative to the total weight of the dye composition.

According to one particular embodiment of the invention, the composition contains as support water and no organic solvents other than those of formula (I) or (Ia) as defined previously.

Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

Said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

The Additional Dyes:

The composition comprising one or more pigments and/or one or more direct dyes that are sparingly soluble or insoluble in aqueous-alcoholic solvents as defined previously may also comprise one or more additional direct dyes. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes other than pigments and/or one or more direct dyes that are sparingly soluble or insoluble in aqueous-alcoholic solvents, neutral, acidic or cationic quinone and in particular anthraquinone direct dyes, azine, triarylmethane, indoamine, methine, styryl, porphyrin, metalloporphyrin, phthalocyanine, cyanine and methine direct dyes, and fluorescent dyes.

Among the natural direct dyes, mention may be made of lawsone, juglone, indigo, isatin, curcumin, spinulosin, apigenidin and orceins. Extracts or decoctions containing these natural dyes and especially henna-based poultices or extracts, may also be used.

The additional direct dye(s) used in the composition preferably represent from 0.001% to 10% by weight approximately relative to the total weight of the composition(s), and even more preferentially from 0.05% to 5% by weight approximately.

The cosmetic composition according to the invention comprising one or more pigments and/or one or more direct dyes that are sparingly soluble or insoluble in aqueous-alcoholic solvents as defined previously may also use or comprise one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The oxidation base(s) present in the dye composition(s) are each generally present in an amount of between 0.001% and 10% by weight relative to the total weight of the corresponding compositions.

According to another particular embodiment of the invention, the composition according to the invention does not contain any oxidation base.

According to yet another embodiment, the composition does not contain any coupler. Preferentially, the composition according to the invention does not contain any oxidation base or any couplers of aromatic amine type.

The cosmetic composition of the invention may be in various galenical forms, such as a powder, a lotion, a mousse, a cream or a gel, or in any other form that is suitable for dyeing keratin fibres. It may also be conditioned in a pump-dispenser bottle without propellant or under pressure in an aerosol can in the presence of a propellant and form a foam.

The pH of the Composition

According to one particular mode of the invention, the pH of the composition containing the pigment(s) and/or one or more direct dye(s) that are sparingly soluble or insoluble in aqueous-alcoholic solvents is between 3 and 12, preferentially between 3 and 10.5 and even more preferentially in the region of neutrality, i.e. between 6 and 8.

The pH of the composition according to the invention may be adjusted to the desired value by means of acidifying or basifying agents usually used in the dyeing of keratin fibres, or alternatively using standard buffer systems.

Among the acidifying agents for the compositions used in the invention, examples that may be mentioned include mineral or organic acids, for instance hydrochloric acid, orthophosphoric acid or sulfuric acid, carboxylic acids, for instance acetic acid, tartaric acid, citric acid and lactic acid, and sulfonic acids.

The Basifying Agents:

The basifying agent may be aqueous ammonia. Preferentially, the basifying agent is chosen from alkanolamines such as monoethanolamine, diethanolamine and triethanolamine, alkali metal carbonate salts, guanidine, imidazole, sodium hydroxide, potassium hydroxide or calcium hydroxide, arginine, and the compounds of formula (II) below:

(II)

in which formula (II):

W is a propylene residue optionally substituted with a hydroxyl group or a $C_1$-$C_4$ alkyl radical;

$R_a$, $R_b$, $R_c$ and $R_d$, which may be identical or different, represent a hydrogen atom or a $C_1$-$C_4$ alkyl or $C_1$-$C_4$ hydroxyalkyl radical.

More particularly, the basifying agent(s) are chosen from ethanolamine, carbonate salts, guanidine, imidazole, calcium hydroxide and arginine.

Process of Dyeing in One or More Steps

One subject of the invention concerns a process of dyeing by treating or applying to keratin materials i) one or more compounds of formula (I) or (Ia) as defined previously and ii) one or more pigments and/or one or more direct dyes that are sparingly soluble or insoluble in aqueous-alcoholic solvents, the ingredients i) and ii) possibly being applied to the materials either simultaneously in one step, or successively in several steps.

According to one preferred mode of the dyeing process of the invention, the ingredients i) and ii) are applied in one step. In this case, preferentially, the ingredients i) and ii) are together in a cosmetic composition, which is then applied to the keratin fibres.

According to one preferred mode of the process according to the invention, the process does not use any oxidation bases or couplers.

The leave-on time for coloration to be achieved is between 3 and 120 minutes. Preferentially, after application of the composition containing the direct dye(s) and/or the pigment(s) that are sparingly soluble or insoluble in aqueous-alcoholic solvents, the composition is left to act for 10 to 60 minutes.

Irrespective of the application method, the application temperature is generally between room temperature and 80° C. and more particularly between 15° C. and 45° C. Thus, it is advantageously possible, after application of the composition(s) comprising ingredients i) and ii) as defined previously, to subject the head of hair to a heat treatment by heating to a temperature of between 30 and 60° C. In practice, this operation may be performed using a styling hood, a hairdryer, an infrared ray dispenser or other standard heating appliances.

A heating iron at a temperature of between 60 and 220° C. and preferably between 120 and 200° C. may be used, both as heating means and as hair straightening means.

One particular mode of the invention concerns a dyeing process that it is performed at room temperature (25° C.).

After applying ingredients i) and ii) as defined previously to the keratin fibres, the said locks are preferentially rinsed with water, washed with standard shampoo and dried by means that have been described previously.

According to a particular dyeing process of the invention, the composition comprising ingredients i) and ii) is applied in a single step to the keratin fibres, particularly the hair, and is then left on for between 15 and 60 minutes, preferentially 30 minutes, and the said fibres are then rinsed with water, washed with standard shampoo and dried.

In all the particular modes and variants of the processes described previously, the compositions mentioned are ready-to-use compositions that may result from the extemporaneous mixing of two or more compositions and especially of compositions present in dyeing kits.

Dyeing Device or "Kit":

Another subject of the invention is a multi-compartment dyeing device or "kit". Advantageously, this device comprises from 2 to 5 compartments containing from 2 to 5 compositions in which are distributed the following ingredients:

i) one or more compounds of formula (I) or (Ia) as defined previously, and ii) one or more pigments and/or one or more direct dyes that are sparingly soluble or insoluble in aqueous-alcoholic solvents.

The compositions of the device according to the invention are conditioned in separate compartments, optionally accompanied by suitable application means, which may be identical or different, such as fine brushes, coarse brushes or sponges.

This device mentioned above may also be equipped with a means for dispensing the desired mixture on the hair, such as the devices described in patent FR 2 586 913.

The non-limiting examples that follow illustrate the invention without limiting its scope.

EXAMPLES OF DYEING

Dye (A) was prepared from 1,4-diamino-5-nitroanthracene-9,10-dione and N,N-diethylethane-1,2-diamine in the presence of sodium hydroxide. Dye (B) was prepared by reacting 2-aminopyridin-3-ol with benzene-1,4-diamine in the presence of aqueous hydrogen peroxide solution at basic pH. Pigment (C) is commercially available. 1-n-Butyl-4-ethoxycarbonylpyrrolidin-2-one belonging to formula (I) was prepared by condensation of diethyl itaconate with N-butylamine.

Example 1

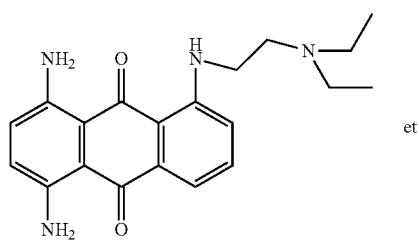

(A)

et

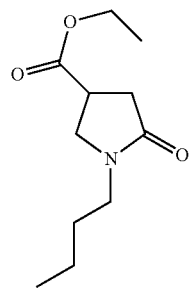

A composition 1 comprising 10% by weight (0.047 mol per 100 g of formula) of ethyl 1-butyl-5-oxopyrrolidine-3-carboxylate, 0.17% by weight (0.048 mmol per 100 g of formula) of 1,4-diamino-5-{[2-(diethylamino)ethyl]amino}anthra-9,10-quinone and water (qs 100) is applied for 30 minutes at 20° C. to a lock of natural hair containing 90% white hairs.

After the leave-on time, the lock is rinsed, shampooed and dried. It is dyed a strong blue colour.

A comparative composition 1c comprising 0.17% by weight of 1,4-diamino-5-{[2-(diethylamino)ethyl]amino}anthra-9,10-quinone and 50/50 water/ethanol (qs 100) is applied for 30 minutes at 20° C. to a lock of natural hair containing 90% white hairs, of the same batch.

The colour of the locks was evaluated in the CIE L* a* b* system, using a Konica-Minolta cm2600d spectrocolorimeter.

The ΔE colour uptake is calculated from the measured L*a*b* values. In this L*a*b* system, L* represents the intensity of the colour, a* indicates the green/red colour axis and b* the blue/yellow colour axis.

The lower the value of L*, the darker or more intense the colour.

The colour uptake on the keratin fibres is evaluated according to ΔE, which is the colour variation between natural dyed fibres and natural undyed fibres; the greater the "uptake", the more the fibres are dyed.

$$\Delta E=\sqrt{(L^*-L_o^*)^2+(a^*-a_o^*)^2+(b^*-b_o^*)^2}$$

In this equation, L*, a* and b* represent the values measured on the dyeing keratin fibres and $L_o^*$, $a_o^*$ and $b_o^*$ represent the values measured on the undyed keratin fibres.

Measurement Results:

The uptakes after coloration using the composition according to the invention (composition 1) and that of the comparative composition (composition 1c) were compared as follows:

| | L* (D65) | a* (D65) | b* (D65) | Colour "uptake" ΔE |
|---|---|---|---|---|
| Undyed lock | 58.1 | 1.56 | 13.98 | |
| Lock dyed with composition 1 (invention) | 30.04 | 0.23 | −9.09 | 36.37 |
| Lock dyed with composition 1c (comparative) | 39.24 | −0.52 | −2.34 | 25.03 |

The uptake on the keratin fibres is significantly greater with the composition of the invention containing the pyrrolidine derivative of formula (I) or (Ia), the lock dyed with this composition is much more intense, powerful and chromatic (blue) than the lock dyed with the comparative composition.

A series of 10 washes applied to the lock dyed with the composition according to the invention led to a mild degradation of the colour (less than 10%). The coloration obtained with the composition of the invention is much more remanent than that of the comparative composition.

Example 2

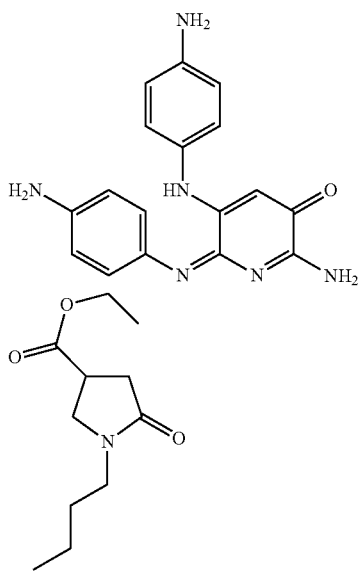
(B)

A composition 2 comprising 10% by weight (0.047 mol per 100 g of formula) of ethyl 1-butyl-5-oxopyrrolidine-3-carboxylate, 0.16% by weight (0.5 mmol per 100 g of formula) of 2-amino-5-[(4-aminophenyl)amino]-6-[(4-aminophenyl)imino]pyridin-3(6H)-one and water (qs 100) is applied for 30 minutes at room temperature to a lock of natural hair containing 90% white hairs.

A comparative composition 2c comprising 0.16% by weight of 2-amino-5-[(4-aminophenyl)amino]-6-[(4-aminophenyl)imino]pyridin-3(6H)-one and 50/50 water/ethanol (qs 100) is applied for 30 minutes at room temperature to a lock of natural hair containing 90% white hairs, of the same batch.

After applying, the locks are rinsed, shampooed and dried.
Measurement Results:

The uptakes after coloration using the composition according to the invention (composition 2) and that of the comparative composition (composition 2c) were compared as follows:

|  | L* (D65) | a* (D65) | b* (D65) | Colour "uptake" ΔE |
|---|---|---|---|---|
| Undyed lock | 49.03 | 1.09 | 10.5 |  |
| Lock dyed with composition 2 (invention) | 36.81 | 6.62 | 8.22 | 13.61 |
| Lock dyed with composition 2c (comparative) | 40.94 | 4.6 | 8.47 | 9.05 |

As for Example 1, it is observed that the uptake on the keratin fibres is significantly greater with the composition of the invention containing the pyrrolidine derivative of formula (I) or (Ia), the lock dyed with this composition is much more intense, powerful and chromatic (brown) than the lock dyed with the comparative composition.

Example 3

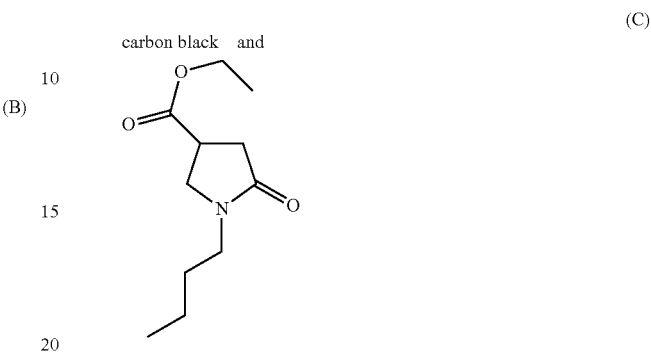
(C)

carbon black and

A composition comprising 1 ml of ethyl 1-butyl-5-oxopyrrolidine-3-carboxylate, 1 ml of water and 50 mg of carbon nanopowder (Aldrich) is applied for 30 minutes at room temperature to a lock of 0.5 g of natural hair containing 90% white hairs. After the leave-on time, the locks are rinsed, shampooed and dried. They are dyed a grey-black colour.
Results:

|  | L* (D65) | a* (D65) | b* (D65) | Colour "uptake" ΔE |
|---|---|---|---|---|
| Undyed lock | 57.78 | −0.21 | 12.24 |  |
| Lock dyed with composition 3 (invention) | 39.42 | 0.42 | 6.39 | 19.27 |

A sharp colour uptake is observed on the keratin fibres with composition 3 comprising carbon black and the compound of formula (I) or (Ia) according to the invention.

The invention claimed is:
1. A composition comprising, in a suitable cosmetic medium:
i) at least one 2-pyrrolidinone functionalized in position 4 with an ester or amide, chosen from compounds of formula (I):

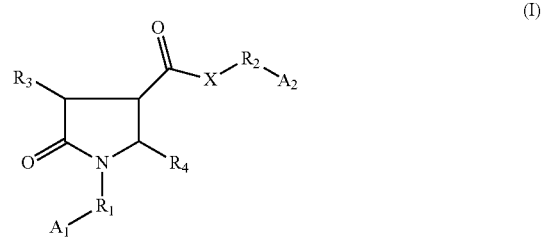
(I)

and the organic or mineral acid or base salts thereof, optical isomers thereof, stereoisomers or enantiomers and diastereoisomers, geometrical isomers and tautomers thereof, and solvates and hydrates thereof;
wherein in formula (I):
X is chosen from oxygen and divalent amino groups —N($R_5$)—; wherein $R_5$ is chosen from hydrogen, linear or branched ($C_1$-$C_{30}$) alkyl groups optionally substituted with at least one group chosen from —OH, —SH, —NH$_2$, tri(C$_1$-C$_6$)alkylammoniums, and cationic heteroaryl groups;

R$_1$ and R$_2$, which may be identical or different, are chosen from:
a) optionally substituted hydrocarbon-based chains, wherein the hydrocarbon-based chain is a saturated linear C$_1$-C$_{30}$ or branched C$_3$-C$_{30}$ or cyclic C$_3$-C$_7$ chain; and wherein the hydrocarbon-based chain is optionally interrupted with:
  i) at least one heteroatom chosen from —O—, —N(R$_6$)— or —S—;
  ii) at least one group chosen from —S(O)—, —S(O)$_2$—, —C(O)—, and —N$^+$(R$_6$)(R$_7$)—; a combination of i) and ii); and/or
  iii) a 3- to 6-membered saturated or unsaturated carbon-based ring optionally substituted with one or more identical or different radicals chosen from hydroxyl (OH) and amino (—NRR');
b) divalent chains -Cycl-Alk-Cycl'- wherein:
  Cycl and Cycl', which may be identical or different, are chosen from cyclic hydrocarbon-based chains, and
  Alk is chosen from substituted or unsubstituted (C$_1$-C$_6$) alkylene chains;
c) optionally substituted hydrocarbon-based chains, wherein the hydrocarbon-based chain is a saturated linear C$_2$-C$_{30}$ or branched C$_3$-C$_{30}$ or cyclic C$_3$-C$_7$ chain; and wherein the hydrocarbon-based chain is optionally interrupted with:
  i) at least one heteroatom chosen from —O—, —N(R$_6$)— or —S—;
  ii) at least one group chosen from —S(O)—, —S(O)$_2$—, —C(O)—, and —N$^+$(R$_6$)(R$_7$)—; a combination of i) and ii); and/or
  iii) a 3- to 6-membered saturated or unsaturated carbon-based ring optionally substituted with one or more identical or different radicals chosen from hydroxyl (OH) and amino (—NRR');

R$_1$ and/or R$_2$ substituted with at least one radical chosen from those of formulas (E) and (F):

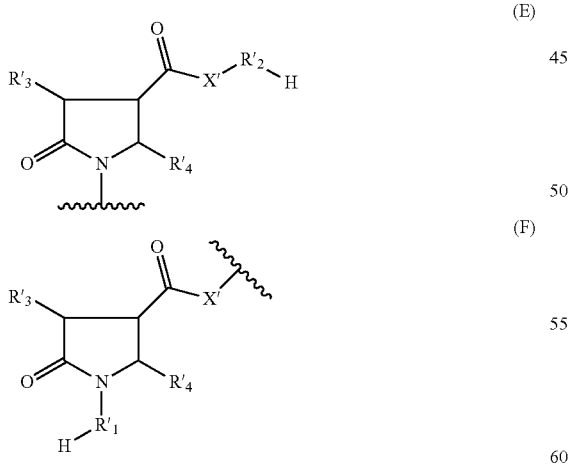

wherein in formulas (E) and (F):
X' is chosen from oxygen —O— and —N(R$_5$) groups;
R'$_1$, and R'$_2$, which may be identical or different, are as defined for R$_1$ and R$_2$, but cannot be substituted with the radicals (E) or (F):

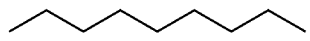

represents the point of attachment of the radicals (E) and (F) to the rest of the molecule;

A$_1$ and A$_2$, which may be identical or different, are chosen from: hydrogen, and groups chosen from a) —OH; b) —SH; c) —NRR'; d) —O—P(O)(OH)$_2$; e) —O—S(O)$_2$OH; f) —S(O)$_2$OH; g) —C(O)OH; h) saturated or unsaturated 3- to 6-membered (hetero)cycles optionally substituted with at least one identical or different radical chosen from (hydroxy)(C$_1$-C$_6$) alkyl, hydroxyl and —NRR', the (hetero)cycles possibly being cationic; i) —N$^+$(R$_7$)(R$_8$)(R$_9$); j) RR'N—C(=NR")—N(R)— and

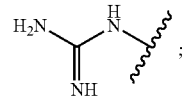

and
k) radicals of formula (G) or (H):

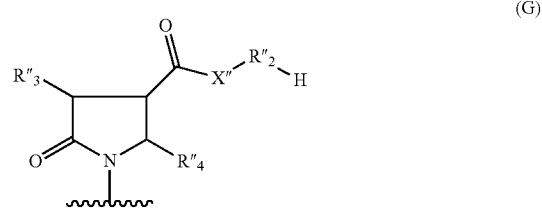

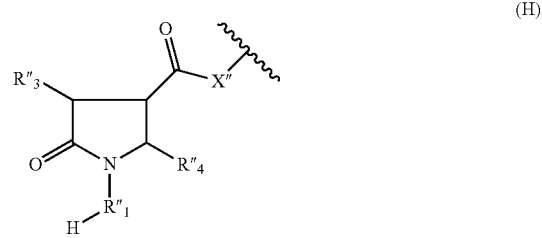

wherein in formulas (G) and (H):
X" is chosen from oxygen —O— and —N(R$_5$) groups;
R"$_1$, and R"$_2$, which may be identical or different, are as defined for R'$_1$, and R'$_2$,
wherein A$_1$ and A$_2$ do not simultaneously represent a radical (G) or (H);
R$_3$, R$_4$, R'$_3$, R'$_4$, R"$_3$ and R"$_4$, which may be identical or different, are chosen from hydrogen and linear C$_1$-C$_{12}$ or branched C$_3$-C$_{12}$ alkyl chains;
R$_6$ is chosen from hydrogen and linear (C$_1$-C$_{20}$) alkyl or branched (C$_3$-C$_{20}$) alkyl groups, optionally substituted with a radical (G) or (H);
R$_7$, R$_8$ and R$_9$, which may be identical or different, are chosen from hydrogen and (C$_1$-C$_6$) alkyl groups optionally substituted with at least one hydroxyl group; and
R, R' and R", which may be identical or different, are chosen from hydrogen atom and (C$_1$-C$_{18}$) alkyl groups optionally substituted with at least one hydroxyl group;

wherein when $A_1$, $A_2$, $R_1$, $R_2$, and/or $R_5$ contain or denote a cationic group, the electrical neutrality of the compounds of formula (I) is ensured by an anionic counterion or a mixture of anionic counterions; and ii) at least one colorant chosen from direct dyes, wherein the at least one colorant is sparingly soluble or insoluble in standard aqueous-alcoholic supports.

2. The composition according to claim 1, wherein X, X' and X" are independently chosen from oxygen and amino groups —N($R_5$)—, wherein $R_5$ is chosen from hydrogen and ($C_1$-$C_6$) alkyl groups.

3. The composition according to claim 1, wherein $R_3$, $R_4$, $R'_3$, $R'_4$, $R''_3$ and $R''_4$ are hydrogen.

4. The composition according to claim 1, wherein $R_1$ is chosen from linear $C_1$-$C_{20}$ or branched $C_3$-$C_{20}$ saturated hydrocarbon-based chains optionally interrupted with at least one entity chosen from O, S, —N($R_6$)—, —N$^+$($R_6$)($R_7$)—, —N($R_6$)—C(O)—, —C(O)—N($R_6$)—, —N($R_6$)—C(O)—N($R_7$)— and —S—S—; and/or $R_1$ is optionally substituted with at least one identical or different radical chosen from hydroxyl (OH) and —NRR'.

5. The composition according to claim 1, wherein $R_6$ is chosen from ($C_1$-$C_6$) alkyl groups optionally substituted with a radical (G) and $R_7$ is chosen from hydrogen and ($C_1$-$C_6$) alkyl groups.

6. The composition according to claim 1, wherein $R''_2$ is chosen from ($C_1$-$C_4$) alkylene groups.

7. The composition according to claim 1, wherein $R_2$ is chosen from linear $C_1$-$C_{12}$ or branched $C_3$-$C_{12}$ saturated hydrocarbon-based chains optionally interrupted with at least one entity chosen from O, S, —N($R_6$)—, —N$^+$($R_6$)($R_7$)—, —N($R_6$)—C(O)—, —C(O)—N($R_6$)—, —N($R_6$)—C(O)—N($R_7$)— or —S—S—; and/or $R_2$ is optionally substituted with at least one identical or different radical chosen from hydroxyl (OH) and —NRR'.

8. The composition according to claim 1, wherein A1 is chosen from:
hydrogen,
OH,
S(O)$_2$OH,
NRR' radicals,
O—P(O)OH$_2$,
O—S(O)$_2$OH,
C(O)OH,
saturated or unsaturated 4- to 6-membered (hetero)cycles, the (hetero)cycles possibly being cationic, and
radicals of formula —N$^+$($R_7$)($R_8$)($R_9$) or (G).

9. The composition according to claim 1, wherein the compounds of formula (I) comprise at least one cationic group.

10. The composition according to claim 1, wherein the compounds of formula (I) comprise only one 2-pyrrolidinone unit functionalized in position 4 with a carboxylic acid or amide and does not comprise any radicals (E), (F), (G) or (H).

11. The composition according to claim 1, wherein X is oxygen; $R_3$, $R_4$, $A_1$ and $A_2$ are hydrogen; and $R_1$ and $R_2$, which may be identical or different, are chosen from linear $C_1$-$C_8$ or branched $C_3$-$C_8$ alkylene groups.

12. The composition according to claim 1, wherein $A_2$ is chosen from:
hydrogen,
OH,
saturated or unsaturated 4- to 6-membered (hetero)cycles, the (hetero)cycles possibly being cationic, and
radicals of formula: —N$^+$($R_7$)($R_8$)($R_9$).

13. The composition according to claim 1, wherein $R_2$ is chosen from saturated $C_1$-$C_{10}$ hydrocarbon-based chains optionally interrupted with at least one oxygen atom.

14. The composition according to claim 1, wherein the compounds of formula (I) are chosen from compounds of formula (I'a):

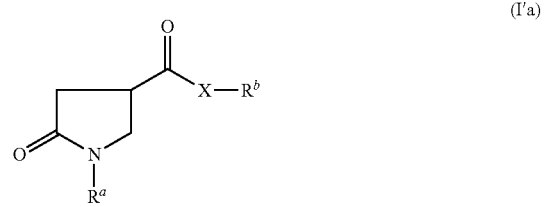

and the organic or mineral acid salts thereof, optical isomers thereof, stereoisomers, enantiomers and diastereoisomers thereof, and the solvates and hydrates thereof;
wherein in formula (I'a):
X is chosen from oxygen and divalent amino groups —N(R'$_5$)—; wherein R'$_5$ is chosen from hydrogen and linear or branched ($C_1$-$C_{20}$) alkyl groups;
$R^a$ is chosen from linear or branched ($C_2$-$C_{30}$) alkyl groups; and
$R^b$ is chosen from linear or branched ($C_1$-$C_{20}$) alkyl groups.

15. The composition according to claim 1, wherein the compounds of formula (I) comprise two or three 2-pyrrolidinone units functionalized in position 4 with a carboxylic acid or amide; wherein $R_1$ is chosen from divalent chains -alk-T-alk'- wherein:
T is chosen from:
a covalent bond σ,
a heteroatom,
N(R) groups, wherein R is chosen from hydrogen and ($C_1$-$O_6$) alkyl groups or -alk"-(E); and
divalent groups —$X_a$-alk"-$X_b$-wherein $X_a$ and $X_b$, which may be identical or different are chosen from heteroatoms and NH groups;
alk, alk' and alk", which may be identical or different, are chosen from ($C_1$-$C_6$) alkylene groups; and
$A_1$ is chosen from radicals of formula (G).

16. The composition according to claim 1, wherein the compounds of formula (I) are chosen from compounds a to ih and 1 to 108 below, the organic or mineral acid or base salts thereof, optical isomers thereof, stereoisomers or enantiomers, diastereoisomers, and tautomers thereof, and the solvates and hydrates thereof:

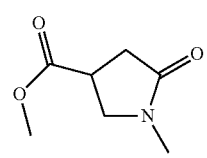

a

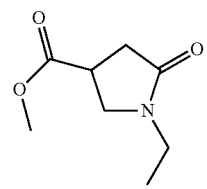

b

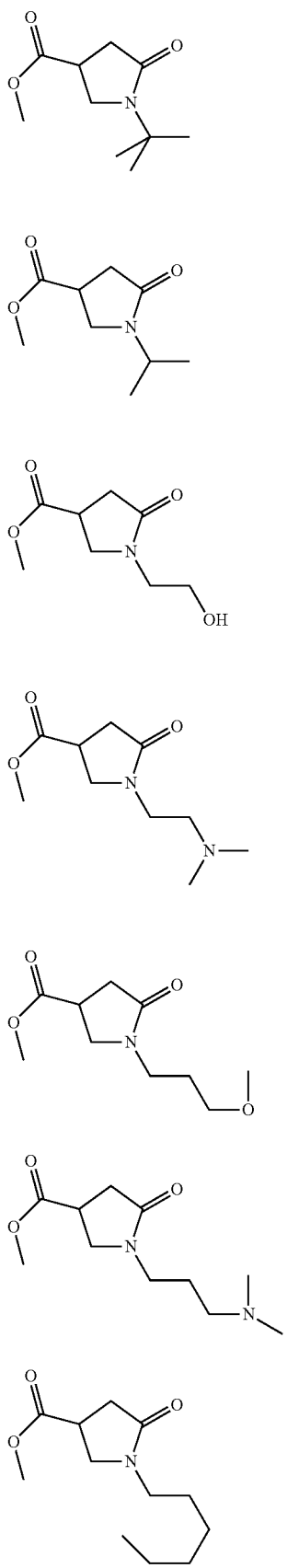
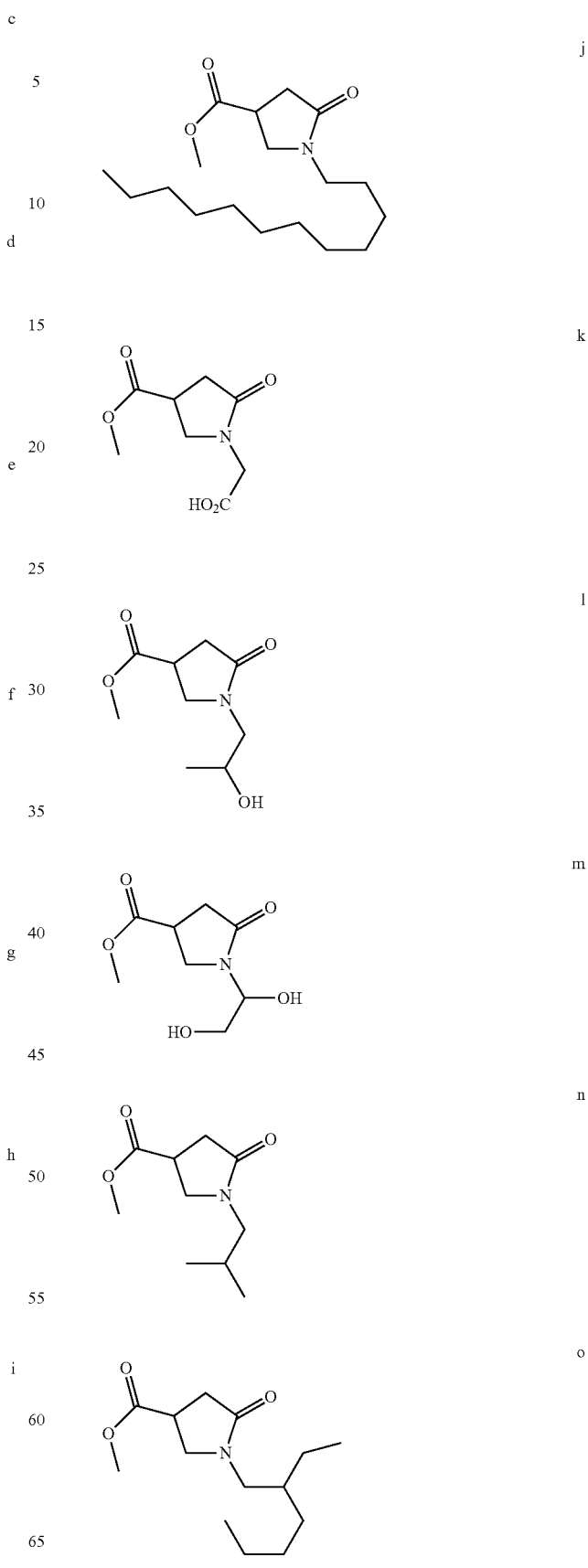

117
-continued
118
-continued
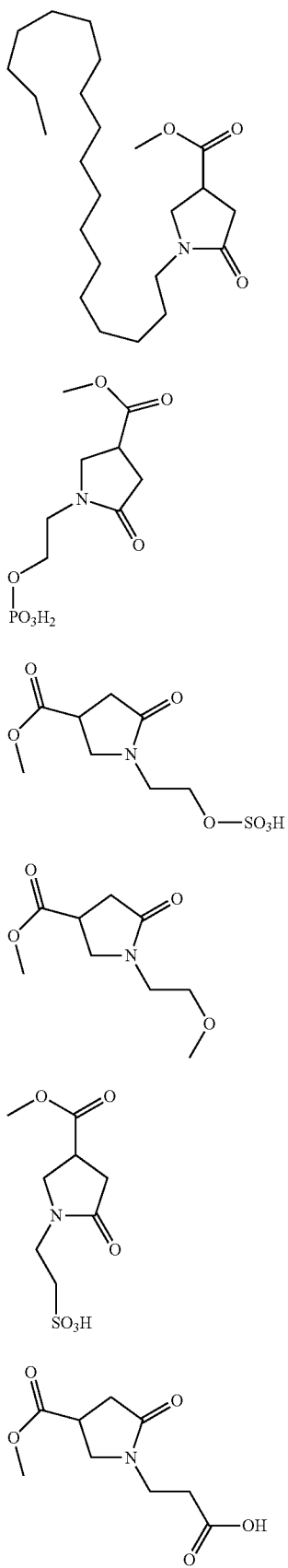
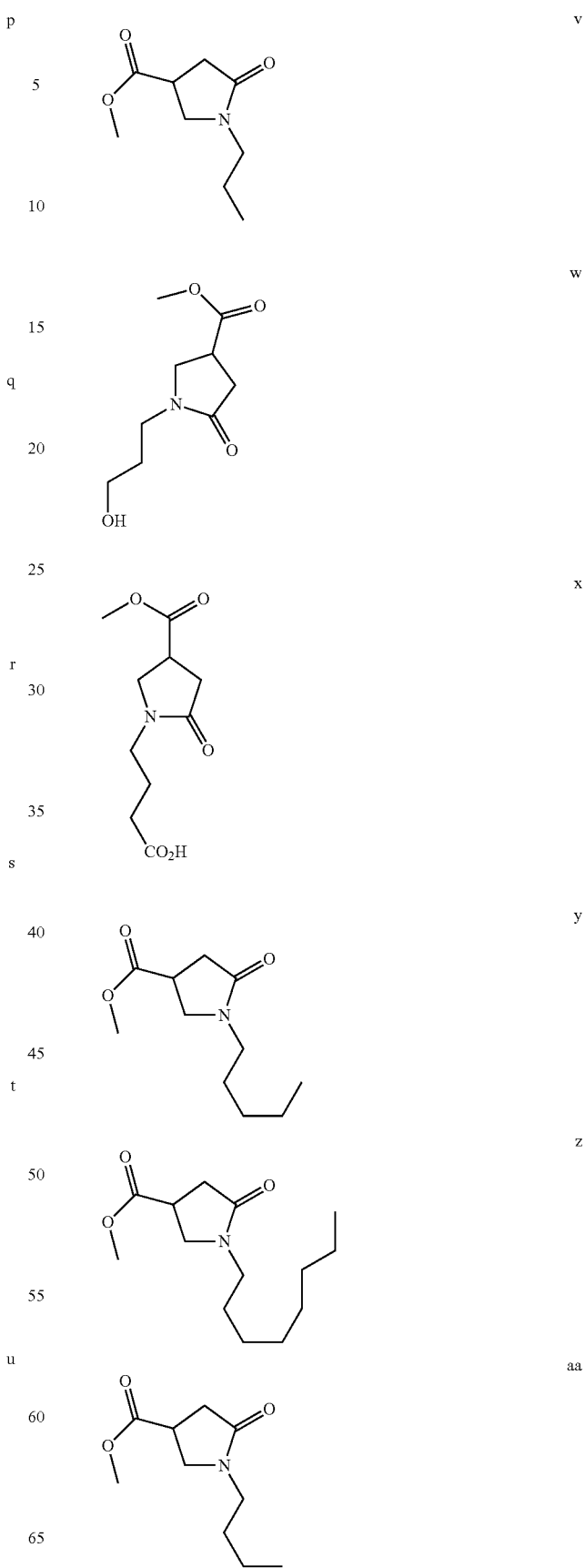

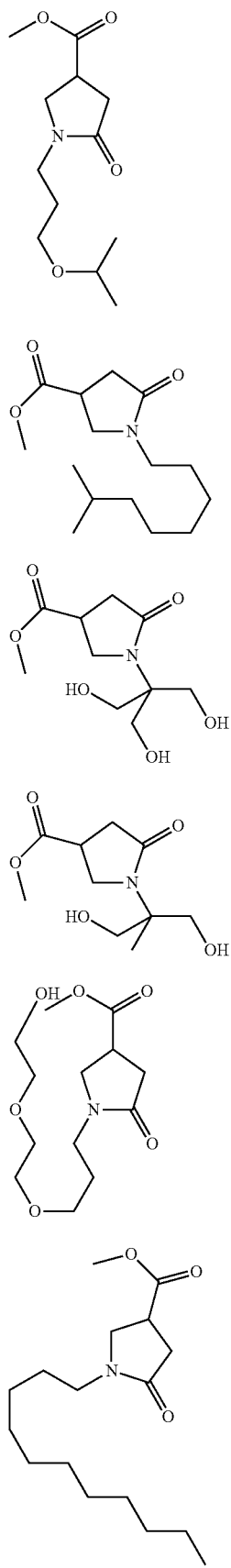
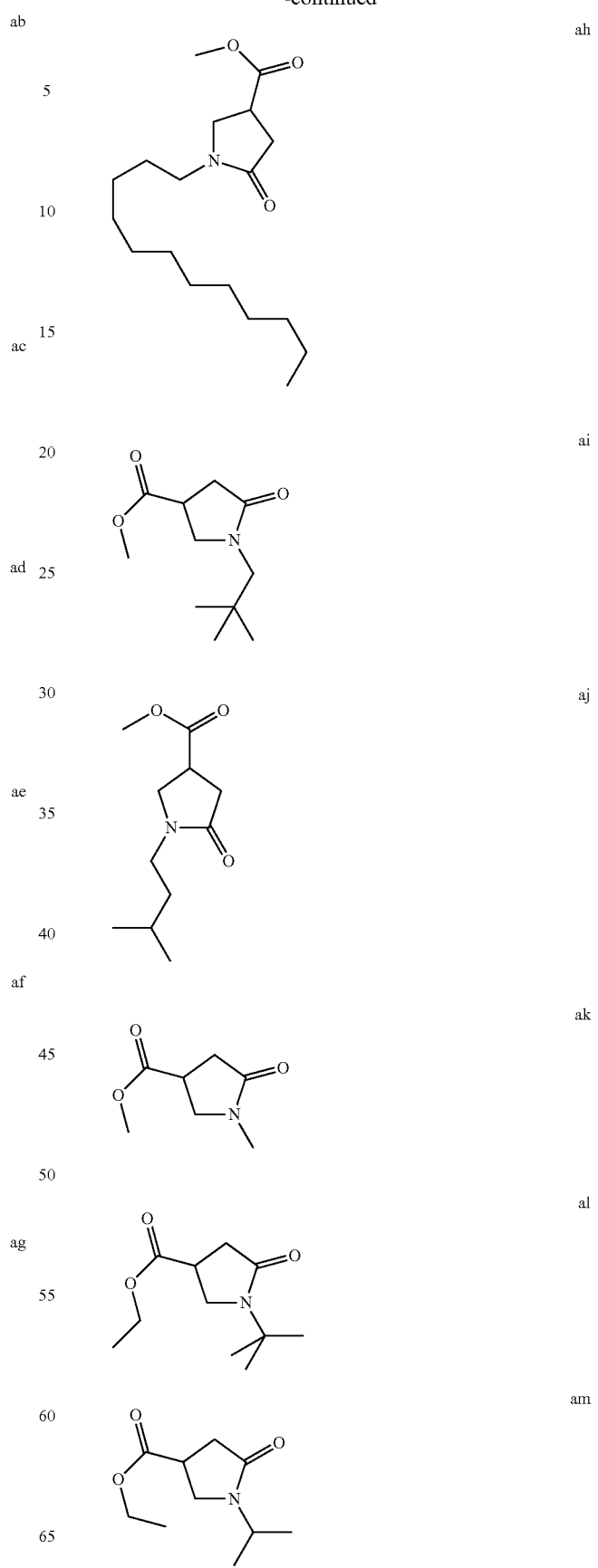

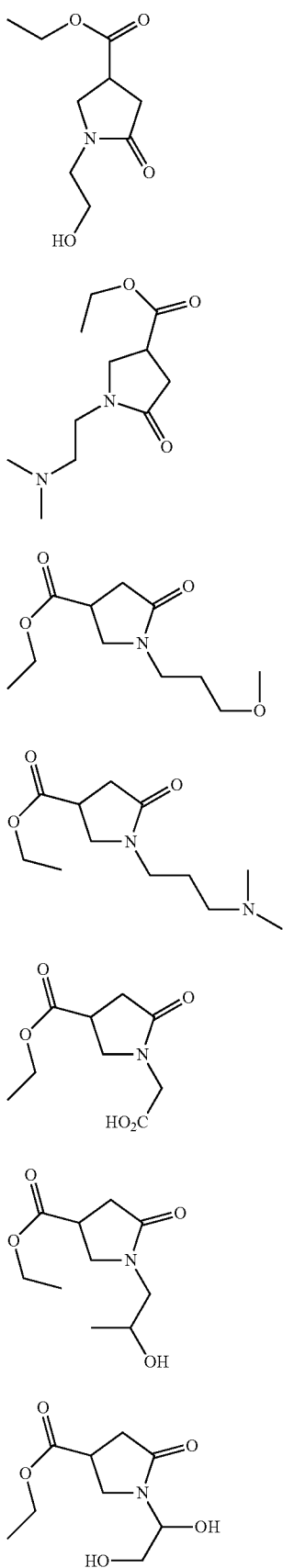
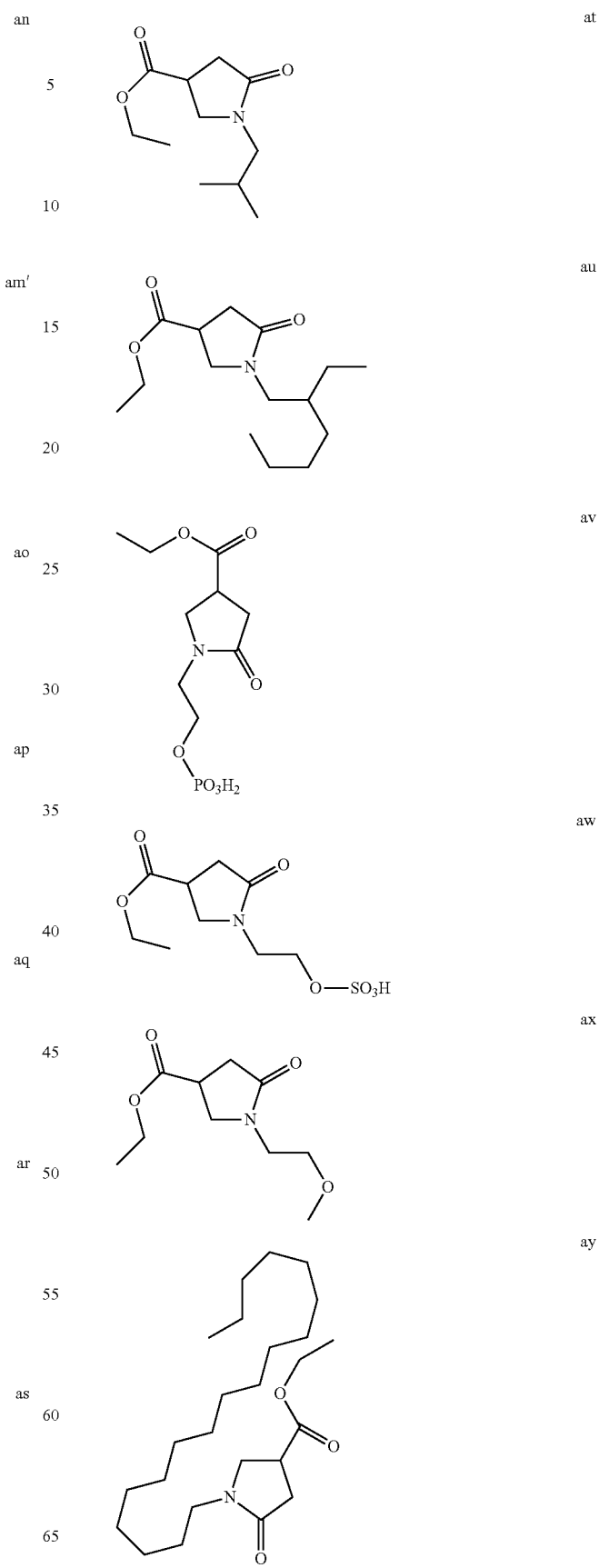

| 123 -continued | | 124 -continued | |
|---|---|---|---|
| 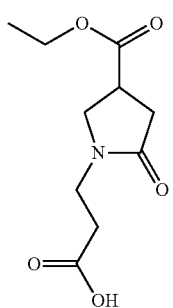 | | az 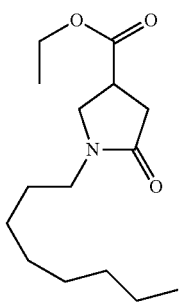 | be |
| 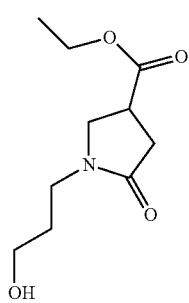 | ba | 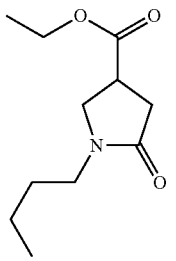 | bf |
| 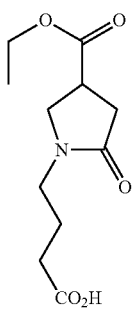 | bb | 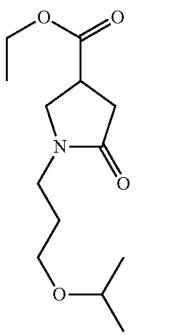 | bg |
| 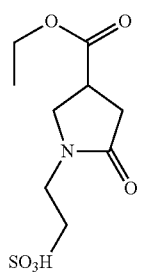 | bc | 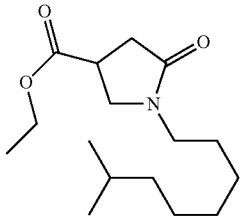 | bh |
| 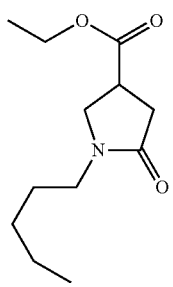 | bd | 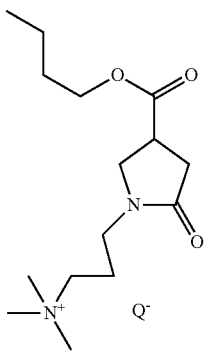 | bi |

125
-continued
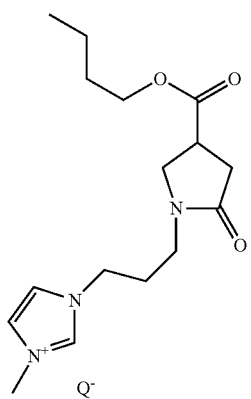
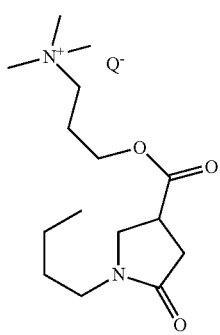
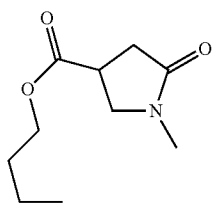
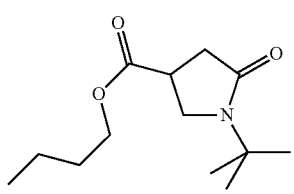
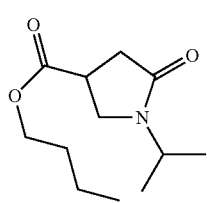
126
-continued
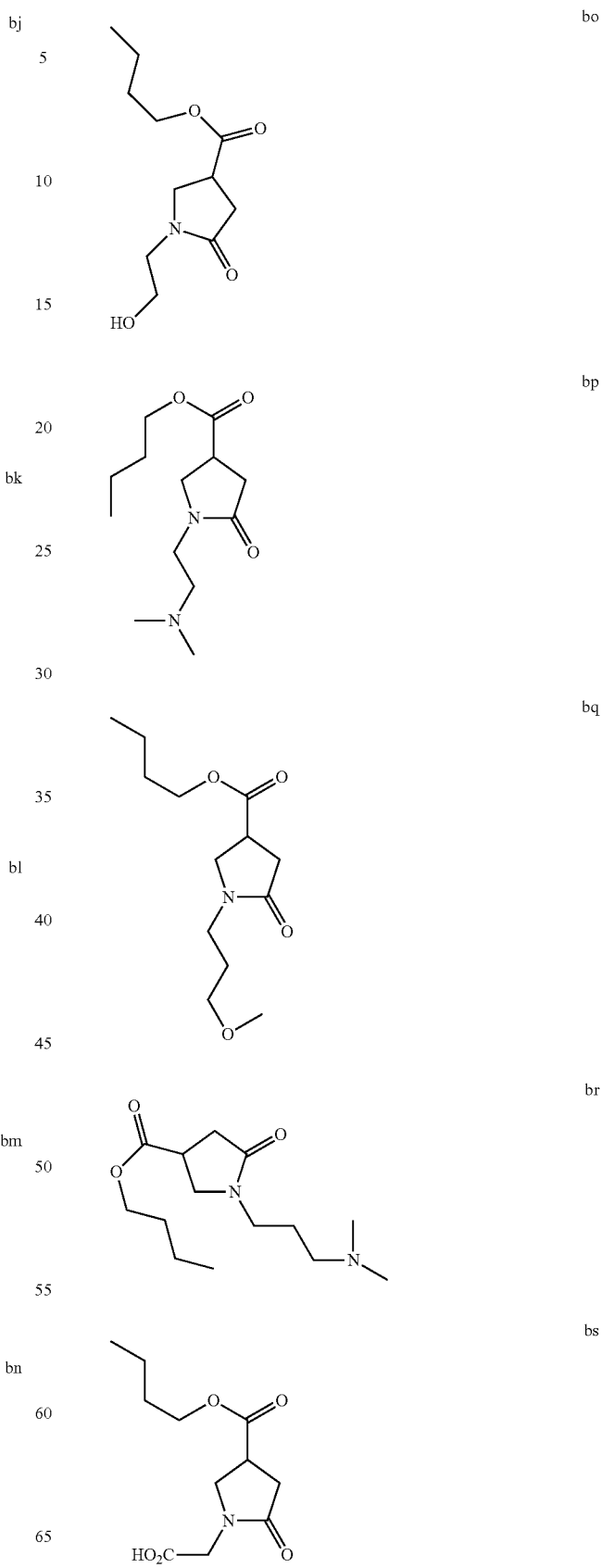

127
-continued
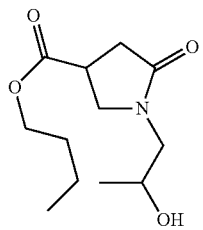
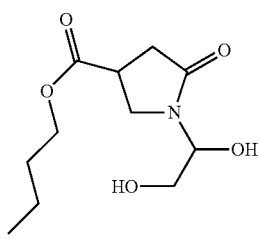
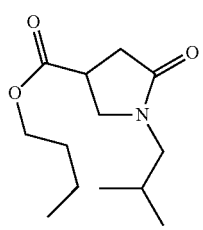
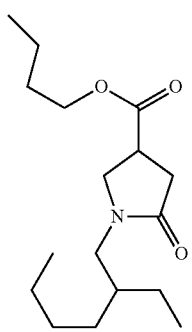
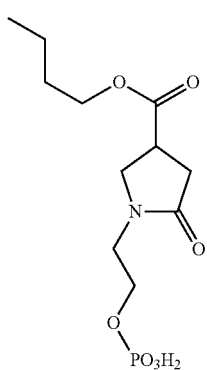
128
-continued
bt
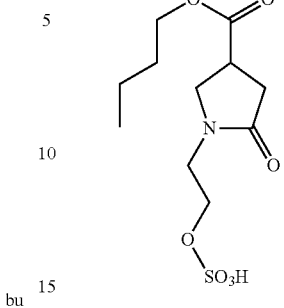
by
bu
bv
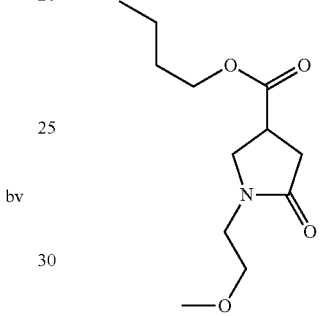
bz
bw
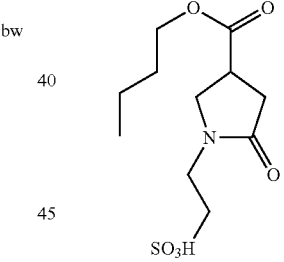
ca
bx
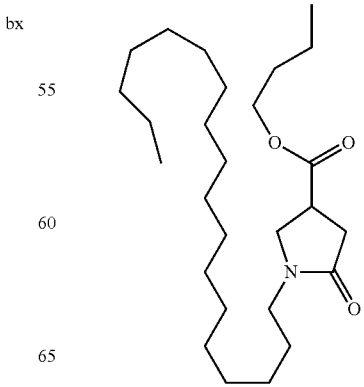
cb

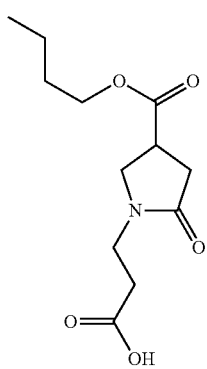
cc
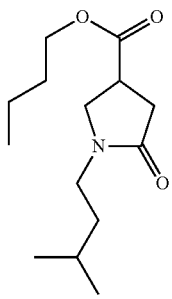
ch
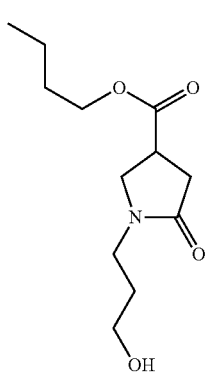
cd
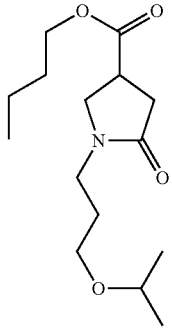
ci
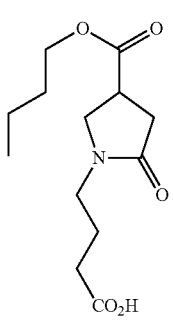
ce
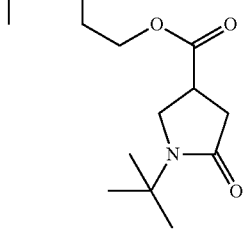
cj
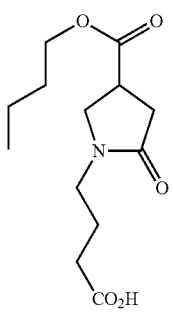
cf
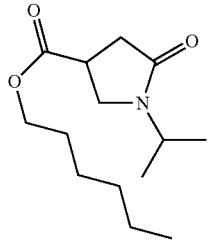
ck
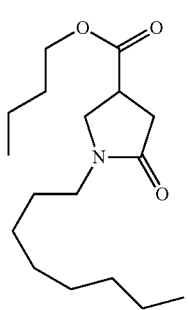
cg
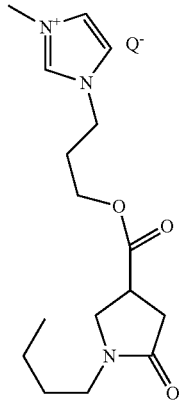
cl 131
-continued
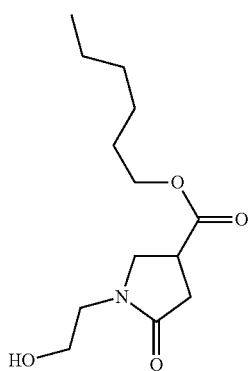
cm
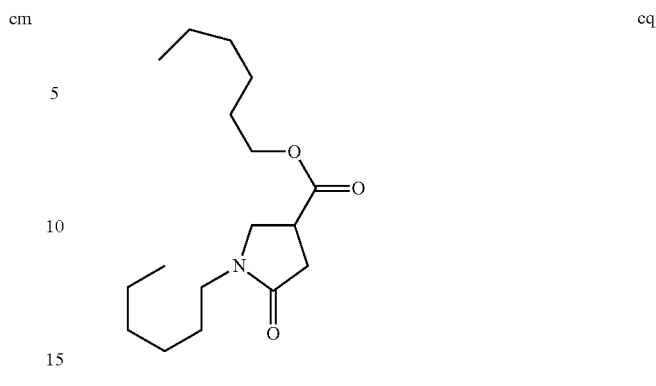
cq
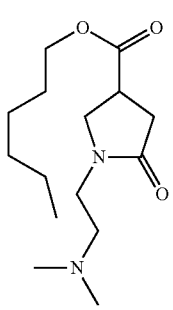
cn
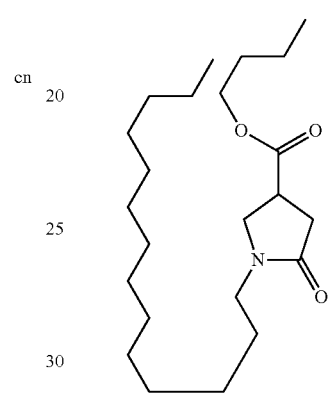
cr
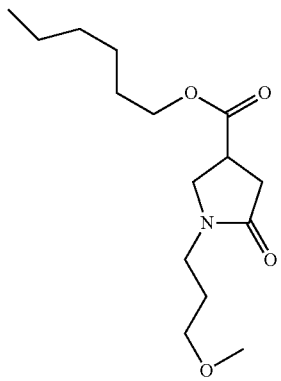
co
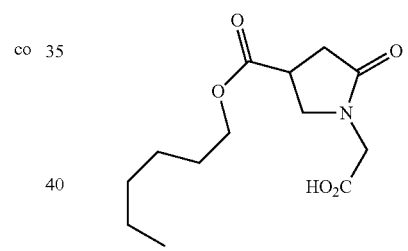
cs
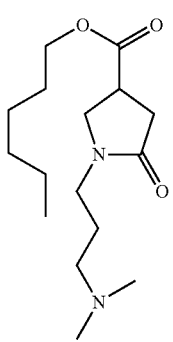
cp
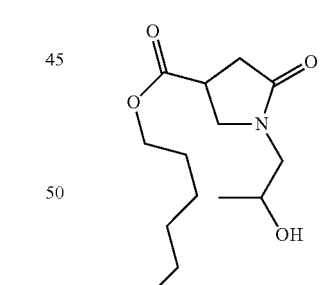
ct
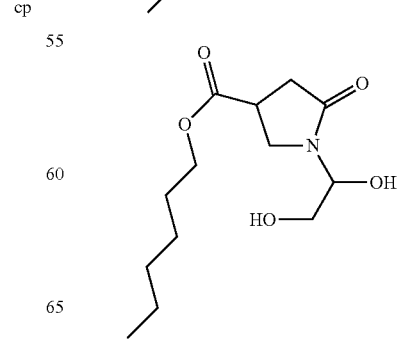
cu 133
-continued
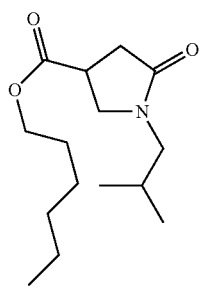
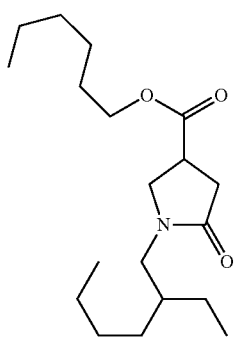
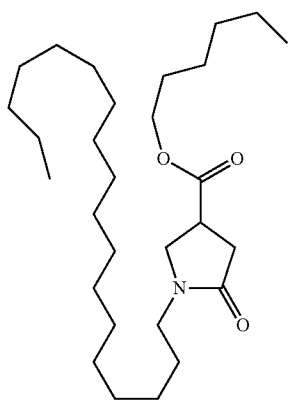
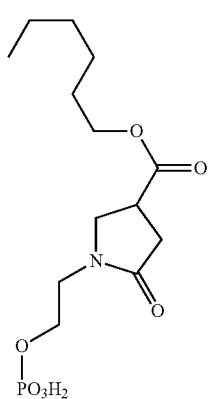
134
-continued
cv
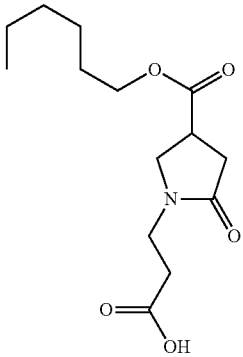
cw
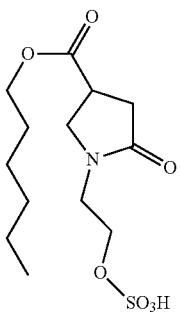
cx
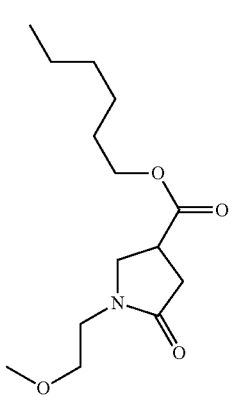
cy
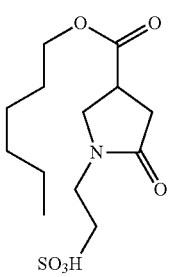
cz
da
db
dc 135
-continued
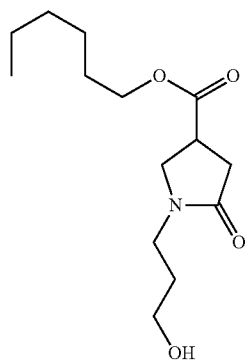
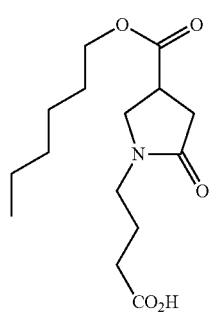
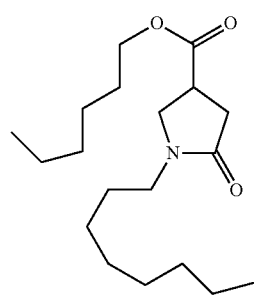
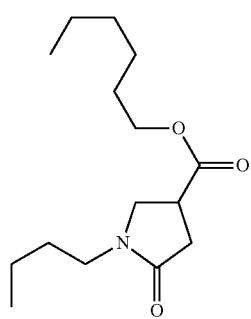
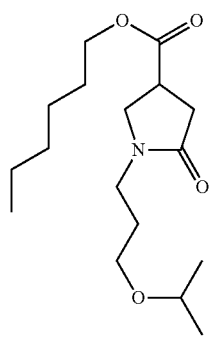
136
-continued
de
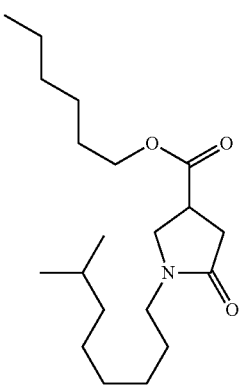
df
dg
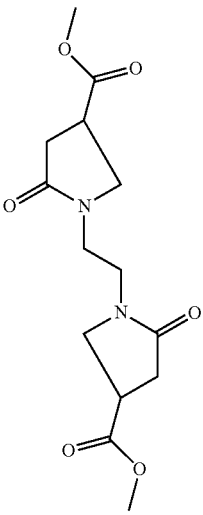
dh
di
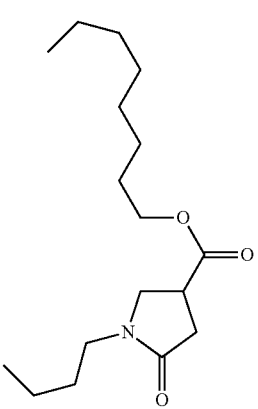
dj
dk
dl

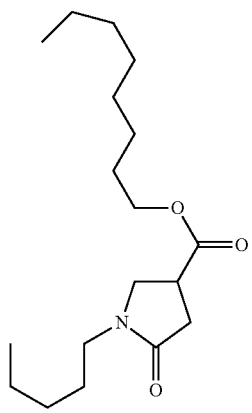
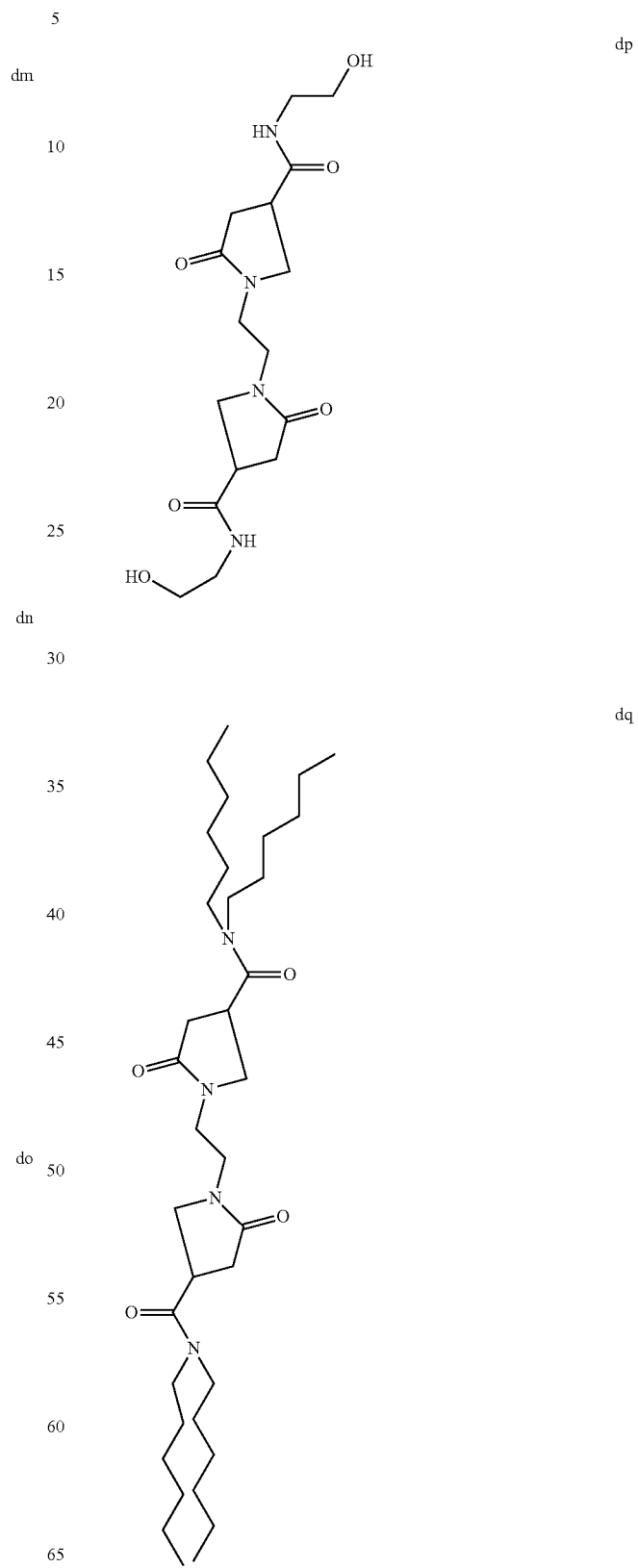

139
-continued
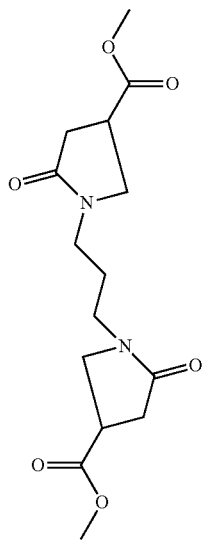
dr
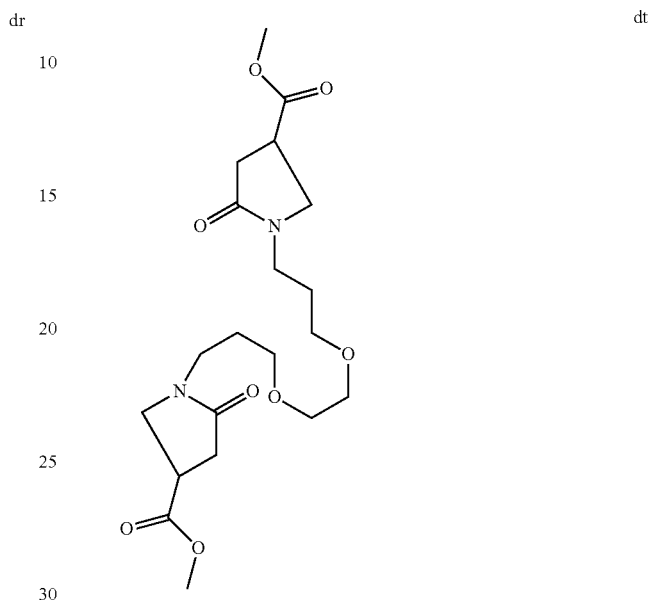
dt
140
-continued
ds
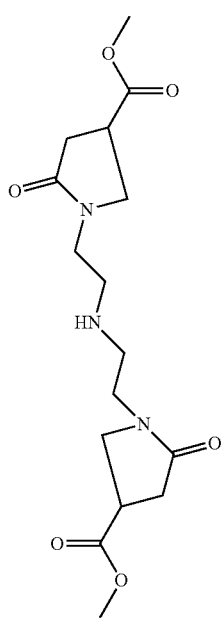
du
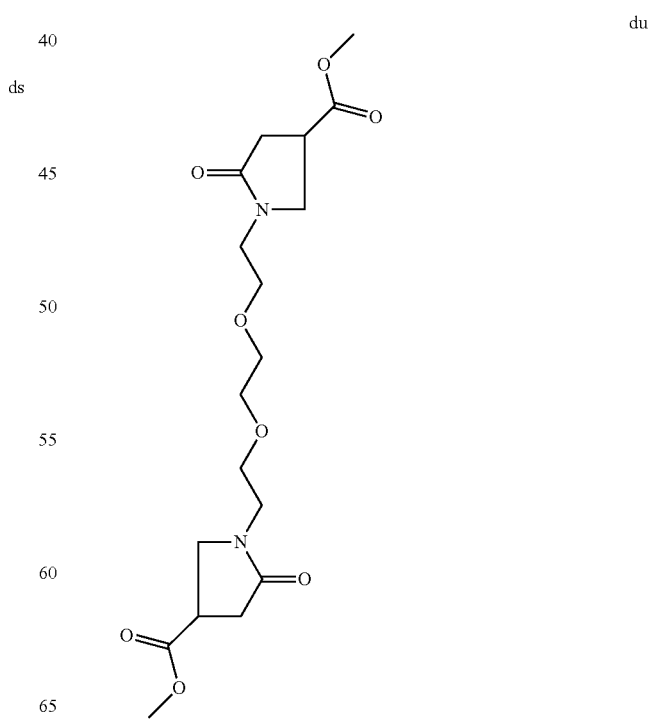

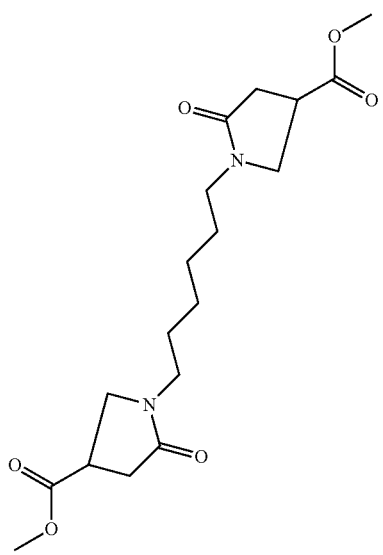
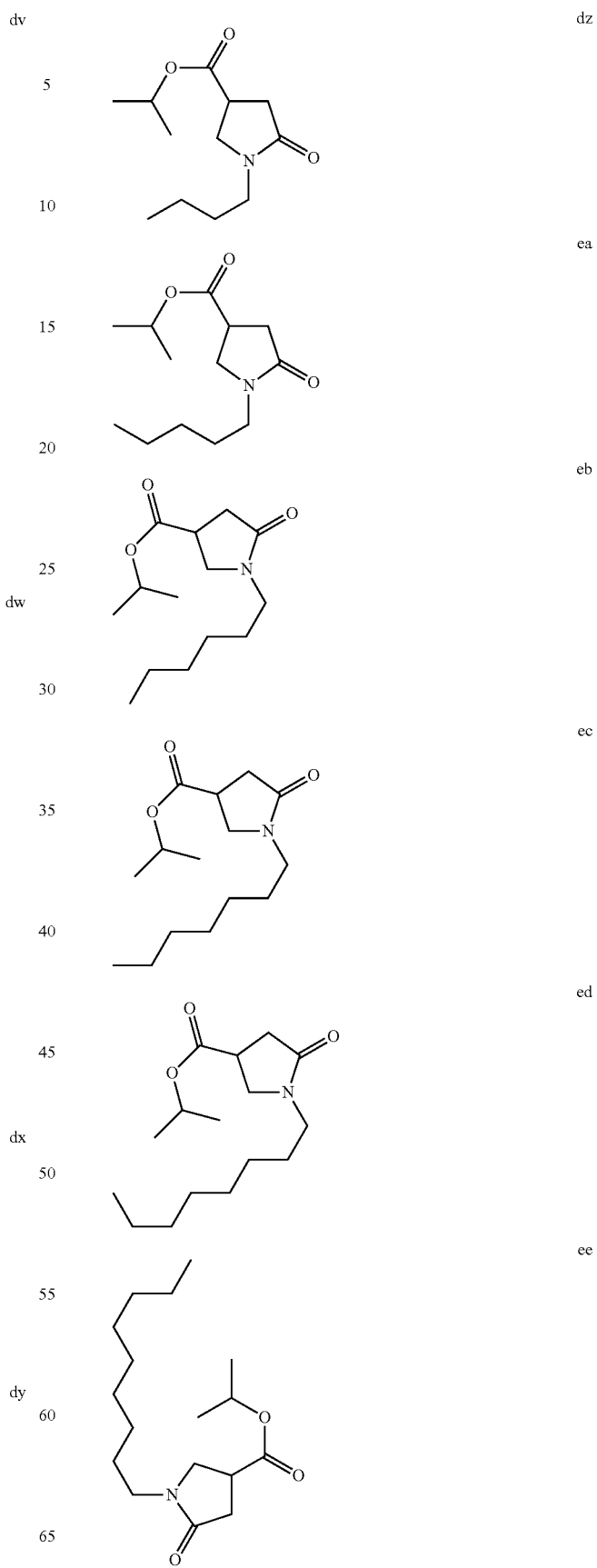

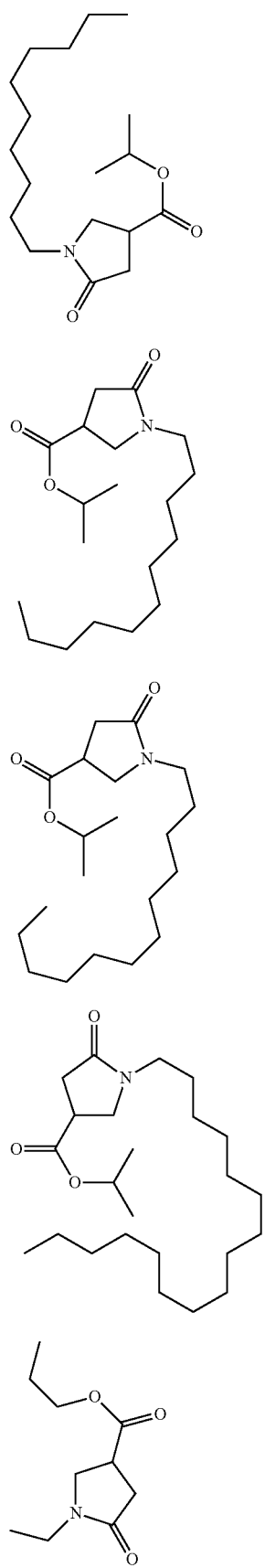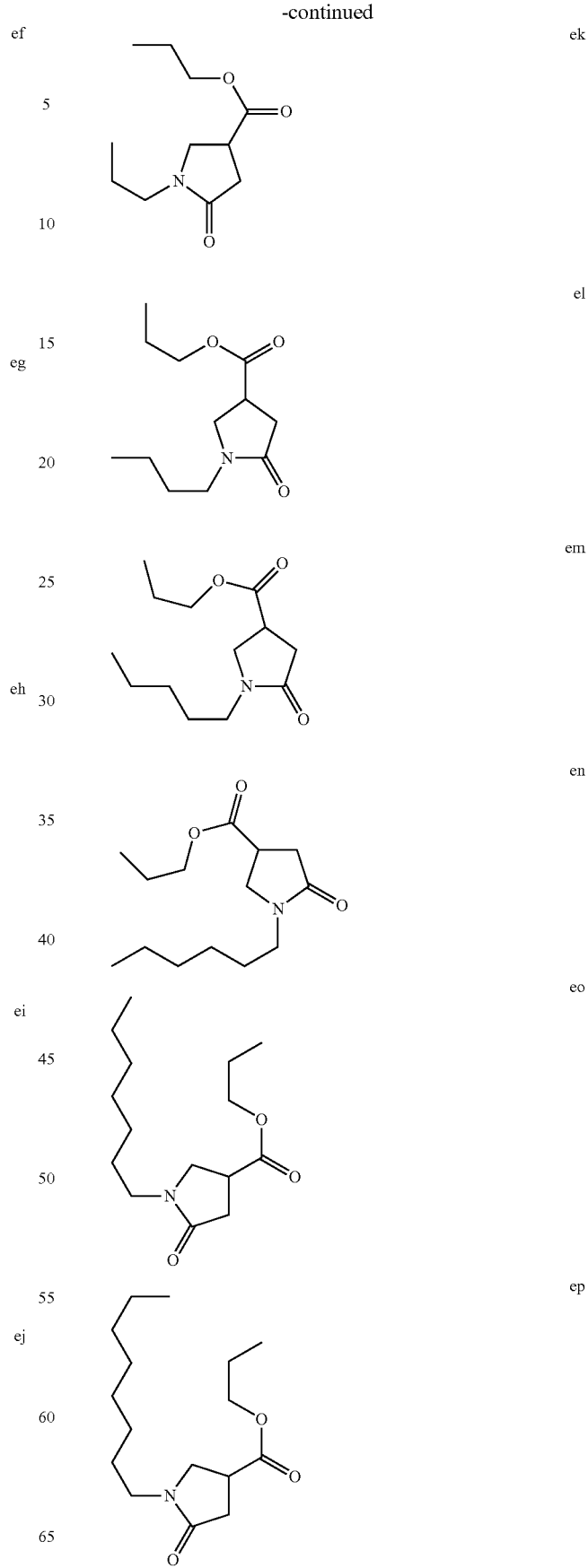

-continued
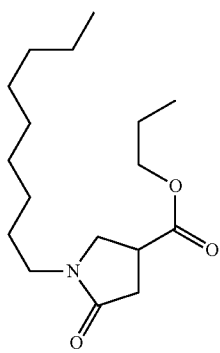
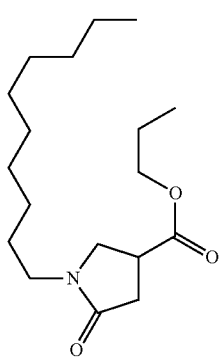
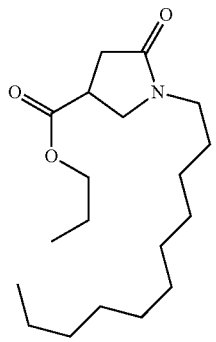
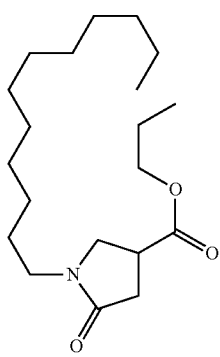
-continued
eq
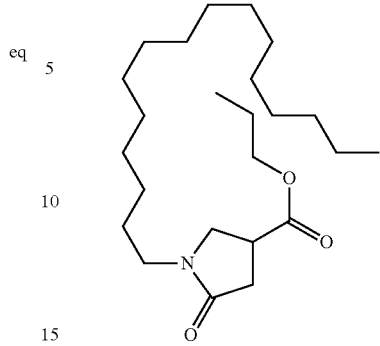
er
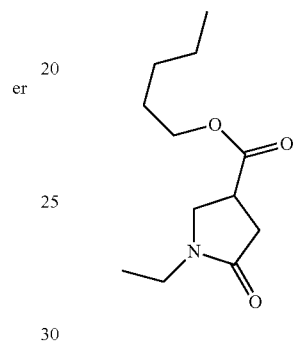
es
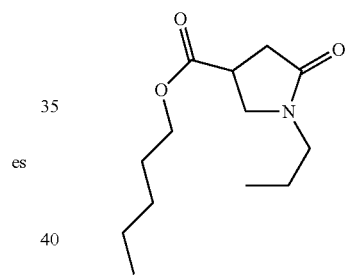
et
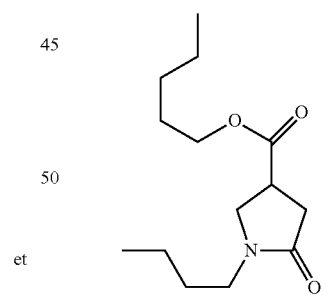
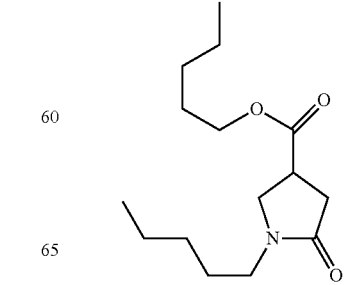
eu
ev
ew
ex
ey 147
-continued
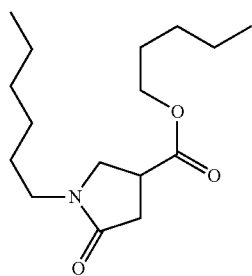
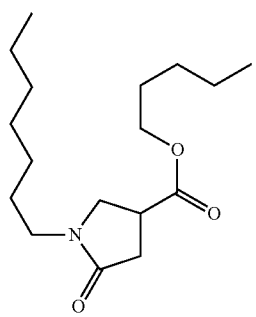
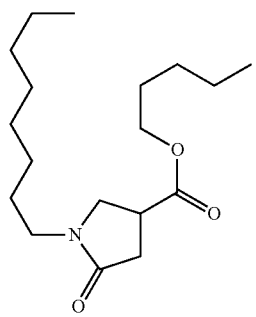
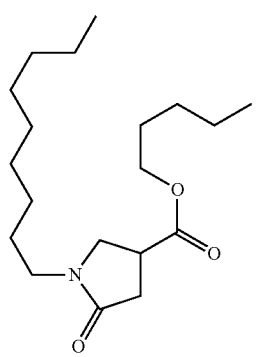
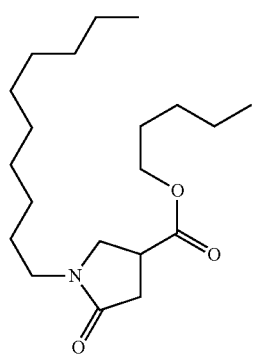
148
-continued
ez
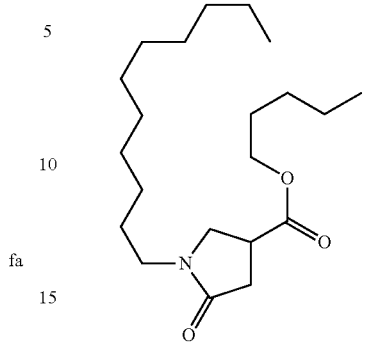
fa
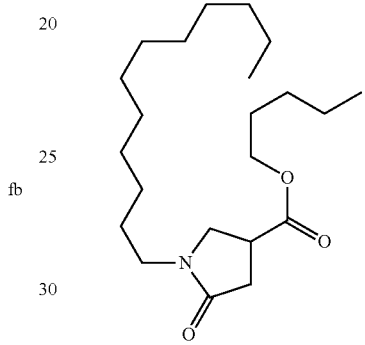
fb
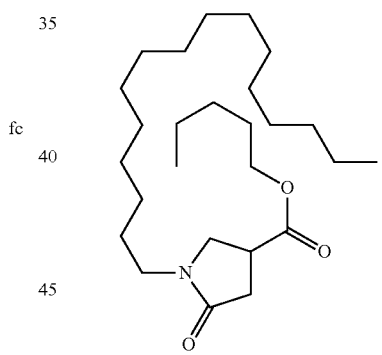
fc
fd
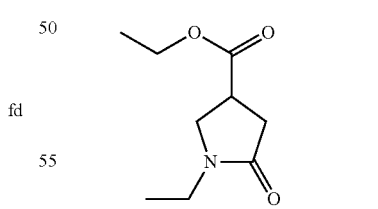
fe
ff
fg
fh
fi
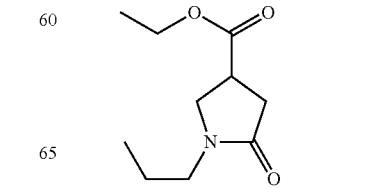

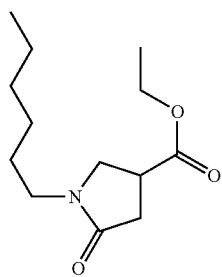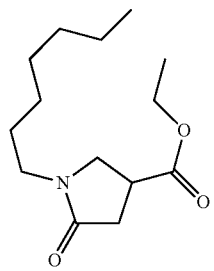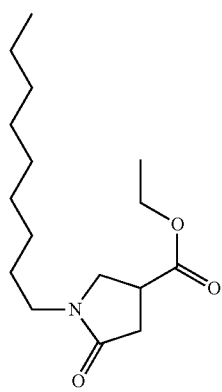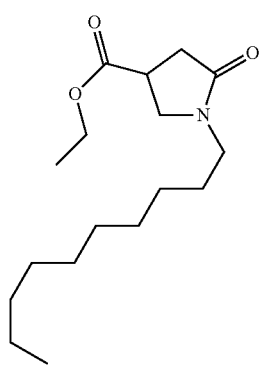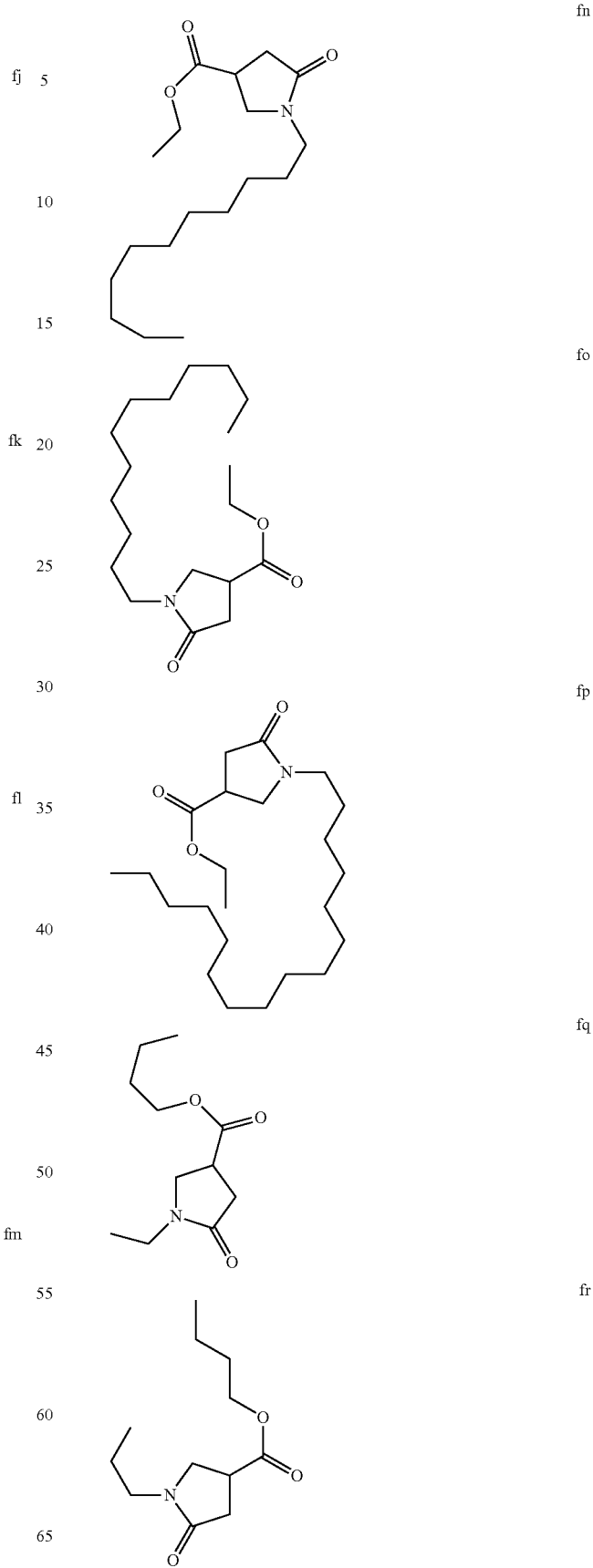

-continued
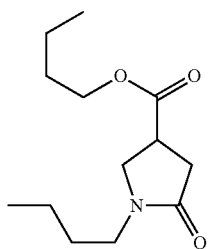
fs
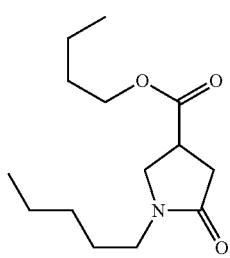
ft
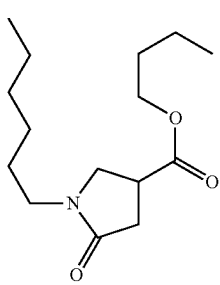
fu
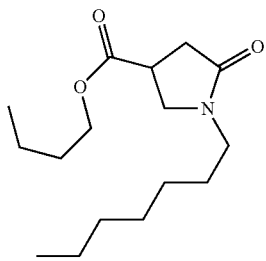
fv
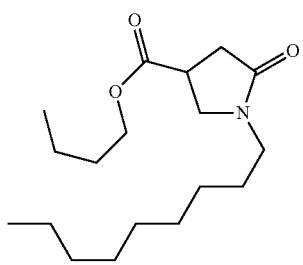
fw
-continued
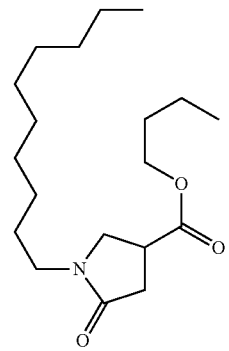
fx
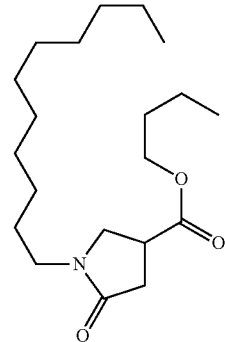
fy
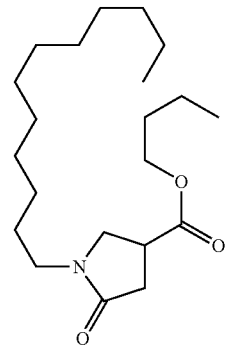
fz
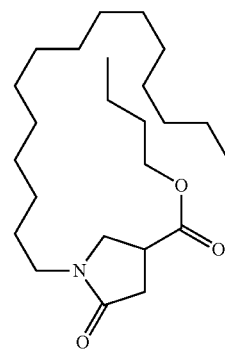
ga

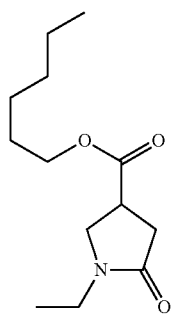
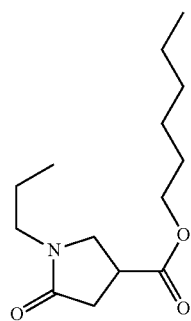
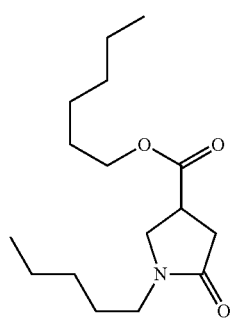
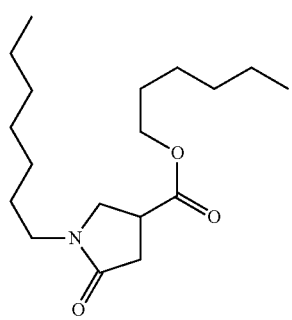
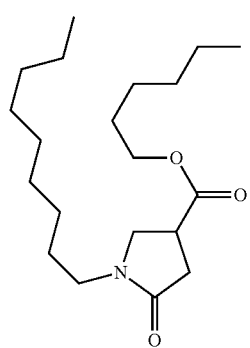
gb
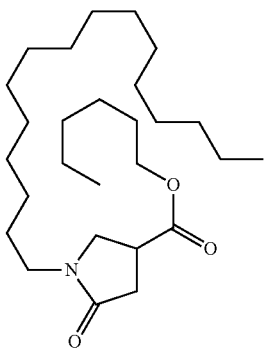
gc
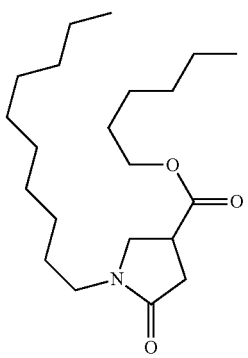
gd
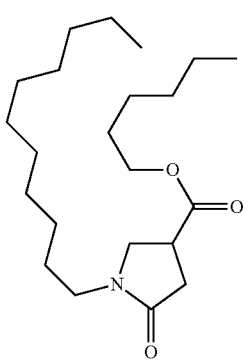
ge
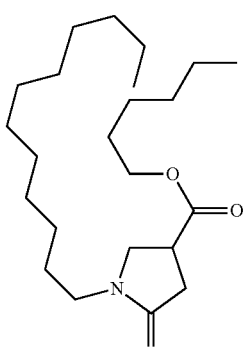
gf
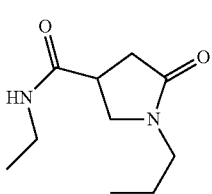
gh
gi
gj
gk
gl

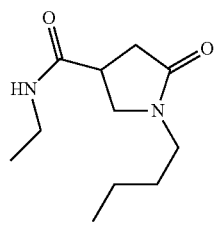 gm
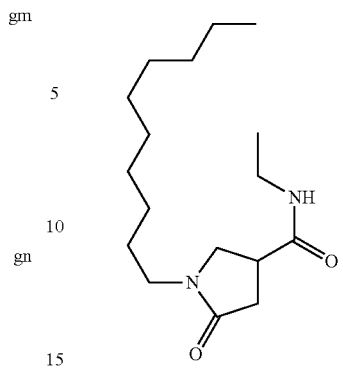 gs
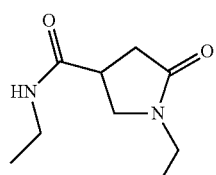 gn
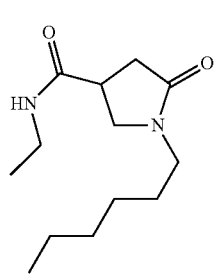 go
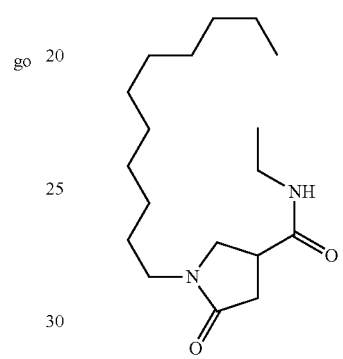 gt
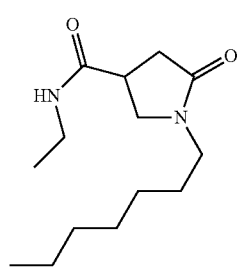 gp
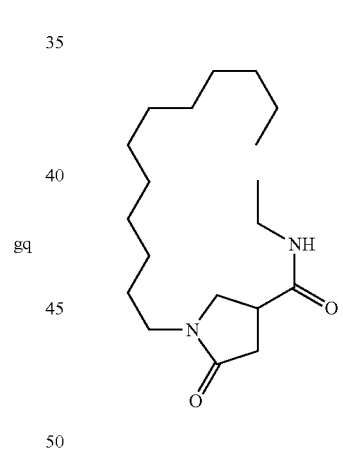 gu
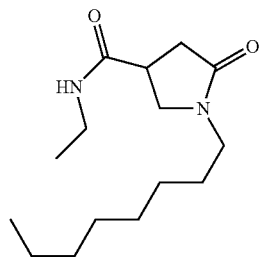 gq
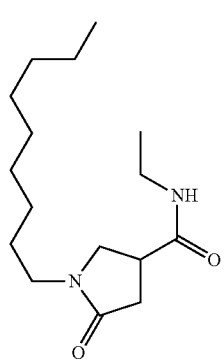 gr
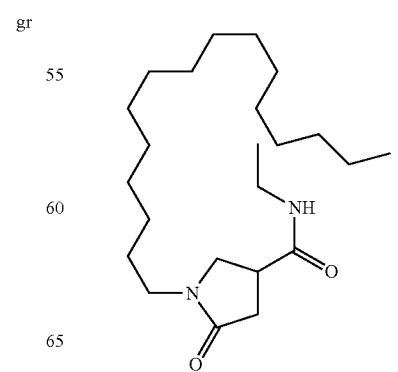 gv gw 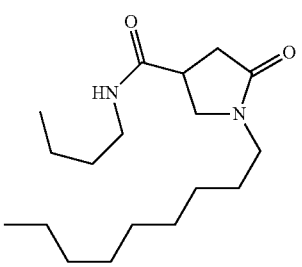
gx 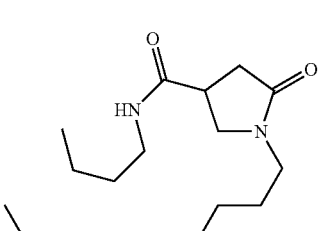
gy 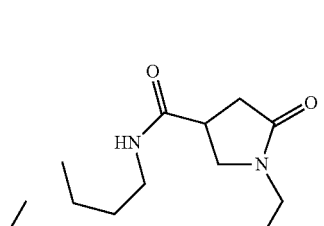
gz
ha 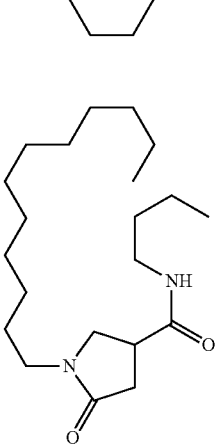
hb 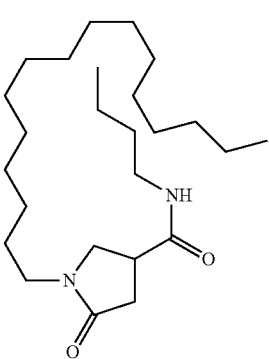
hc 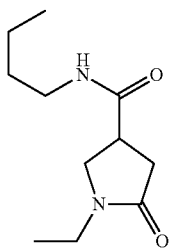
hd 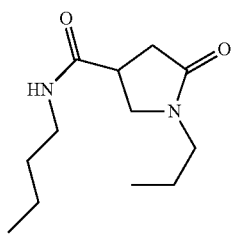
he 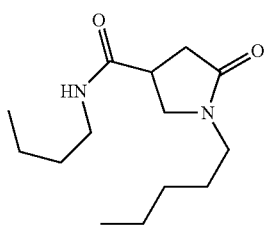
hf 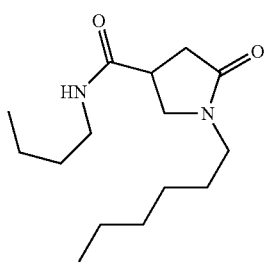
hg 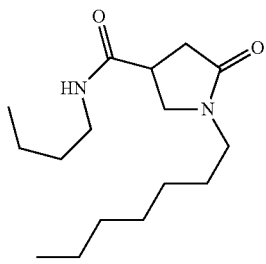
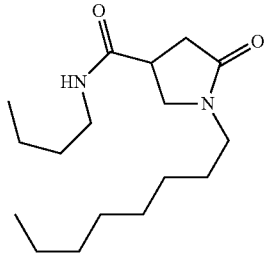

hh
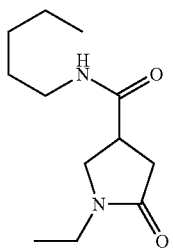
hi
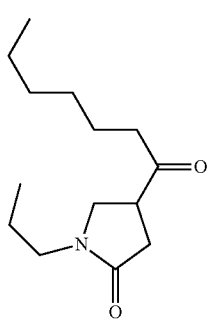
hj
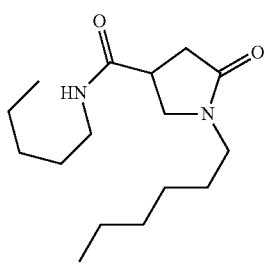
hk
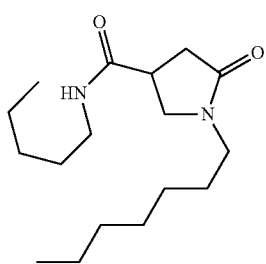
hl
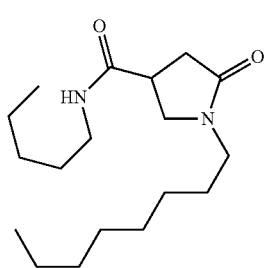
hm
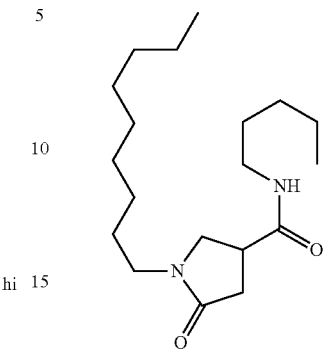
hn
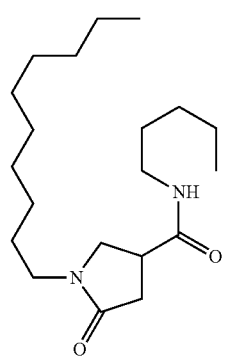
ho
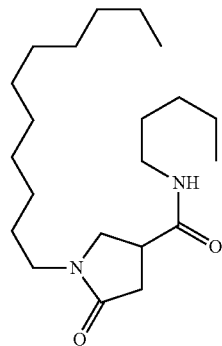
hp
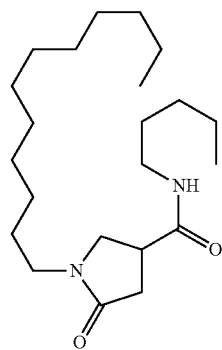

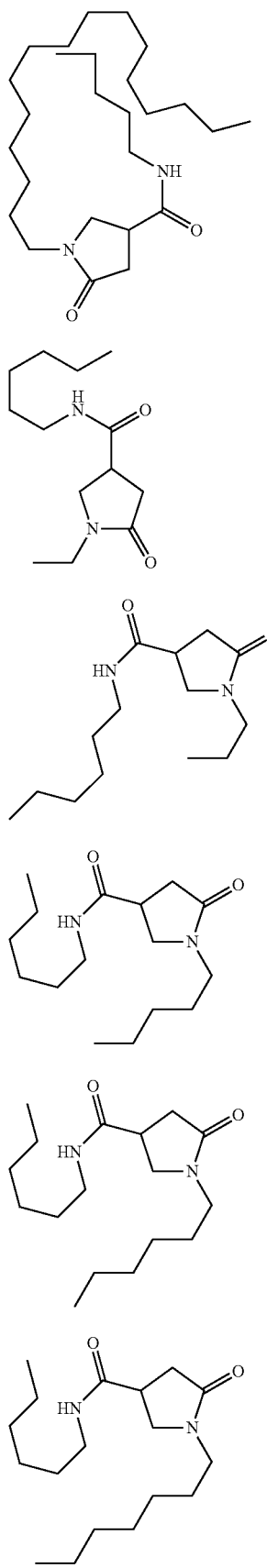
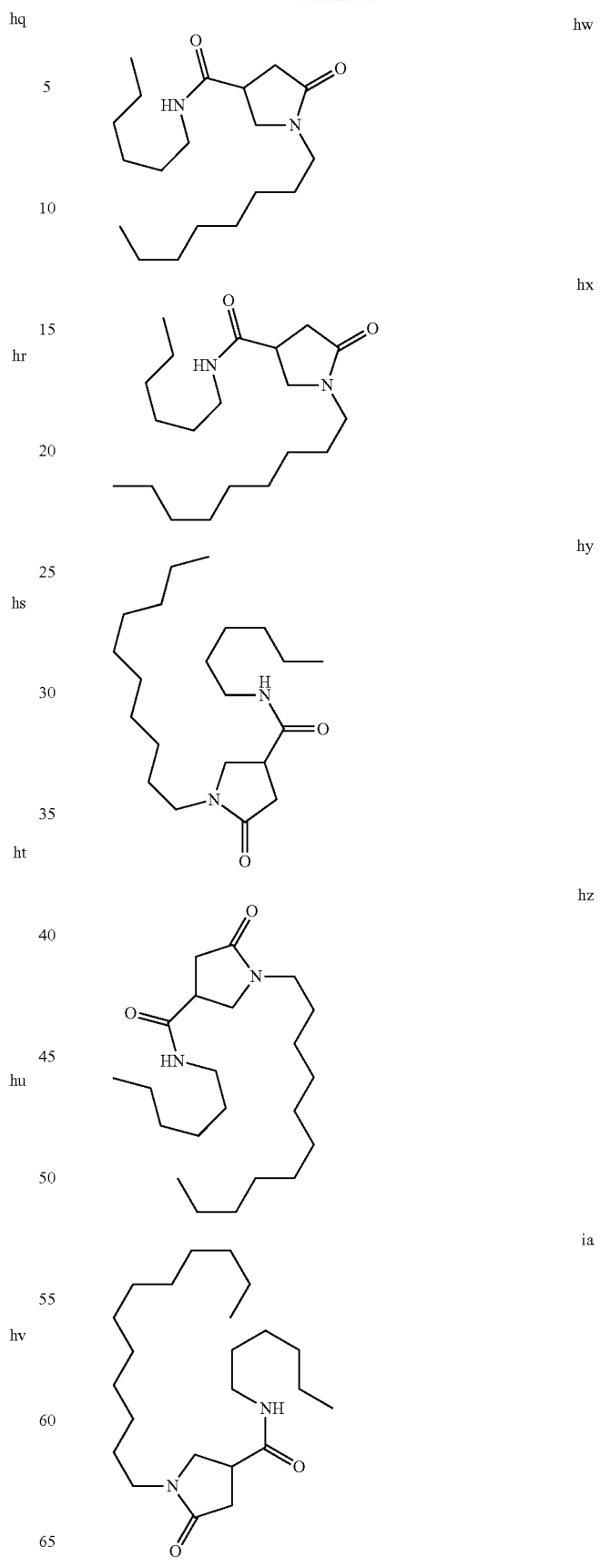

-continued
ib
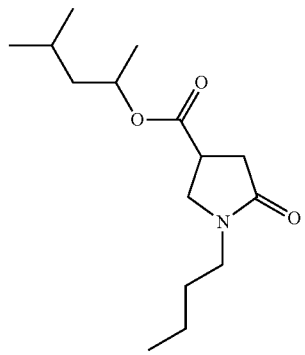
-continued
if
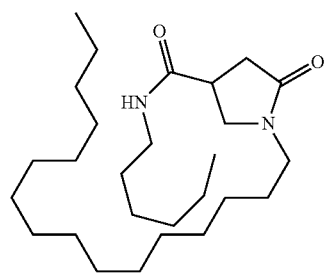
ic
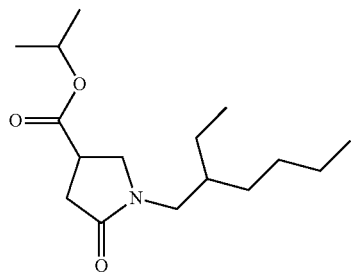
ig
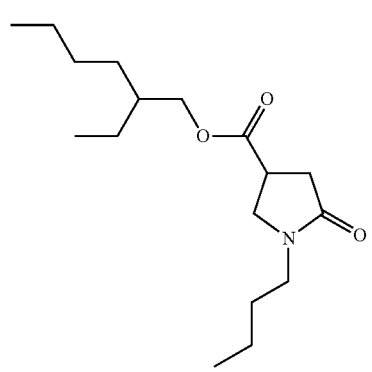
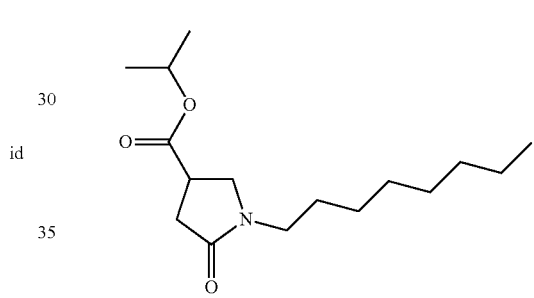
ih
id
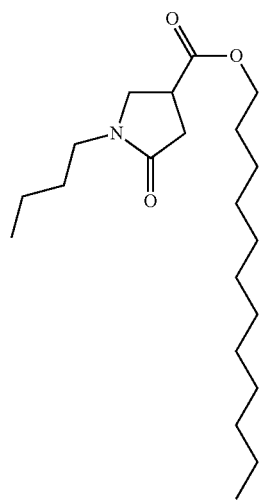
wherein $Q^{31}$ is an anionic counterion; and
1
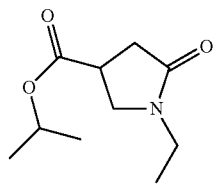
ie
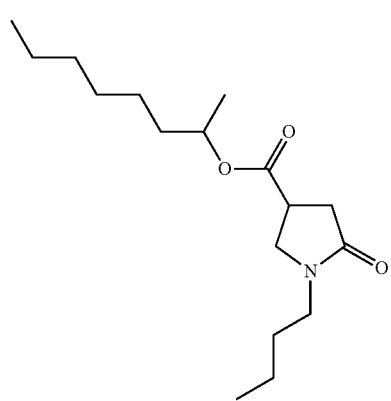
2
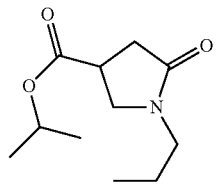
3
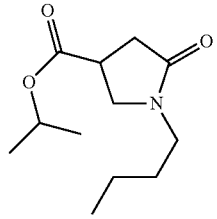

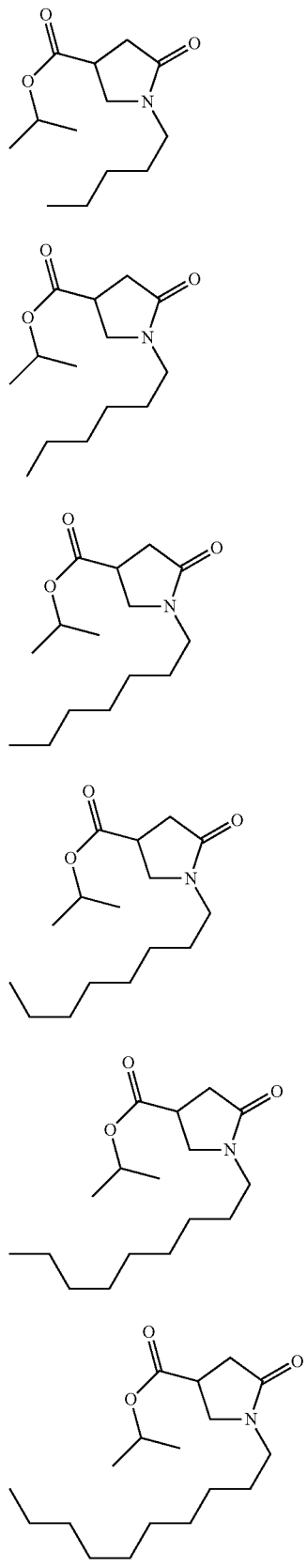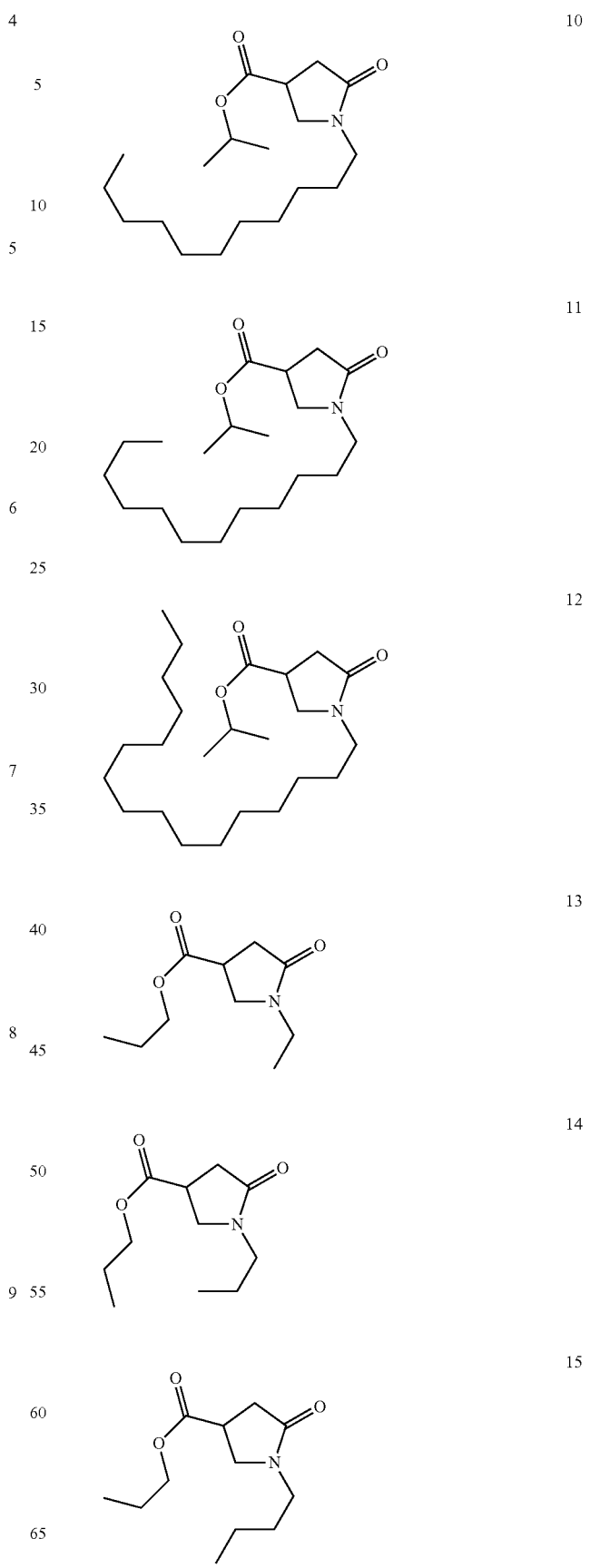

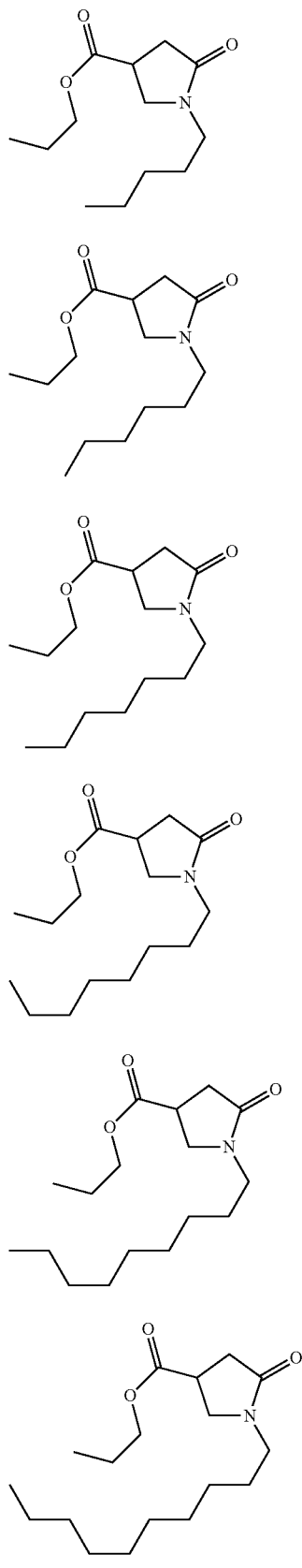
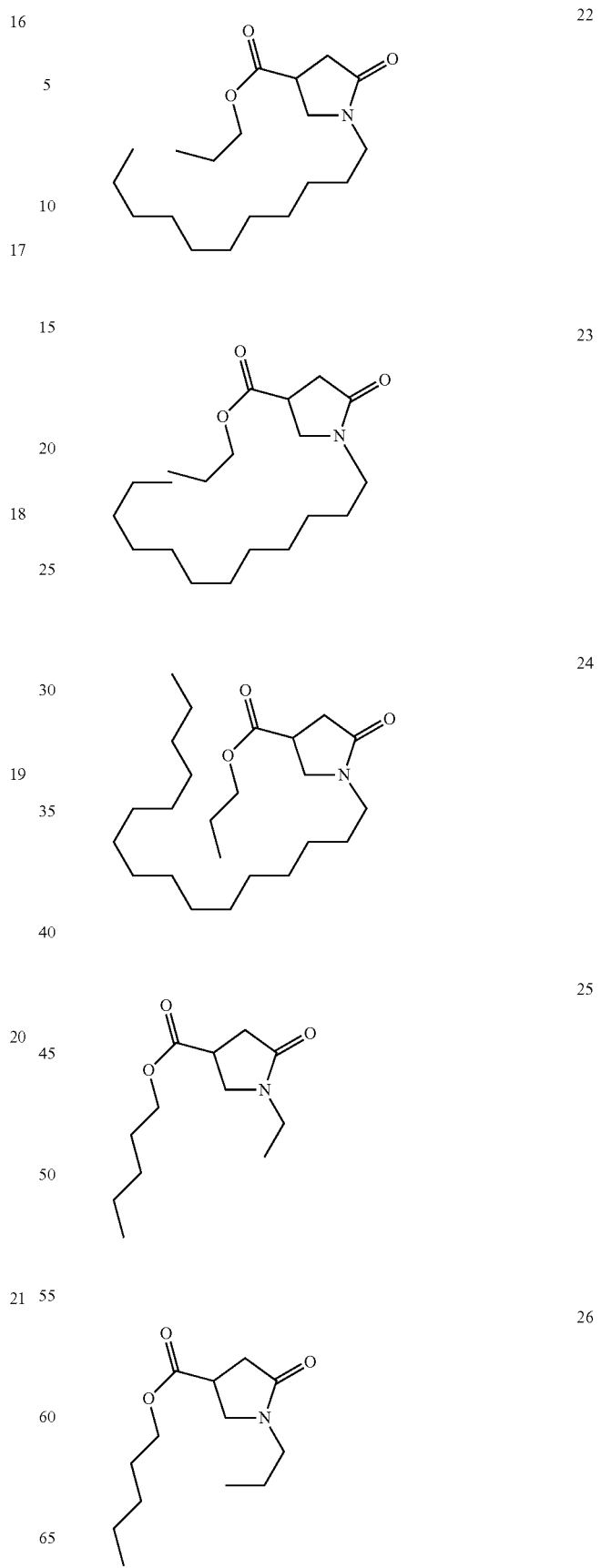

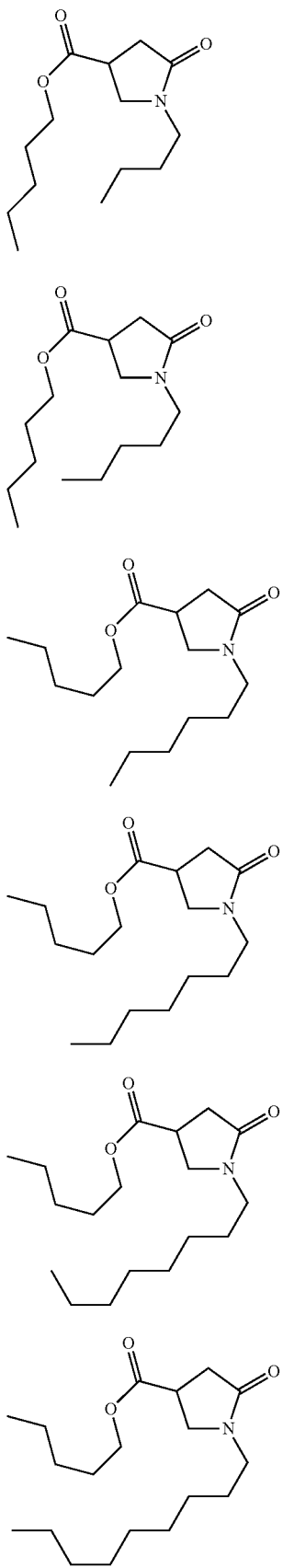
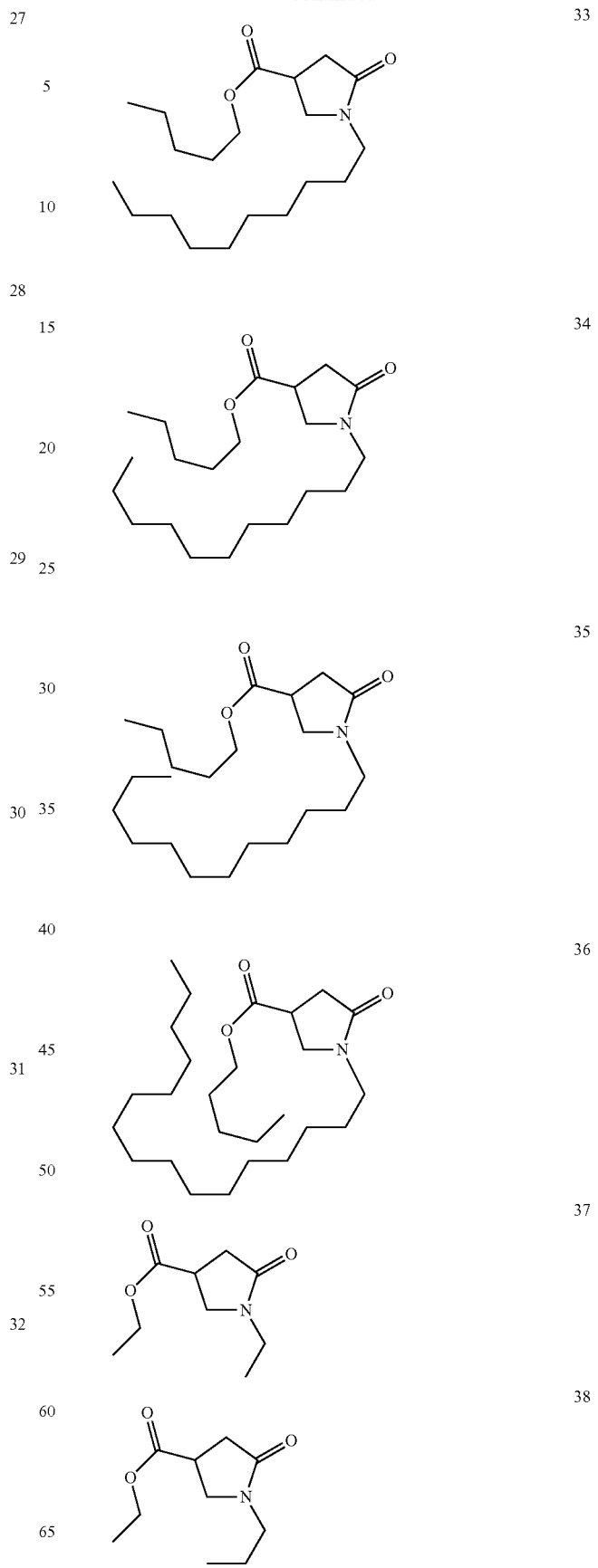

171
-continued
39
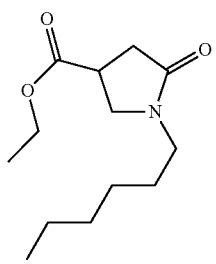
40
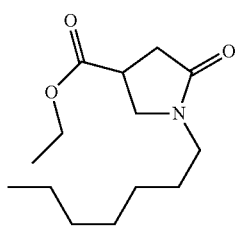
41
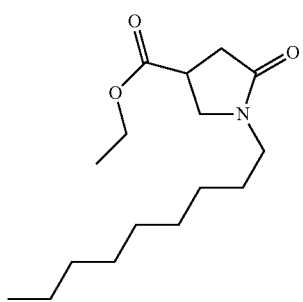
42
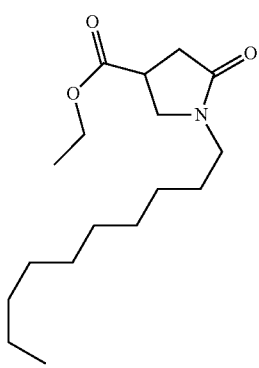
43
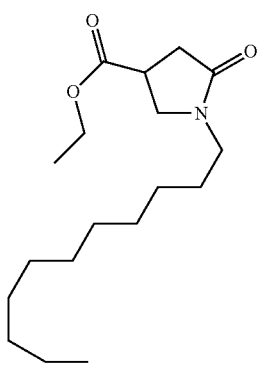
172
-continued
44
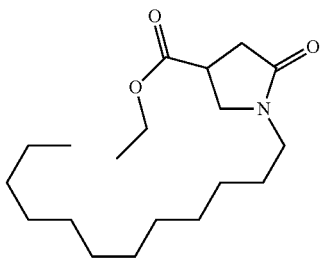
45
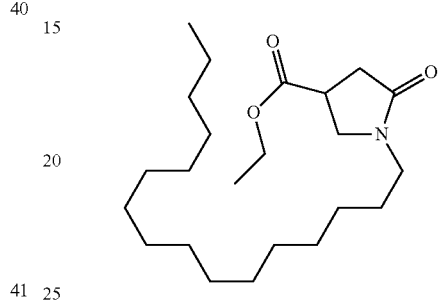
46
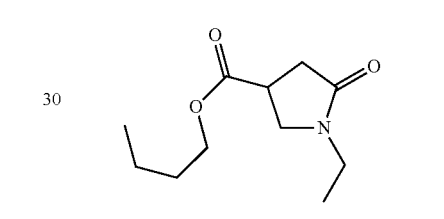
47
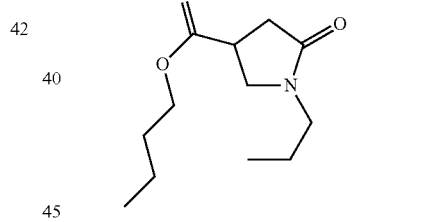
48
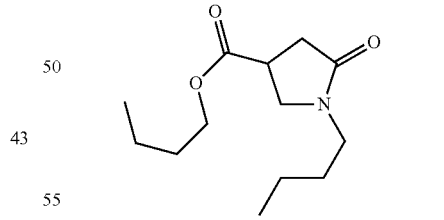
49
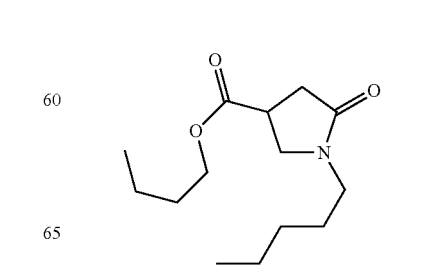

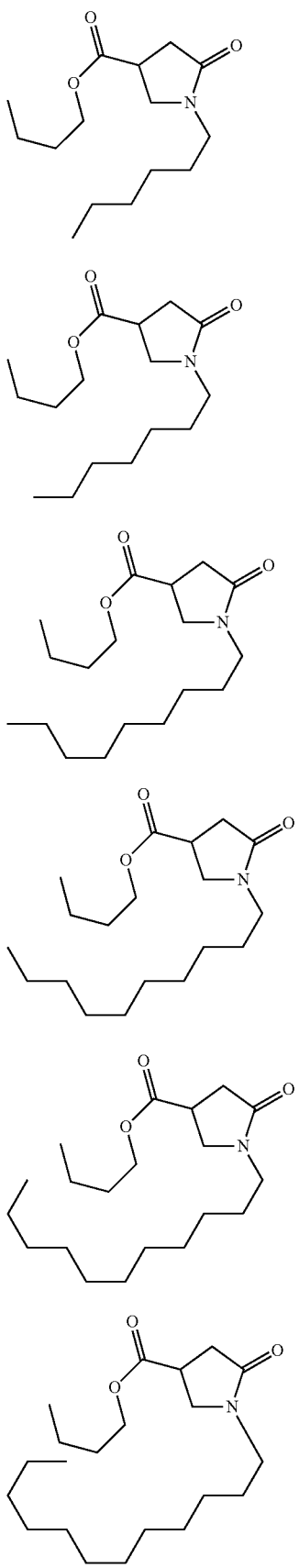
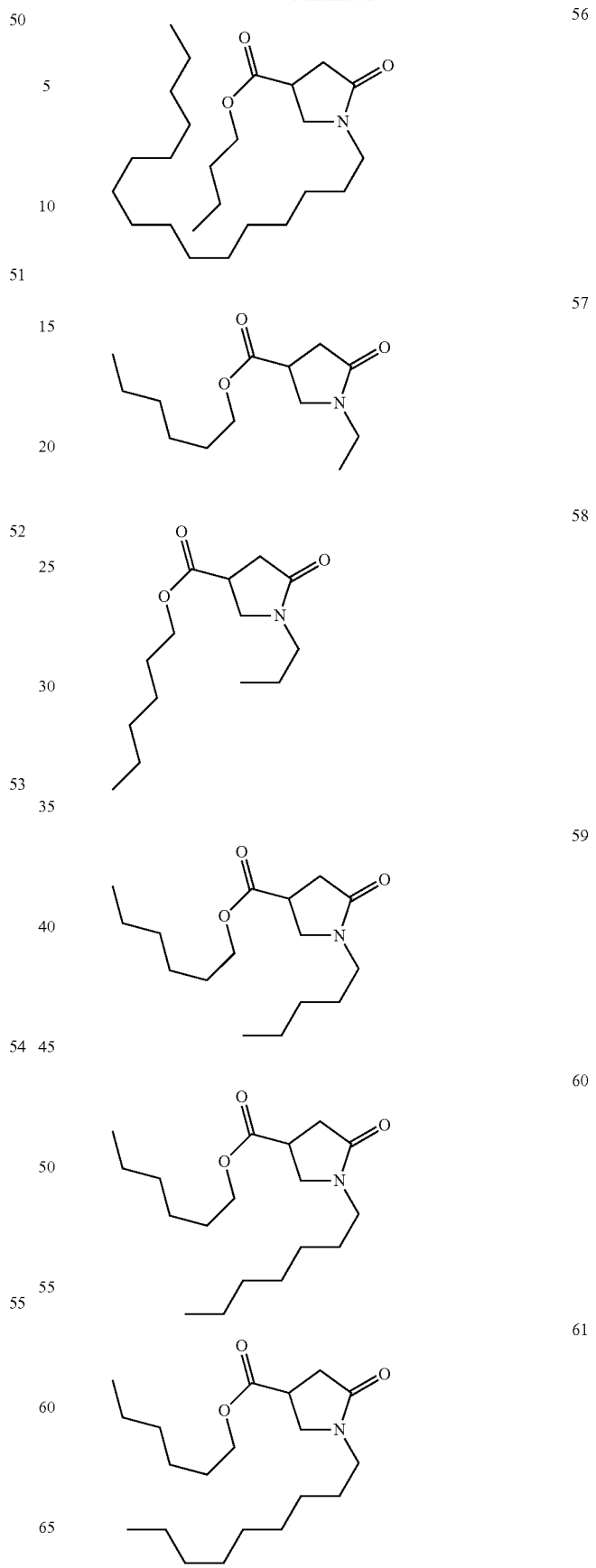

175
-continued
62
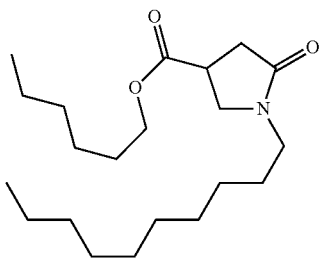
63
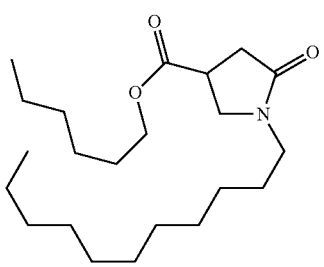
64
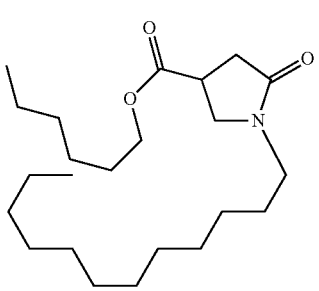
65
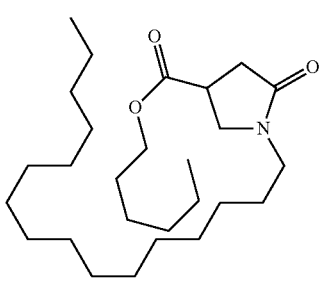
66
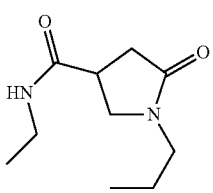
68
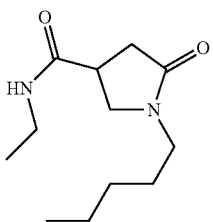
176
-continued
69
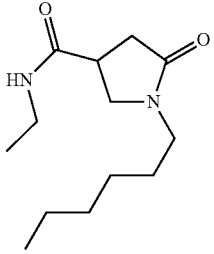
70
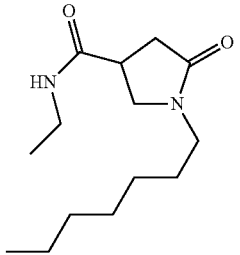
71
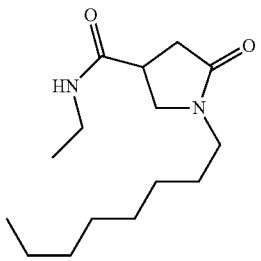
72
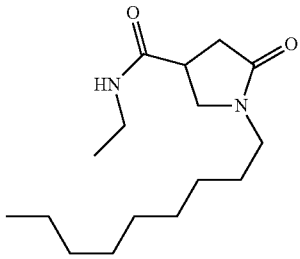
73
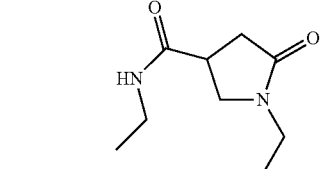
74
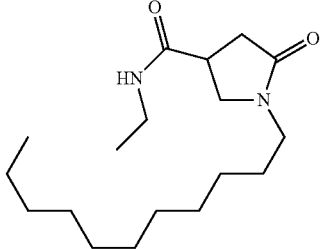

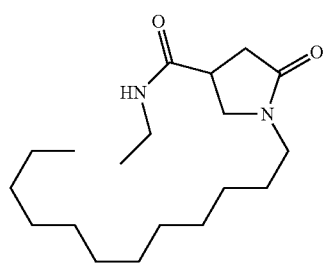
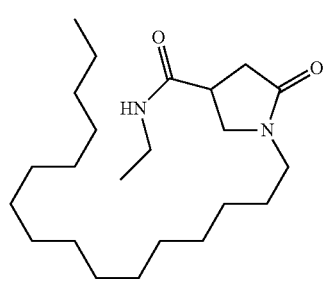
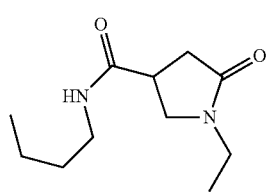
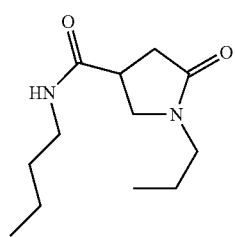
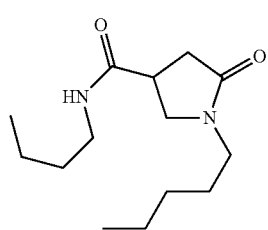
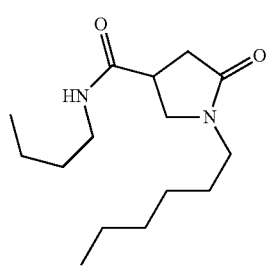
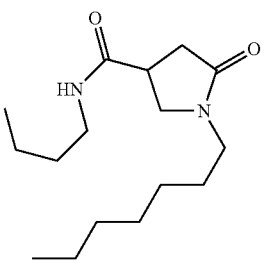
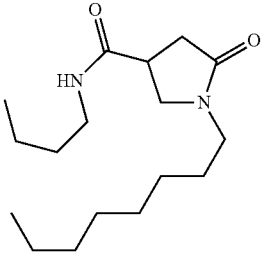
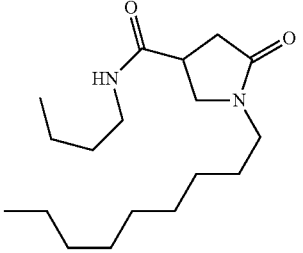
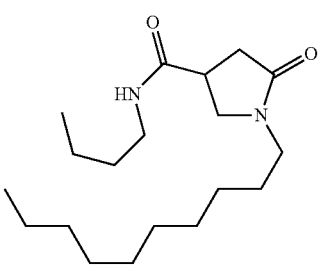
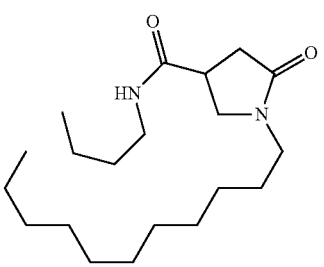
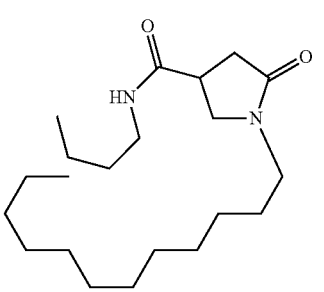

87
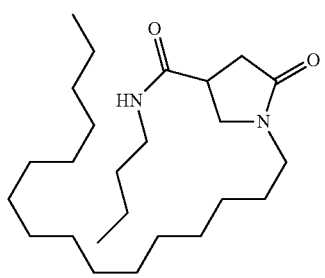
88
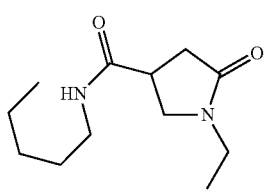
89
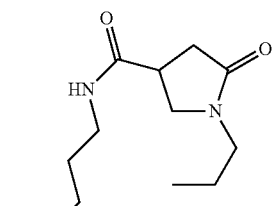
90
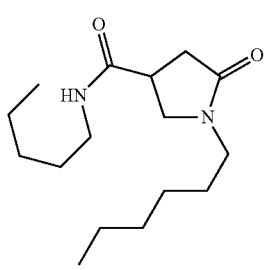
91
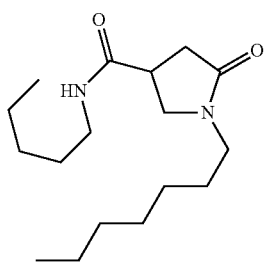
92
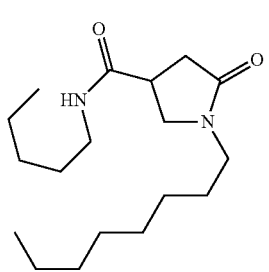
93
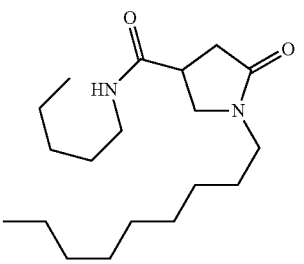
94
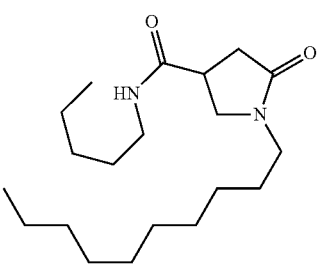
95
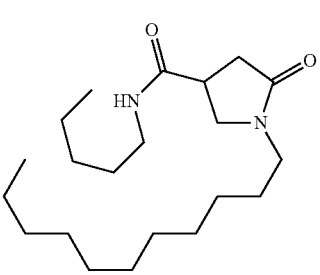
96
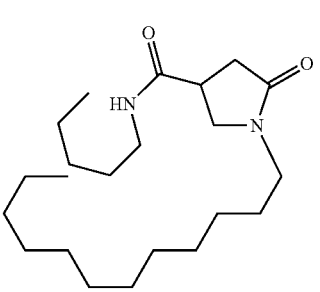
97
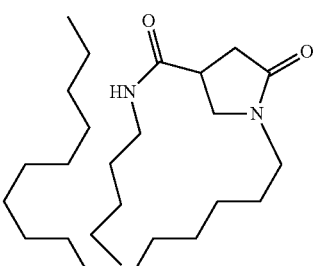
98
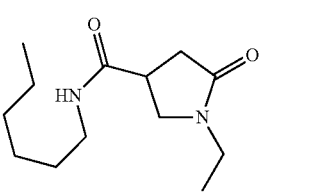

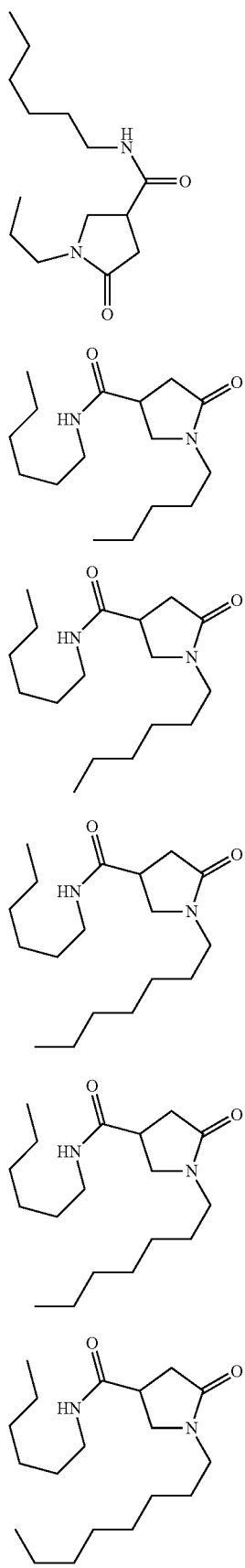
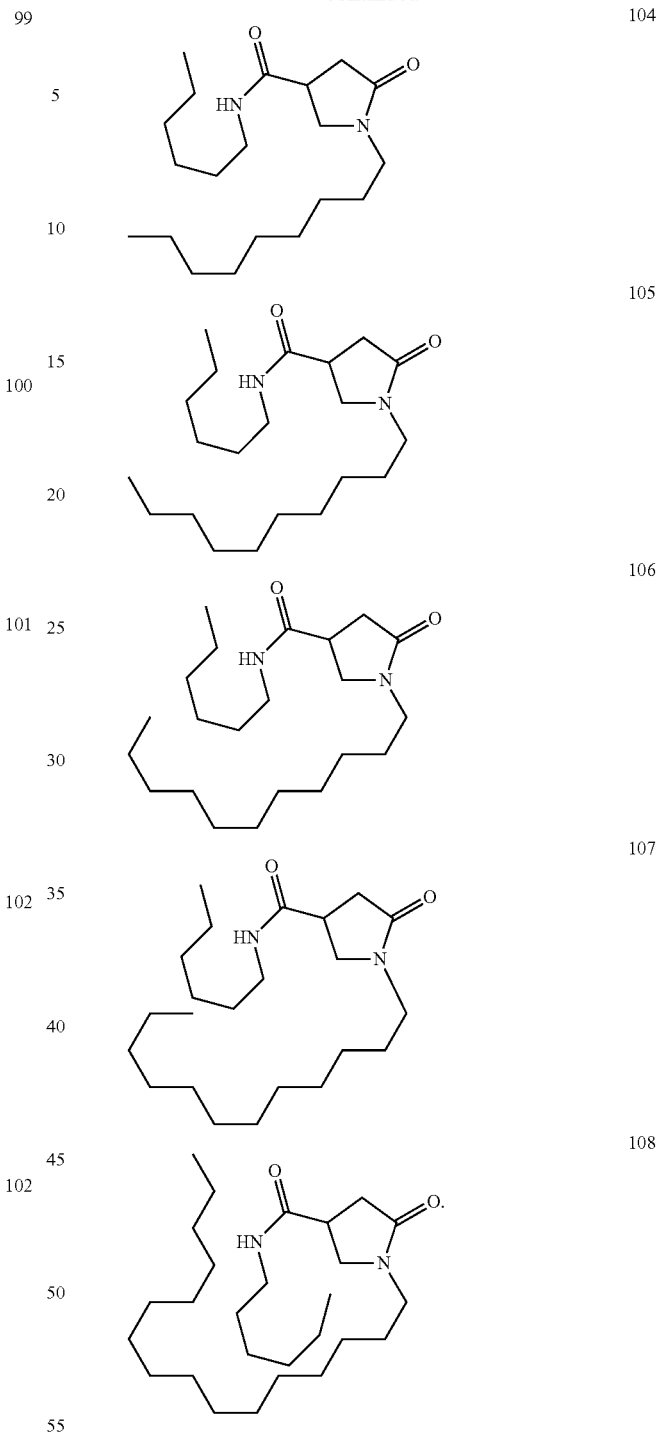

17. The composition according to claim 1, wherein the at least one colorant is chosen from neutral, acidic or cationic nitrobenzene direct dyes, neutral, acidic or cationic azo direct dyes, tetraazapentamethine dyes, neutral, acidic or cationic quinone dyes, acidic or cationic anthraquinone dyes, azine direct dyes, triarylmethane direct dyes, azomethine direct dyes, and natural direct dyes.

18. A method for dyeing keratin materials, comprising applying to the keratin materials i) at least one compound of formula (I) as defined in claim 1 and ii) at least one colorant chosen from pigments and direct dyes, wherein the at least one colorant is sparingly soluble or insoluble in aqueous-alcoholic solvents, and wherein the components i) and ii) are applied to the keratin materials simultaneously in one step, successively, or in several steps.

19. A 2-pyrrolidinone compound functionalized in position 4 with an amide function chosen from:
(a) compounds of formula (Ia) and the organic or mineral acid salts thereof, optical isomers thereof, stereoisomers, enantiomers or diastereoisomers thereof, and the solvates or hydrates thereof:

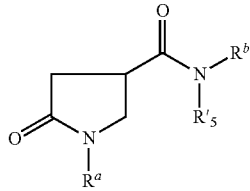

(Ia)

wherein in formula (Ia):
$R'_5$ is chosen from hydrogen and linear or branched ($C_1$-$C_{20}$) alkyl groups;
$R^a$ is chosen from linear or branched ($C_2$-$C_{30}$) alkyl groups; and
$R^b$ is chosen from linear or branched ($C_1$-$C_{20}$) alkyl groups;
wherein $R^a$ is not a branched chain chosen from isopropyl —CH(CH$_3$)$_2$, n-butyl —(CH$_2$)$_3$—CH$_3$, tert-butyl —C(CH$_3$)$_3$, isopentyl —CH$_2$—CH$_2$—CH(CH$_3$)$_2$, and —CH$_2$—CH(CH$_2$CH$_3$)—n—Bu; and
wherein the compounds of formula (Ia) are not:

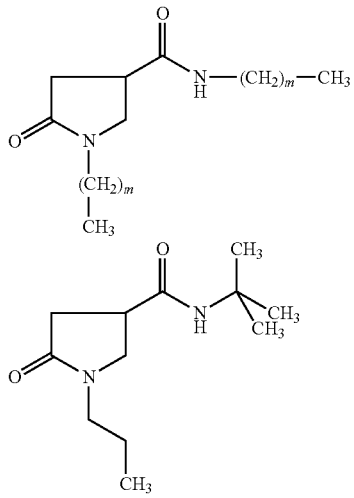

wherein m=1, 4, 7, 11 and 17; and
(b) compounds 1 to 108 as defined in claim 16 and the organic or mineral acid salts thereof, optical isomers thereof, stereoisomers, enantiomers or diastereoisomers thereof, and the solvates or hydrates thereof.

20. A method for improving the color uptake on keratin fibers of at least one colorant chosen from direct dyes and pigments that are sparingly soluble or insoluble in standard aqueous alcoholic supports, the method comprising applying to the keratin fibers i) the at least one colorant and ii) at least one 2-pyrrolidinone compound functionalized in position 4 with an ester or amide of formula (I) as defined in claim 1, wherein the components i) and ii) are applied to the keratin materials simultaneously in one step, successively, or in several steps.

21. A composition comprising, in a suitable cosmetic medium:
i) at least one 2-pyrrolidinone functionalized in position 4 with an ester or amide, chosen from compounds of formula (I):

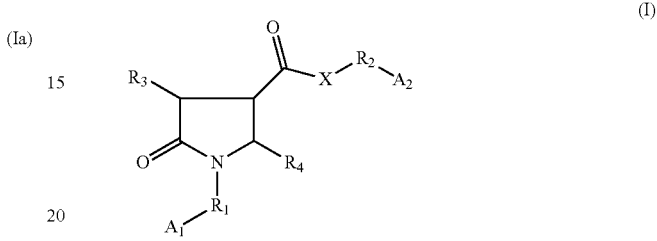

(I)

and the organic or mineral acid or base salts thereof, optical isomers thereof, stereoisomers or enantiomers and diastereoisomers, geometrical isomers and tautomers thereof, and solvates and hydrates thereof;
wherein in formula (I):
X is chosen from oxygen and divalent amino groups —N(R$_5$)—; wherein R$_5$ is chosen from hydrogen, linear or branched (C$_1$-C$_{30}$) alkyl groups optionally substituted with at least one group chosen from —OH, —SH, —NH$_2$, tri(C$_1$-C$_6$)alkylammoniums, and cationic heteroaryl groups;
R$_1$ and R$_2$, which may be identical or different, are chosen from:
a) optionally substituted hydrocarbon-based chains, wherein the hydrocarbon-based chain is a saturated linear C$_1$-C$_{30}$ or branched C$_3$-C$_{30}$ or cyclic C$_3$-C$_7$ chain; and wherein the hydrocarbon-based chain is optionally interrupted with:
i) at least one heteroatom chosen from —O—, —N(R$_6$)— or —S—;
ii) at least one group chosen from —S(O)—, —S(O)$_2$—, —C(O)—, and —N$^+$(R$_6$)(R$_7$)—; a combination of i) and ii); and/or
iii) a 3- to 6-membered saturated or unsaturated carbon-based ring optionally substituted with one or more identical or different radicals chosen from hydroxyl (OH) and amino (—NRR');
b) divalent chains -Cycl-Alk-Cycl'-wherein:
Cycl and Cycl', which may be identical or different, are chosen from cyclic hydrocarbon-based chains, and
Alk is chosen from substituted or unsubstituted (C$_1$-C$_6$) alkylene chains;
c) optionally substituted hydrocarbon-based chains, wherein the hydrocarbon-based chain is a saturated linear C$_2$-C$_{30}$ or branched C$_3$-C$_{30}$ or cyclic C$_3$-C$_7$ chain; and wherein the hydrocarbon-based chain is optionally interrupted with:
i) at least one heteroatom chosen from —O—, —N(R$_6$)— or —S—;
ii) at least one group chosen from —S(O)—, —S(O)$_2$—, —C(O)—, and -N$^+$(R$_6$)(R$_7$)—; a combination of i) and ii); and/or
iii) a 3- to 6-membered saturated or unsaturated carbon-based ring optionally substituted with one or more identical or different radicals chosen from hydroxyl (OH) and amino (—NRR');

$R_1$ and/or $R_2$ substituted with at least one radical chosen from those of formulas (E) and (F):

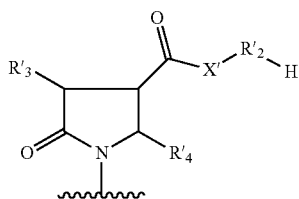

(E)

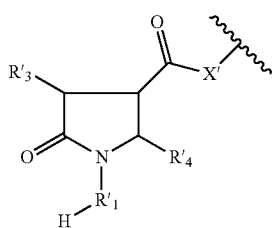

(F)

wherein in formulas (E) and (F):
X' is chosen from oxygen —O— and —N($R_5$) groups;
$R'_1$ and $R'_2$, which may be identical or different, are as defined for $R_1$ and $R_2$, but cannot be substituted with the radicals (E) or (F):

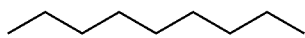

represents the point of attachment of the radicals (E) and (F) to the rest of the molecule;
$A_1$ and $A_2$, which may be identical or different, are chosen from: hydrogen, and groups chosen from a) —OH; b) —SH; c) —NRR'; d) —O—P(O)(OH)$_2$; e) —O—S(O)$_2$OH; f) —S(O)$_2$OH; g) —C(O)OH; h) saturated or unsaturated 3- to 6-membered (hetero)cycles optionally substituted with at least one identical or different radical chosen from (hydroxy)($C_1$-$C_6$) alkyl, hydroxyl and —NRR', the (hetero)cycles possibly being cationic; i) —N$^+$($R_7$)($R_8$)($R_9$); j) RR'N—C(=NR")—N(R)— and

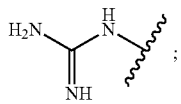

and k) radicals of formula (G) or (H):

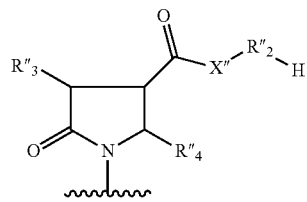

(G)

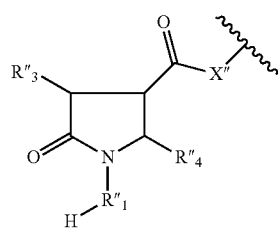

(H)

wherein in formulas (G) and (H):
X" is chosen from oxygen —O— and —N($R_5$) groups;
$R"_1$ and $R"_2$, which may be identical or different, are as defined for $R'_1$ and $R'_2$;
wherein $A_1$ and $A_2$ do not simultaneously represent a radical (G) or (H);
$R_3$, $R_4$, $R'_3$, $R'_4$, $R"_3$ and $R"_4$, which may be identical or different, are chosen from hydrogen and linear $C_1$-$C_{12}$ or branched $C_3$-$C_{12}$ alkyl chains;
$R_6$ is chosen from hydrogen and linear ($C_1$-$C_{20}$) alkyl or branched ($C_3$-$C_{20}$) alkyl groups, optionally substituted with a radical (G) or (H);
$R_7$, $R_8$ and $R_9$, which may be identical or different, are chosen from hydrogen and ($C_1$-$C_6$) alkyl groups optionally substituted with at least one hydroxyl group; and
R, R' and R", which may be identical or different, are chosen from hydrogen atom and ($C_1$-$C_{18}$) alkyl groups optionally substituted with at least one hydroxyl group;
wherein when $A_1$, $A_2$, $R_1$, $R_2$, and/or $R_5$ contain or denote a cationic group, the electrical neutrality of the compounds of formula (I) is ensured by an anionic counterion or a mixture of anionic counterions; and
wherein when X is oxygen, $R_3$, $R_4$, $A_1$ and $A_2$ do not simultaneously represent a hydrogen atom; and
ii) at least one colorant chosen from pigments, wherein the at least one colorant is sparingly soluble or insoluble in standard aqueous-alcoholic supports.

* * * * *

UNITED STATES PATENT AND TRADEMARK OFFICE
CERTIFICATE OF CORRECTION

PATENT NO. : 8,771,376 B2
APPLICATION NO. : 13/703040
DATED : July 8, 2014
INVENTOR(S) : Stephane Sabelle et al.

Page 1 of 1

It is certified that error appears in the above-identified patent and that said Letters Patent is hereby corrected as shown below:

In the Claims

Column 164, Claim 16, line 40, "$Q^{31}$" should be -- $Q^-$ --

Signed and Sealed this
Ninth Day of September, 2014

Michelle K. Lee
*Deputy Director of the United States Patent and Trademark Office*